US006319922B1

(12) United States Patent
Alexander et al.

(10) Patent No.: US 6,319,922 B1
(45) Date of Patent: Nov. 20, 2001

(54) PROPANOIC ACID DERIVATIVES

(75) Inventors: Rikki Peter Alexander, High Wycombe; Barry John Langham, Reading; James Thomas Reuberson; Emma Louise Trown, both of Slough; Graham John Warrellow, Northwood, all of (GB)

(73) Assignee: Celltech Therapeutics Limited (GB)

( * ) Notice: Subject to any disclaimer, the term of this patent is extended or adjusted under 35 U.S.C. 154(b) by 0 days.

(21) Appl. No.: 09/448,840

(22) Filed: Nov. 23, 1999

(30) Foreign Application Priority Data

Nov. 23, 1998  (GB) .................................................. 9825652

(51) Int. Cl.$^7$ .......................... A61K 31/53; A01N 43/54; C07D 251/00; C07D 239/02
(52) U.S. Cl. .......................... 514/241; 514/269; 544/214; 544/215; 544/242; 544/243; 544/333; 544/335
(58) Field of Search ...................... 514/241, 269; 544/214, 215, 243, 242, 333, 335

(56) References Cited

U.S. PATENT DOCUMENTS

| | | | |
|---|---|---|---|
| 4,470,973 | 9/1984 | Natarajan et al. | 424/177 |
| 4,554,273 | 11/1985 | Bayssat et al. | 514/221 |
| 4,987,132 | 1/1991 | Mase et al. | 514/252 |
| 5,164,372 | 11/1992 | Matsuo et al. | 514/19 |
| 5,260,277 | 11/1993 | McKenzie | 544/18 |
| 5,296,486 | 3/1994 | Lazer et al. | 514/333 |
| 5,510,346 | 4/1996 | Martin et al. | 514/221 |
| 5,698,691 | 12/1997 | Yukimasa et al. | 540/490 |
| 6,093,696 | 7/2000 | Head et al. | 514/19 |
| 6,229,011 | * 5/2001 | Chen et al. | 544/171 |

FOREIGN PATENT DOCUMENTS

| | | |
|---|---|---|
| 23 16 881 A | 10/1973 | (DE) . |
| 28 37 264 A1 | 3/1979 | (DE) . |
| 196 54 483 A | 1/1998 | (DE) . |
| 0 031 104 A1 | 7/1981 | (EP) . |
| 0 048 763 A1 | 4/1982 | (EP) . |
| 0 144 230 A | 6/1985 | (EP) . |
| 0 288 176 A | 10/1988 | (EP) . |
| 0 322 068 A1 | 6/1989 | (EP) . |
| 0 394 989 A2 | 10/1990 | (EP) . |
| 0 498 268 A2 | 8/1992 | (EP) . |
| 0 596 406 A1 | 5/1994 | (EP) . |
| 0 710 657 A1 | 5/1996 | (EP) . |
| 0 710 659 A1 | 5/1996 | (EP) . |
| 0 842 943 A2 | 5/1998 | (EP) . |
| 0 842 945 A2 | 5/1998 | (EP) . |
| 56 090045 | 7/1981 | (JP) . |
| 03 135962 | 6/1991 | (JP) . |
| WO 86/02353 | 4/1986 | (WO) . |
| WO 93/00095 | 1/1993 | (WO) . |
| WO 93/08174 | 4/1993 | (WO) . |
| WO 93/09795 | 5/1993 | (WO) . |

(List continued on next page.)

OTHER PUBLICATIONS

Alhaique, F., et al., "Cyclisation of dinitriles by sodium alkoxides a new synthesis of naphthyridines," *Tetrahedron Letters*, 1975, 3, 173–174.

Ames, D.E., et al., "Condensation of β–dicarbonyl compounds with halogenopyridinecarb–oxylic acids. A convenient synthesis of some naphthyridine derivatives," *J.C.S. Perkin I*, 1972, 705–710.

Bodor, N., "Novel approaches in prodrug design," *Alfred Benzon Symposium*, 1982, 17, 156–177.

Brooks, Peter C., et al., "Antiintegrin αvβ3 blocks human breast cancer growth and angiogenesis in human skin," *J. Clin. Invest.*, 1995, 96, 1815–1822.

Bundgaard, H., *Design of Prodrugs*, 1985, Elsevier, Amsterdam.

Katritzky, A.R., et al. (Eds.), Comprehensive Organic Functional Group Transformations, Pergamon, 1995.

Davies, S..G., "Asymmetric synthesis of R–β–amino butanoic acid and S–β–tyrosine: homochiral lithium amide equivalents for Michael additions toα,β–unsaturates esters," *Tetra. Assymmetry*, 1991, 2(3), 183–186.

Erle, D.J., et al., "Expression and function of the Mad-CAM–1 receptor, integrin α4β7, on human leukocytes," *J. Immunol.*, 1994, 153, 517–528.

Encyclopedia of Reagents for Organic Synthesis, John Wiley & Sons (eds.), 1995.

Giacomello, et al., "Synthesis of 2,6–naphthyridine," *Tetra. Letters*, 1965, 16, 1117–1121.

Green, T.W., et al., "Protective Groups in Organic Synthesis," *John Wiley and Sons* (eds.), 1991.

(List continued on next page.)

*Primary Examiner*—Mukund J. Shah
*Assistant Examiner*—Tamthom N. Truong
(74) *Attorney, Agent, or Firm*—Woodcock Washburn Kurtz Mackiewicz & Norris LLP

(57) ABSTRACT

Propanoic acid derivatives of formula (1) are described:

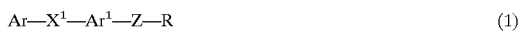

Ar—X$^1$—Ar$^1$—Z—R   (1)

in which

Ar is a nitrogen base containing group;

X$^1$ is linker atom or group;

Ar$^1$ is an optionally substituted 5- or 6-membered nitrogen-containing aromatic or non-aromatic monocycle;

Z is a group —CH(R$^{13}$)CH$_2$— [in which R$^{13}$ is an optionally substituted aliphatic, cycloaliphatic, heteroaliphatic, heterocycloaliphatic, aromatic or heteroaromatic group], —C(R$^{12a}$)(R$^{13}$)—CH(R$^{12b}$)— [in which R$^{12a}$ and R$^{12b}$ together with the carbon atoms to which they are attached form a C$_{3-7}$cycloalkyl group] or C(R$^{13}$)=CH—;

R is a carboxylic acid (—CO$_2$H) or a derivative or biostere thereof; and the salts, solvates, hydrates and N-oxides thereof. The compounds are able to inhibit the binding of α$_V$ integrins to their ligands and are of use in the prophylaxis and treatment of immune or inflammatory disorders.

15 Claims, No Drawings

U.S. PATENT DOCUMENTS

| | | |
|---|---|---|
| WO 94/15954 | 7/1994 | (WO) . |
| WO 94/15955 | 7/1994 | (WO) . |
| WO 94/29285 | 12/1994 | (WO) . |
| WO 95/13811 | 5/1995 | (WO) . |
| WO 95/15973 | 6/1995 | (WO) . |
| WO 95/19356 | 7/1995 | (WO) . |
| WO 95/35314 | 12/1995 | (WO) . |
| WO 96/01644 | 1/1996 | (WO) . |
| WO 96/22966 | 8/1996 | (WO) . |
| WO 96/26190 | 8/1996 | (WO) . |
| WO 97/03094 | 1/1997 | (WO) . |
| WO 97/08145 | 3/1997 | (WO) . |
| WO 97/12866 | 4/1997 | (WO) . |
| WO 97/31907 | 9/1997 | (WO) . |
| WO 97/36859 | 10/1997 | (WO) . |
| WO 98/00395 | 1/1998 | (WO) . |
| WO 98/04247 | 2/1998 | (WO) . |
| WO 98/04913 | 2/1998 | (WO) . |
| WO 98/42662 | 10/1998 | (WO) . |
| WO 98/53814 | 12/1998 | (WO) . |
| WO 98/53817 | 12/1998 | (WO) . |
| WO 98/53818 | 12/1998 | (WO) . |
| WO 98/54207 | 12/1998 | (WO) . |
| WO 98/58902 | 12/1998 | (WO) . |
| WO 99/06390 | 2/1999 | (WO) . |
| WO 99/06431 | 2/1999 | (WO) . |
| WO 99/06432 | 2/1999 | (WO) . |
| WO 99/06433 | 2/1999 | (WO) . |
| WO 99/06434 | 2/1999 | (WO) . |
| WO 99/06435 | 2/1999 | (WO) . |
| WO 99/06436 | 2/1999 | (WO) . |
| WO 99/06437 | 2/1999 | (WO) . |
| WO 99/10312 | 3/1999 | (WO) . |
| WO 99/10313 | 3/1999 | (WO) . |
| WO 99/20272 | 4/1999 | (WO) . |
| WO 99/35163 | 7/1999 | (WO) . |
| WO 99/37618 | 7/1999 | (WO) . |
| WO 99/43642 | 9/1999 | (WO) . |
| WO 99/48879 | 9/1999 | (WO) . |

OTHER PUBLICATIONS

Hammes, H., et al., "Subcutaneous injection of a cyclic peptide antagonist of vitronectin receptor–type integrins inhibits retinal neovascularization," *Nature Medicine*, 1996, 2, 529–533.

Hodivala–Dilke, K.M., "β3–integrin–deficient mice are a model for glanzmann thrombasthenia showing placental defects and reduced survival," *J. Clin. Invest.*, 1999, 103(2), 229–238.

Kalvin, D.M., et al., Synthesis of (4R)–D,L–[4–$^2$H]– and (4S)–D,L–[4–$^2$H] homoserine lactones, *J. Org. Chem.*, 1985, 50, 2259–2263.

Koivunen, E., et al., "Selection of peptides binding to the $\alpha_5\beta_1$ integrin from phage display library," *J. Biological Chemistry*, 1993, 268(27), 20205–20210.

Mitjans, F., et al., "An anti–αv–integrin antibody that blocks integrin function inhibits the development of a human melanoma in nude mice," *J. Cell Science*, 1995, 108, 2825–2838.

Molina, P., et al., "Iminophosphorane–mediated annelation of a pyridine ring into a preformed pyridine one: synthesis of napthyridine, pyrido [1,2–c] pyrimidine and pyrido [1,2–c] quinazoline derivatives," *Tetrahedron*, 1992, 48(22), 4601–4616.

Newham, P., et al., "Integrin adhesion receptors: structure, function, and implications for biomedicine," *Nolecular Medicine Today*, 1996, 304–313.

Numata, A., et al., "General synthetic method for napthyridines and their N–oxides containing isoquinolinic nitrogen," *Synthesis*, 1999, 2, 306–311.

Rico, J.G., et al., "A highly steroselective michael addition to an αβ–unsaturated ester as the crucial step in the synthesis of a novel β–amino acid–containing fibrinogen receptor antagonist," *J. Org. Chem.*, 1993, 58, 7948–7951.

Sakamoto, T., et al., "Condensed heteroaromatic ring systems. III. synthesis of naphthyridine derivatives by cyclization of ethynylpyridinecarboxamides," *Chem. Pharm. Bull.* 1985, 33(2), 626–633.

Singh, G., et al., "Prodrug approach in new drug design and development," *J. Sci. Ind. Res.*, 1996, 55, 497–510.

Srivatsa, S.S., et al., "Selective αvβ3 integrin blockade potently limits neointimal hyperplasia and lumen stenosis following deep coronary arterial stent injury: evidence for the functional importance of integrin αvβ3 and osteopontin expression during neointima formation," *Cariovascular Research*, 1997, 36, 408–428.

Stupack, D.G., et al., "induction of $\alpha_\nu\beta_3$ integrin–mediated attachment to extracellular matrix in $\beta_1$ integrin (CD29)–negative B cell lines," *Experi. Cell Research*, 1992, 203, 443–448.

Tan, R., et al., "Synthesis of 2,6–naphthyridine and some of its derivatives," *Tetrahedron Letters*, 1965, 31, 2737–2744.

Zablocki, J.A., "Potent in vitro and in vivo inhibitors of platelet aggregation based upon the arg–gly–asp sequence of fibrinogen. (Amimobenzamidino)succinyl (ABAS) series of orally active fibrinogen receptor antagonists," *J. Med. Chem.*, 1995, 38, 2378–2394.

Hammadi, A., et al., "Diastereoselective hydrogenation of monodehydro enkephalins controlled by chiral rhodium catalysts," *Tetrahedron Assymmetry*, 1992, 3(10), XP002106601, 1247–1262.

Nunami, K., et al., "A novel synthesis of methyl 1,5–disubstituted imidazole–4–carboxylates using 3–bromo–2–isocyanoacrylates," *J. Org. Chem.*, 1994, 59, XP002106602, 7635–7642.

Shimohigashi, Y., et al., "Dehydro–enkaphalins," *Int. J. Peptide Protein Res.*, 1983, 21, XP002106600, 202–208.

Strange, P.G., et al., "Studies of enzyme–mediated reactions. Part II. Stereochemistry of the elimination of ammonia form L–tyrosine catalysed by the enzyme from maize," *J. Chem. Soc. Perkin I*, 1972, 18, XP002106603, 2364–2372.

WPI/Derwent No. XP002106604, Japanese Patent No. JP 60 190749 (Mitsui Toatsu Chem. Inc.), Sep. 28, 1985, 1 page, Abstract only.

Lobb, R.R., et al., "Small molecule antagonists of alpha4 integrins: novel drugs for asthma," *Exp. Opin, Invest. Drugs*, 1999, XP000885957, 8(7), 935–945.

Samanen, J., et al., "Vascular indications for integrin alpha V antagonists," *Current Pharm. Design.*, 1997, 3, 545–584.

Švrda, J., "CIS–TRANS isomerism of N–ACYL derivatives of proline and its analogues, linear peptides with CIS peptide bonds," Proc. 14$^{th}$ European Peptide Symposium, Loffet, A. (ed.), 1976, 653–656.

Clausen, K., et al., "Studies on amino acids and peptides. II. Synthesis of protected endothiodipeptides," *J. Chem. Scr.*, 1982, 20(1–2), 14–18, doc. No. 97:163474 (abstract only, 1 page).

Frank, R., et al., "Extremely mild reagent for Boc deprotection," *J. Chem. Commun., (Cambridge)*, 1996, 22, 2509–2510, doc. No. 126:104395 (abstract only, 3 pages).

Kobayashi, A., et al., "Synthesis of 2–dialkylamino–4,4–disubstituted 5 (4H)–thiazolones," *J. Yakugaku Zasshi*, 1970, 90(11), 1377–1380, doc. No. 74:31713 (abstract only, 3 pages).

Koenig, H.B., et al., ".beta.–Lactam antibiotics," *Ger. Offen.*, 41 pages, doc. No. 83:97276 (abstract only, 5 pages), 1975.

Masuda, T., *Jpn. Kodai Tokkyo Koho*, 22 pages, doc No. 115:280022 (abstract only, 1 page), 1991.

Pfeifer, T., et al., "Specific fragmentation of thioxo peptides facilitates the assignment of the thioxylated amino acid," *J. Mass Spectrum*, 1997, 32(10), 1064–1071, doc No. 127:331738 (abstract only 2 pages).

Sawa, N., et al., "Preparation of 4(5)–thiocarbamoylimidazole compounds," *Jpn. Kokai Tokkyo Koho*, 33 pages, doc No. 115:183296 (abstract only, 2 pages), 1991.

Schutkowski, M., et al., "Inhibition of peptidyl–prolyl cis/trans isomerase activity by substrate analog structures: thioxo tetrapeptide–4–nitroanilides," *Biochemistry*, 1995, 34(40), 13016–13026, doc. No. 123:221511 (abstract only, 4 pages).

Toyama Chem. Co., "Cephalosporins," *Jpn. Kokai Tokkyo Koho*, 40 pages, doc. No. 99:5433 (abstract only, 2 pages), 1983.

Azzouny, A.E., et al., "Synthesis of some N–substituted salicylamides structurally related to certain antimicrobials," *Pharmazie*, 1977, 32(6), 318–323 (abstract).

Badshah, A., et al., "Catalytic reduction of azlactones in alkaline media. Synthesis of amino acids," *J. of Organic Chemistry*, 1972, 37(18), 2916–2918.

Tous, G., et al., "O'–(Epoxyalkyl) tyrosines and (Expoxyalkyl) phenylalanine as irreversible inactivators of serine proteases: synthesis and inhibition mechanism," *J. of Medicinal Chemistry*, 1990, 33(6), 1620–1634.

Abraham, W.M. et al., "$\alpha_4$–Integrins Mediate Antigen–Induced Late Bronchial Responses and Prolonged Airway Hyperresponsiveness in Sheep," *J. Clin. Invest.*, 1994, 93, 776–787.

Bach et al., "Anomalous optical rotation and circular dichroism of N–thioacylated.alpha.–amino acids and deriva," *Acta Chem. Scand.*, 1966, 20(10), 2781–2794.

Barrett, G.C., "Circular dichroism of N–thiobenzoyl–1–$\alpha$–amino acids. III. Their circular dichroism through the near–ultraviolet wavelength range," *J. Chem. Soc.*, 1967, Section C, 1–5.

Berlin, C. et al., "$\alpha4\beta7$ Integrin Mediates Lymphocyte Binding to the Mucosal Vascular Addressin MAdCAM–1," *Cell*, 1993, 74, 185–195.

Binns, R.M. et al., "The Role of E–Selectin in Lymphocyte and Polymorphonuclear Cell Recruitment into Cutaneous Delayed Hypersensitivity Reactions in Sensitized Pigs," *J. Immunol.*, 1996, 157, 4094–4099.

Briskin, M.J. et al., "Structural Requirements for Mucosal Vascular Addressin Binding to Its Lymphocyte Receptor $\alpha_4\beta_7$," *J. Immunol.*, 1996, 156, 719–726.

Cardarelli, P.M. et al., "Cyclic RGD Peptide Inhibits $\alpha4\beta7$ Interaction with Connecting Segment 1 and Vascular Cell Adhesion Molecule," *J. Biol. Chem.*, 1994, 269(28), 18668–18673.

Dainippon Pharmaceutical Co., Ltd., *Chemical Abstracts*, "N–[4–Thiazolidinyl)carbonyl]amino acid derivatives," 1981, 95(19), Abstract No. 169173f, 1 page.

Corey, E.J. et al., "A Synthetic Method for Formyl→Ethynyl Conversion (RCHO→RC≡CH or RC≡CR')," *Tetrahedron Lett.*, 1972, 36, 3769–3772.

Cornforth, J.W., "Oxazoles and Oxazolones," *Chem. Penicillin*, Princeton Book Review, 1949, pp. 688, 799, and 800.

Ferguson, T.A. et al., "Two integrin–binding peptides abrogate T cell–mediated immune responses in vivo," *Proc. Natl. Acad. Sci. USA*, 1991, 88, 8072–8076.

Fu, H. et al., "Preliminary study on synthesis and antitumor activity in vitro of derivatives of timonacic," *Chemical Abstracts*, 1988, 108(17), Abstract No. 150358k, 1 page.

Harris, R.L.N. et al., *Aust. J. Chem.*, "Potential wool growth inhibitors. 2(1H)–Pyridone analogs of mimosine," 1977, 30(3), 649–655.

Hartke, K. et al., "Dithio and thiono esters. Part 61. Synthesis of $\alpha$–amino dithioesters and endothiodipeptides," *J. Prakt. Chem.*, 1996, 338(3), 251–256.

Holzmann, B. et al., "Peyer's patch–specific lymphocyte homing receptors consist of a VLA–4–like $\alpha$ chain associated with either of two integrin $\beta$ chains, one of which is novel," *EMBO J.*, 1989, 8(6), 1735–1741.

Humphries, M.J. et al.,"Mechanisms of VCAM–1 and fibronectin binding to integrin $\alpha_4\beta_1$:implications for integrin function and rational drug design," Ciba Foundation Symposium, 1995, 189, 177–194.

Issekutz, T.B., "Inhibition of Lymphocyte Endothelial Adhesion and In Vivo Lymphocyte Migration to Cutaneous Inflammation by TA–3, a New Monoclonal Antibody to Rat LFA–1," *J. Immunol.*, 1992, 149(10), 3394–3402.

Jaynes, B.H. et al., "Synthesis and In Vivo Antibacterial Activity of Hygromycin a Analogs Modified at the $C_4$' Aryl Position," *Bioorg. Med. Chem. Letts.*, 1993, 3(8), 1531–1536.

Jepson, J.B. et al., "Reactions of $\alpha$–Thioacylamino–acids. Their conversion into Thiazolones and Derivatives Thereof," *J. Chem. Soc.*, 1955, 1791–1797.

Lei, H. et al., "Efficient Synthesis of a Phosphinate Bis–Amino Acid and Its Use in the Construction of Amphiphilic Peptides," *J. Org. Chem.*, 1994, 59, 4206–4210.

Li, Z. et al., "Effect of an anti–Mo1 MAb on ozone–induced airway inflammation and airway hyperresponsiveness in dogs," *Am. J. Physiol.*, 1992, 263(6 Pt.1), L723–726.

Marlin, S.D. et al., "LFA–1 Immunodeficiency Disease," *J. Exp. Med.*, 1986, 164, 855–867.

Masahiko, N., Japanese Patent No. 57–080370 published May 19, 1982, "Alpha–Methylcinnamic Acid Derivative, its Preparation and Antilipemic Agent Containing The Same," *Patent Abstracts of Japan*, 1982, 1 page.

Nagasawa, H.T. et al., "$\beta$–Substituted Cysteines as Sequestering Agents for Ethanol–Derived Acetaldehyde in Vivo," *J. Med. Chem.*, 1987, 30, 1373–1378.

Noike, Y., "Synthesis of Quinolizine Derivatives. VI. Synthesis of 3–Aminoquinolizines. (1). Synthesis of dl–3–Amino–, dl–3–epi–Amino–, and dl–3–epi–Dimethylaminoquinolizidines," *Yakugaku Zasshi*, 1959, 79(12), 1514–1518 (English summary included).

Ohki, S. et al.,"Synthesis of quinolizine derivatives. V. Studies on Diastereoisomer of Ethyl 3–Quinolizidinecarboxylate," *Chem. Pharm. Bull.*, 1959, 7(6), 708–712.

Osborne, L., "Leukocyte Adhesion to Endothelium in Inflammation," *Cell*, 1990, 62, 3–6.

Osborn, L. et al., "Direct Expression Cloning of Vascular Cell Adhesion Molecule 1, a Cytokine–Induced Endothelial Protein that Binds to Lymphocytes," *Cell,* 1989, 59, 1203–1211.

Podolsky, D.K. et al., "Attenuation of Colitis in the Cotton–top Tamarin by Anti–α4 integrin Monoclonal Antibody," *J. Clin. Invest.,* 1993, 92, 372–380.

Schultz, Von O.–E. et al., "Analogos of nuleic acid based as antimetabolites," *Arzneimittel Forschung. Drug Res.,* 1967, 17(8), 1060–1064 (English summary included).

Shroff, H.N. et al., "Small Peptide Inhibitors of $\alpha_4\beta_7$ Mediated MAdCAM–1 Adhesion to Lymphocytes," *Barge. Med. Chem. Letts.,* 1996, 6(21), 2495–2500.

Sonnenberg, A., "Integrins and Their Ligands," *Curr. Topics Microbiol. Immunol.,* 1993, 184, 7–35.

Springer, T.A., "Adhesion receptors of the immune system," *Nature,* 1990, 346, 425–434.

Springer, T.A., "Traffic Signals for Lymphocyte Recirculation and Leukocyte Emigration: The Multistep Paradigm," *Cell,* 1994, 76, 301–314.

Tsunematsu, H. et al., "Hydrolysis of phenylthiazolones of p–guanidinophenylalanine and arginine by trypsin and related enzymes," *J. Biochem.,* 1983, 94(4), 1119–1125.

Vanderslice, P. et al., "A Cyclic Hexapeptide is a Potent Antagonist of α4 Integrins," *J. Immunol.,* 1997, 158, 1710–1718.

Yanagisawa, H. et al., WO 97/37970, "Preparation of phenylalkylcarboxylic acid derivatives lowering blood sugar level," *Chemical Abstracts,* 1997, Abstract 127:307307, 4 pages.

Yang, X., "A predominant role of integrin α4 in the spontaneous development of autoimmune diabetes in nonobese diabetic mice," *Proc. Natl. Acad. Sci. USA,* 1994, 91, 12604–12608.

Yednock, T.A., "Prevention of experimental autoimmune encephalomyelitis by antibodies against α4β1 integrin," *Nature,* 1992, 356, 63–66.

Whitlock, B.J. et al., "Structure and synthesis of lathyrine," *J. Org. Chem.,* 1965, 30, 115–118.

WPI/Derwent No. XP–002076854, Japanese Patent No. JP 04 193 895 A (Ajinomoto, K.K.), Jul. 13, 1992, DW9234, 1 Page, Abstract Only.

WPI/Derwent No. XP–002076855, Japanese Patent No. JP 56 049 373 A (Dainippon Pharm Co Ltd), May 2, 1981, DW8125, 1 Page, Abstract Only.

Buckle, D.R., et al., "Non Thiazolidinedione Antihyperglycaemic Agents. 1: α–Heteroatom Substituted β–Phenylpropanoic Acids," *Bioorg. Med. Chem. Lett.,* 1996, 6(17), 2121–2126.

Keenan, R.M. et al., "Discovery of Potent Nonpeptide Vitronectin Receptor (av$\beta_3$) Antagonists," *J. Med. Chem.,* 1997, 40(15), 2289–2292.

McDowell, R.S. et al., "From Peptide to Non–Peptide. 2. The de Novo Design of Potent, Non–Peptidal Inhibitors of Platelet Aggregation Based on a Benzodiazepinedione Scaffold," *J. Am. Chem. Soc.,* 1994, 116, 5077–5083.

Miller, W.H. et al., "Structure–Activity Relationships in 3–Oxo–1,4–Benzodiazepine–2–Acetic Acid GPIIb/IIIa Antagonists. The 2–Benzazepine Series," *Bioorg. Med. Chem. Lett.,* 1996, 6(21), 2481–2486.

Ukai, Y. et al., "A novel synthetic inhibitor of endopeptidase–24.15," *Chemical Abstracts,* 1997, 127(2), 1 page.

Venturella, V.S. et al., "Substituted 1,3–Dihydro–4H–furo [3,4–d]–1,3–benzodiazepin–3–ones: Synthesis and Scope of the Method," *J. Heterocyclic Chem.,* 1969, 6(5), 671–679.

Wojciechowska, H. et al., "Preparation of 2,4–dinitrophenyl derivatives of tyrosine," *Chemical Abstracts,* 1968, 68(25), Abstract No. 11492r, 1 page.

* cited by examiner

PROPANOIC ACID DERIVATIVES

This invention relates to a series of propanoic acid derivatives, to compositions containing them, to processes for their preparation and to their use in medicine.

Over the last few years it has become increasingly clear that the physical interaction of a cell with other cells or components of the extracellular matrix plays an important role in regulating its response to external stimuli such as chemotactic factors, growth factors, cytokines, and inflammatory mediators [Juliano and Haskill, J. Cell Biol. 1 577–585 (1993); Miyamoto et al J. Cell Biol. 135, 1633–1642 (1996)]. Furthermore, the physical attachment of cells to other cells or surfaces may be crucial for development of some normal physiological responses.

In many disease states normal physiological responses are inappropriately triggered and are detrimental to the well being of the host. Since adhesion molecules play a role in the physical interactions of cells, antagonists of adhesion molecules may be able to inhibit some of the detrimental biological responses found in many disease states.

The adhesion molecules have been sub-divided into different groups on the basis of their structure. One family of adhesion molecules which is believed to play a particularly important role in informing a cell about the nature of its extracellular environment is the integrin family. Members of this family are involved in helping to regulate processes such as proliferation, apoptosis, migration and gene expression in a range of different cell types. They have also been shown to play a key role in regulating immune and inflammatory responses.

The integrin family of cell surface adhesion molecules has a typical non-covalently linked heterodimer structure. At least 14 different integrin alpha chains and 8 different integrin beta chains have been identified [Sonnenberg A Current Topics in Microbiology and Immunology, 184 (1993)]. The members of the family are typically named according to their heterodimer composition although trivial nomenclature is widespread in this field. Thus the integrin $\alpha_v\beta_3$ consists of the alpha v chain non-covalently linked to the beta 3 chain.

Some integrin chains are capable of pairing with more than one partner. For example, the alpha v chain has also been reported to pair with the beta 1 chain, the beta 5 chain, the beta 6 chain and the beta 8 chain to give molecules which bind to different sets of ligands and which are referred to respectively as the integrins $\alpha_v\beta_1$, $\alpha_v\beta_5$, $\alpha_v\beta_6$ and $\alpha_v\beta_8$.

Integrins containing the $\alpha_v$ subunit form a family of integrins which generally (but not always) bind to vitronectin although several of them will bind to a range of other matrix molecules and/or cell surface molecules. For example $\alpha_v\beta_3$ will bind to molecules such as vitronectin, fibronectin, fibrinogen, osteopontin, bone sialoprotein, thrombospondin, pro von Willebrand factor and CD31.

The importance of integrin function in normal physiological responses is highlighted by two human deficiency diseases in which integrin function is defective. Thus, in the disease termed Leukocyte Adhesion Deficiency (LAD) there is a defect in one of the families of integrins expressed on leukocytes. Patients suffering from this diesease show a dramatically reduced ability to recruit leukocytes to inflammatory sites. In the case of patients suffering from the disease termed Glanzman's thrombasthenia (a defect in a member of the beta 3 integrin family) there is a defect in blood clotting.

The interaction of cells with components of the extracellular environment via receptors containing $\alpha_v$ has been reported to be involved in a number of cellular responses which may be important in human disease states. These include endothelial cell proliferation and angiogenesis [Friedlander M, et al, Science 270, 1500–1502 (1995)], coronary smooth muscle cell migration, proliferation and extracellular matrix invasion [Panda, D., PNAS, 94, 9308–9313 (1997)], regulation of other integrin molecules on different cell types [Blystone, S D. J. Cell Biol. 127, 1129–1137 (1994); Imhof, B. Eur. J. Immunol, 27, 3242–3252 (1997)] and bone resorption [Ross F. P. et al, J. Biol. Chem. 268 9901–9907 (1993)]. Furthermore, the $\alpha_v$ receptor has been reported to bind to the protease MMP-2 and this may also modify cell function [Brooks P.C. et al, Cell, 92, 391–400 (1998)].

Monoclonal antibodies and peptides have also been used to demonstrate in animal models that potentially beneficial changes in physiology can be achieved by blocking the function of $\alpha_v$-containing integrin receptors. For example, Mitjans F. et al [Journal of Cell Science, 108, 2825–2838 (1995)] showed that in a mouse model an antibody that bound to the $\alpha_v$ chain inhibited tumour development and metastasis. Brooks P.C., et al; [J. Clin. Invest. 96, 1815–1822 (1995)] demonstrated that an antibody that blocked the function of $\alpha_v\beta_3$ inhibited the growth of a tumour implanted into a piece of human skin grafted on to a SCID mouse. Christofidou-Solomidou M, [Am. J. Pathol. 151, 975–983 (1997)] has reported that an anti-$\alpha_v$ monoclonal antibody inhibited angiogenesis at the site of wound healing. Hammes H-P, et al, [Nature Medicine, 2, 529–533 (1996)] showed that an $\alpha_v$ integrin antagonist cyclic peptide inhibited retinal neovascularisation in a model which may have relevance to the human disease states of retinopathy and senile macular degeneration. Srivata S, et al [Cardiovascular Research 36 408–428 (1997)] have reported that in an animal model a peptidic $\alpha_v\beta_3$ antagonist can limit neointimal hyperplasia and luminal stenosis.

$\alpha_v\beta_3$ has been reported to bind to a molecule expressed on endothelial cells termed CD31 [Piali L. et al, J. Cell Biol. 130, 451–460 (1995)]. Thus $\alpha_v\beta_3$ may play a role in leukocyte extravasation. It has also been shown to be capable of co-stimulating T-cell degranulation [Ybarrondo B. Immunology, 91, 186–192 (1997)]. Inhibition of $\alpha_v$ function may down regulate immune and/or inflammatory responses.

$\alpha_v\beta_3$ has also been shown to play a role in the ingestion of apoptotic cells by macrophages [Akbar A. N. et al, J. Exp. Med 180, 1943–1947 (1994)]. The rapid phagocytosis of apoptotic cells may be a physiological method of reducing inflammatory responses associated with cell lysis. The modulation of $\alpha_v\beta_3$ function may alter the inflammatory responses mounted in regions of apoptosis. In some disease states this may be beneficial.

It has also been shown that members of the $\alpha_v$ family play a key role in the ability of osteoclasts to resorb bone. An imbalance between bone formation and resorption can lead to major health problems. Blockade of $\alpha_v$ containing receptors can inhibit bone resorption in an animal model [Engleman V. W. et al J. Clin. Invest. 99, 2284–2292, (1997)] and this suggests that $\alpha_v$ antagonists may be useful in the treatment of human diseases such as osteoporosis, Paget's disease, humoral hypercalcaemia of malignancy and metastic bone disease.

$\alpha_v$ containing receptors are often upregulated at sites of angiogenesis where this occurs for example in tumours, and some pathological conditions. Arap W, et al [Science, 279, 377–380, (1998)] have shown that peptides that bind to $\alpha_v$ containing receptors can be used to deliver drugs to such sites and an antibody recognising an α$_v$ integrin has been shown to be capable of imaging tumour vasculature [Sipkins D. A. et al Nature Medicine, 4, 623–626 (1998].

The tissue distribution and range of ligands of different members of the α$_v$ integrin family suggests that these molecules may have different physiological roles. This view is supported by Friedlander M et al [Science, 27, 1500–1502, (1995)] who showed that angiogenesis associated with different growth factors was dependent on different α$_v$ containing integrins.

Inhibition of an α$_v$-mediated cell interaction can be expected to be beneficial in a number of disease states. However, because of the ubiquitous distribution and wide range of functions performed by other members of the integrin family it is important to be able to identify selective inhibitors of the α$_v$subgroup.

We have now found a group of compounds which are potent and selective inhibitors of α$_v$integrins. Members of the group are able to inhibit α$_v$ integrins such as α$_v$β$_3$ and/or α$_v$β$_5$ at concentrations at which they generally have no or minimal inhibitory action on integrins of other subgroups. The compounds are thus of use in medicine, for example in the prophylaxis and treatment of diseases or disorders involving inappropriate growth or migration of cells as described hereinafter.

Thus according to one aspect of the invention we provide a compound of formula (1):

$$\text{Ar—X}^1\text{—Ar}^1\text{—Z—R} \qquad (1)$$

wherein:
(1) Ar is a group R$^{1a}$N(R$^2$)L$^1$Ar$^2$— in which:
R$^{1a}$N(R$^2$) is a nitrogen base;
L$^1$ is a —C(R$^3$)(R$^4$)— [where R$^3$ and R$^4$, which may be the same or different, is each a hydrogen atom, a straight or branched alkyl group or a hydroxyl group], —C(O)—, —C(S)—, —S(O)—, —S(O)$_2$—, —P(O)—, —P(O)(OR$^a$)— [where R$^a$ is a hydrogen atom or a straight or branched C$_{1-6}$alkyl group] or —P(O)(OR$^a$)O— group; and
Ar$^2$ is an optionally substituted six-membered 1,4-arylene or 1,4-heteroarylene ring; or
(2) Ar is a group R$^{1b}$Ar$^2$ in which R$^{1b}$ is a cyclic or acyclic nitrogen base and Ar$^2$ is as just defined; or
(3) Ar is a bicyclic ring:

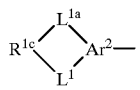

in which R$^{1c}$ is a nitrogen base, L$^1$ and Ar$^2$ are as just defined and —L$^{1a}$— is a covalent bond a —(CH$_2$)$_2$— or —(CH$_2$)$_3$— group or a group L$^1$ as just defined; or
(4) Ar is a group R$^{1d}$L$^1$Ar$^2$— in which R$^{1d}$ is a nitrogen base and L$^1$ and Ar$^2$ as just defined;
X$^1$ is an —O— or —S—O atom or a group selected from —C(O)—, —C(S)—, —S(O)—, —S(O)$_2$—, —C(R$^5$)(R$^6$)— {where R$^5$ is a hydrogen atom or an optionally substituted straight or branched alkyl group and R$^6$ is a hydrogen or halogen atom or a straight or branched alkyl, haloalkyl, alkoxy, haloalkoxy, alkylthio, aromatic, heteroaromatic, or —(Alk$^1$)$_m$R$^7$ group [in which Alk$^1$ is a C$_{1-3}$alkylene chain, m is zero or the integer 1 and R$^7$ is a —OH, —SH, —NO$_2$, —CN, —CO$_2$H, —CO$_2$R$^8$ (where R$^8$ is an optionally substituted straight or branched C$_{1-6}$alkyl group), —SO$_3$H, —SOR$^8$, —SO$_2$R$^8$, —OCO$_2$R$^8$, C(O)H, —C(O)R$^8$, —OC(O)R$^8$, —C(S)R$^8$, —NR$^9$R$^{10}$ (where R$^9$ and R$^{10}$, which may be the same or different is each a hydrogen atom or a straight or branched alkyl group), —C(O)N(R$^9$)(R$^{10}$), —OC(O)N(R$^9$)(R$^{10}$), —N(R$^9$)C(O)R$^{10}$, —CSN(R$^9$)(R$^{10}$), —N(R$^9$)C(S)R$^{10}$, —SO$_2$N(R$^9$)(R$^{10}$), —N(R$^9$)SO$_2$R$^{10}$, —N(R$^9$)C(O)N(R$^{10}$)(R$^{11}$) [where R$^{11}$ is a hydrogen atom or a straight or branched alkyl group], —N(R$^9$)C(S)N(R$^{10}$)(R$^{11}$), —N(R$^9$)SO$_2$N(R$^{10}$)(R$^{11}$), aromatic or hetero-aromatic group} or —N(R$^5$)—;
Z is a group —CH(R$^{13}$)CH$_2$— [in which R$^{13}$ is an optionally substituted aliphatic, cycloaliphatic, heteroaliphatic, heterocycloaliphatic, aromatic or heteroaromatic group], —C(R$^{12a}$)(R$^{13}$)—CH (R$^{12b}$)— [in which R$^{12a}$ and R$^{12b}$ together with the carbon atoms to which they are attached form a C$_{3-7}$cycloalkyl group] or —C(R$^{13}$)=CH—;
R is a carboxylic acid (—CO$_2$H) or a derivative or biostere thereof;
Ar$^1$ is an optionally substituted 5- or 6-membered nitrogen-containing aromatic or non-aromatic monocycle selected from:

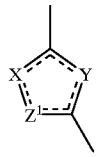
(A)

where one of X and Y is a nitrogen atom and the other is a nitrogen, oxygen or sulphur atom, Z$^1$ is a carbon, nitrogen, oxygen or sulphur atom and the broken line (- -) represents saturation or unsaturation; or

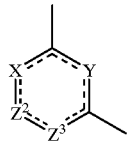
(B)

where X, Y and the broken line are as just defined and Z$^2$ and Z$^3$ is each a carbon, nitrogen, oxygen or sulphur atom;
and the salts, solvates, hydrates and N-oxides thereof.

It will be appreciated that certain compounds of formula (1) may exist as geometric isomers (E or Z isomers). The compounds may also have one or more chiral centres, and exist as enantiomers or diastereomers. The invention is to be understood to extend to all such geometric isomers, enantiomers, diastereomers and mixtures thereof, including racemates. Formula (1) and the formulae hereinafter are intended to represent all individual isomers and mixtures thereof, unless stated or shown otherwise.

In the compounds of the invention as represented by formula (1) and the more detailed description hereinafter certain of the general terms used in relation to substituents are to be understood to include the following atoms or groups unless specified otherwise.

Thus as used herein the term "optionally substituted straight or branched alkyl", whether present as a group or part of a group includes optionally substituted straight or branched $C_{1-6}$alkyl groups, for example $C_{1-4}$alkyl groups such as methyl, ethyl, n-propyl, i-propyl or t-butyl groups. Similarly, the terms "optionally substituted straight or branched alkenyl" or "optionally substituted straight or branched alkynyl" are intended to mean $C_{2-6}$alkenyl or $C_{2-6}$alkynyl groups such as $C_{2-4}$alkenyl or $C_{2-4}$alkynyl groups. Optional substitutents present on these groups include those optional substituents mentioned hereinafter in relation to $R^2$ optionally substituted aliphatic groups.

The term "halogen atom" is intended to include fluorine, chlorine, bromine or iodine atoms.

The term "straight or branched haloalkyl" is intended to include the alkyl groups just mentioned substituted by one, two or three of the halogen atoms just described. Particular examples of such groups include —$CF_3$, —$CCl_3$, —$CHF_2$— —$CHCl_2$, —$CH_2F$, and —$CH_2Cl$ groups.

The term "straight or branched alkoxy" as used herein is intended to include straight or branched $C_{1-6}$alkoxy e.g. $C_{1-4}$alkoxy such as methoxy, ethoxy, n-propoxy, i-propoxy and t-butoxy. "Haloalkoxy" as used herein includes any of those alkoxy groups substituent by one, two or three halogen atoms as described above. Particular examples include —$OCF_3$, —$OCCl_3$, —$OCHF2$, —$OCHCl_2$, —$OCH_2F$ and —$OCH_2Cl$ groups.

As used herein the term "straight or branched alkylthio" is intended to include straight or branched $C_{1-6}$alkylthio, e.g. $C_{1-4}$alkylthio such as methylthio or ethylthio groups.

The terms "aromatic" or heteroaromatic" are intended to include those optionally substituted aromatic or heteroaromatic groups described generally and particularly hereinafter in relation to the groups $R^2$, $R^{14}$, $R^{15}$ and $R^{16}$.

Where the term "1,4-arylene" is used in relation to $Ar^2$ in the formulae herein this is to be understood to mean a ring:

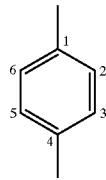

in which the carbon atoms at the one and four positions are attached to the remainder of the molecule. The term "1,4-heteroarylene" is to be understood to mean an equivalent ring structure in which one or more of the carbon atoms at the 2-, 3-, 5- and/or 6-positions of the 1,4-arylene ring is replaced by a nitrogen atom.

Such arylene and heteroarylene rings may be optionally substituted, each substituent being attached to a carbon atom, where present, at the 2-, 3-, 5- and/or 6-positions. Particular substituents include halogen atoms, or straight or branched alkyl, haloalkyl, alkoxy, haloalkoxy or alkylthio groups, or —OH, —$CO_2H$, —$CO_2R^8$, —CN, —$NH_2$, —$NO_2$ or straight or branched alkylamino or dialkylamino groups.

Nitrogen bases represented by the group $R^{1a}N(R^2)$— in compounds of the invention include acyclic or cyclic nitrogen bases containing two, three or more nitrogen atoms. Such bases will generally include one or more carbon atoms and optionally one or more other heteroatoms such as oxygen or suphur atoms.

Particular examples of acyclic nitrogen bases represented by the group $R^{1a}N(R^2)$— include those wherein $R^{1a}$ is a $R^{14}R^{15}NC(X^2)$— or $R^{15}C(=NR^{14})$— group, in which $X^2$ is a =$NR^{16}$, =O, =NCN, =NC(O)$NH_2$ or =S group, and each of $R^2$, $R^{14}$, $R^{15}$ and $R^{16}$, which may be the same or different, is a hydrogen atom or an optionally substituted aliphatic, heteroaliphatic, cycloaliphatic, polycycloaliphatic, heterocycloaliphatic, heteropolycycloaliphatic, aromatic or heteroaromatic group.

Optionally substituted aliphatic groups represented by $R^2$, $R^{14}$, $R^{15}$ and/or $R^{16}$ in the bases $R^{1a}N(R^2)$— include optionally substituted $C_{1-10}$ aliphatic groups. Particular examples include optionally substituted straight or branched $C_{1-10}$alkyl, e.g. $C_{1-6}$alkyl, $C_{2-10}$alkenyl, e.g. $C_{2-6}$alkenyl or $C_{2-10}$alkynyl e.g. $C_{2-6}$alkynyl groups.

Heteroaliphatic groups represented by $R^2$, $R^{14}$, $R^{15}$ and/or $R^{16}$ include the aliphatic groups just described but with each group additionally containing one, two, three or four heteroatoms or heteroatom-containing groups. Particular heteroatoms or groups include atoms or groups $L^2$ where $L^2$ is a linker atom or group. Each $L^2$ atom or group may interrupt the aliphatic group, or may be positioned at its terminal carbon atom to connect the group to an adjoining atom or group. Particular examples of suitable $L^2$ atoms or groups include —O— or —S— atoms or —C(O)—, —C(O)O—, —C(S)—, —S(O)—, —S(O)$_2$—, —N($R^{17}$)— [where $R^{17}$ is a hydrogen atom or an optionally substituted straight or branched alkyl group], —CON($R^{17}$)—, —OC(O)N($R^{17}$)—, —CSN($R^{17}$)—, —N($R^{17}$)CO—, —N($R^{17}$)C(O)O—, —N($R^{17}$)CS—, —S(O)$_2$N($R^{17}$)—, —N($R^{17}$)S(O)$_2$—, —N($R^{17}$)CON($R^{17}$)—, —N($R^{17}$)CSN($R^{17}$)—, or —N($R^{17}$) SO$_2$N($R^{17}$)— groups. Where the linker group contains two $R^{17}$ substituents, these may be the same or different.

Particular examples of aliphatic groups represented by $R^2$, $R^{14}$, $R^{15}$ and/or $R^{16}$ include optionally substituted —$CH_3$, —$CH_2CH_3$, —$CH(CH_3)_2$, —$(CH_2)_2CH_3$, —$(CH_2)_3CH_3$, —$CH(CH_3)CH_2CH_3$, —$CH_2CH(CH_3)_2$, —$C(CH_3)_2$, —$(CH_2)_4CH_3$, —$(CH_2)_5CH_3$, —$CHCH_2$, —$CHCHCH_3$, —$CH_2CHCH_2$ —$CHCHCH_2CH_3$, —$CH_2CHCHCH_3$, —$(CH_2)_2CHCH_2$, —CCH, —$CCCH_3$, —$CH_2CCH$, —$CCCH_2CH_3$, —$CH_2CCCH_3$, or —$(CH_2)_2CCH$ groups. Where appropriate each of said groups may be optionally interrupted by one or two atoms and/or groups $L^2$ to form an optionally substituted hetero-aliphatic group. Particular examples include optionally substituted —$L^2CH_3$, —$CH_2L^2CH_3$, —$L^2CH_2CH_3$, —$CH_2L^2CH_2CH_3$, —$(CH_2)_2L^2CH_3$, —$L^2(CH_2)_2CH_3$ and —$(CH_2)_2L^2CH_2CH_3$ groups.

The optional substituents which may be present on aliphatic or heteroaliphatic groups represented by $R^2$, $R^{14}$, $R^{15}$, and/or $R^{16}$ include one, two, three or more substituents where each substituent may be the same or different and is selected from halogen atoms, or $C_{1-6}$alkoxy, hydroxy, thiol, $C_{1-6}$alkylthio, optionally substituted $C_{6-12}$arylamino, substituted amino groups or optionally substituted aromatic or heteroaromatic groups. Substituted amino groups include —$NHR^{18}$ and —$N(R^{18})_2$ groups where $R^{18}$ is a straight or branched alkyl group. Where two $R^{18}$ groups are present these may be the same or different. Particular examples of substituted groups represented by $R^2$, $R^{14}$, $R^{15}$ and/or $R^{16}$ include those specific groups just described substituted by one, two, or three halogen atoms such as fluorine atoms, for example groups of the type —$CH_2CF_3$, —$CH(CF_3)_2$, —$CH_2CH_2CF_3$, —$CH_2CH(CF_3)_2$ and —$C(CF_3)_2CH_3$, or substituted by one or two optionally substituted aromatic or heteroaromatic groups, for example optionally substituted phenyl, pyridinyl or pyrimidinyl groups.

Optionally substituted cycloaliphatic groups represented by $R^2$, $R^{14}$, $R^{15}$ and/or $R^{16}$ include optionally substituted $C_{3-10}$ cycloaliphatic groups. Particular examples include optionally substituted $C_{3-10}$ cycloalkyl, e.g. $C_{3-7}$ cycloalkyl or $C_{3-10}$ cycloalkenyl, e.g. $C_{3-7}$ cycloalkenyl groups.

Optionally substituted heterocycloaliphatic groups represented by $R^2$, $R^{14}$, $R^{15}$ and/or $R^{16}$ include optionally substituted $C_{3-10}$heterocycloaliphatic groups. Particular examples include optionally substituted $C_{3-10}$heterocycloalkyl, e.g. $C_{3-7}$heterocycloalkyl, or $C_{3-10}$heterocycloalkenyl, e.g. $C_{3-7}$ hetercycloalkenyl groups, each of said groups containing one, two, three or four heteroatoms or heteroatom-containing groups $L^2$ as just defined.

Optionally substituted polycycloaliphatic groups represented by $R^2$, $R^{14}$, $R^{15}$ and/or $R^{16}$ include optionally substitued $C_{7-10}$ bi- or tricycloalkyl or $C_{7-10}$bi- or tricycloalkenyl groups. Optionally substituted heteropolycycloaliphatic groups represented by $R^2$, $R^{14}$, $R^{15}$ and/or $R^{16}$ include the optionally substituted polycycloalkyl groups just described, but with each group additionally containing one, two, three or four $L^2$ atoms or groups.

Particular examples of $R^2$, $R^{14}$, $R^{15}$ and/or $R^{16}$ cycloaliphatic, polycycloaliphatic, heterocycloaliphatic and heteropolycycloaliphatic groups include optionally substituted cyclopropyl, cyclobutyl, cyclopentyl, cyclohexyl, cycloheptyl, 2-cyclobuten-1-yl, 2-cyclopenten-1-yl, 3-cyclopenten-1-yl, adamantyl, norbornyl, norbornenyl, tetrahydrofuranyl, pyrroline, e.g. 2- or 3-pyrrolinyl, pyrrolidinyl, pyrrolidinone, oxazolidinyl, oxazolidinone, dioxolanyl, e.g. 1,3-dioxolanyl, imidazolinyl, e.g. 2-imidazolinyl, imidazolidinyl, pyrazolinyl, e.g. 2-pyrazolinyl, pyrazolidinyl, thiazolinyl, thiazolidinyl, pyranyl, e.g. 2- or 4-pyranyl, piperidinyl, piperidinone, 1,4-dioxanyl, morpholinyl, morpholinone, 1,4-dithianyl, thiomorpholinyl, piperazinyl, 1,3,5-trithianyl, oxazinyl, e.g. 2H-1,3-, 6H-1,3-, 6H-1,2-, 2H-1,2- or 4H-1,4-oxazinyl, 1,2,5-oxathiazinyl, isoxazinyl, e.g. o- or p-isoxazinyl, oxathiazinyl, e.g. 1,2,5 or 1,2,6-oxathiazinyl, or 1,3,5,-oxadiazinyl groups.

The optional substituents which may be present on the $R^2$, $R^{14}$, $R^{15}$ and $R^{16}$ cycloaliphatic, polycycloaliphatic, heterocycloaliphatic or heteropolycycloaliphatic groups include one, two, three or more of those substituents described above in relation to $R^2$ aliphatic or heteroaliphatic groups. Additionally $R^2$, $R^{14}$, $R^{15}$ and $R^{16}$ cycloaliphatic, polycycloaliphatic, heterocycloaliphatic or heteropolycycloaliphatic groups may be optionally substituted by straight or branched alkyl, alkenyl, alkynyl or haloalkyl groups.

Optionally substituted aromatic groups represented by the groups $R^2$, $R^{14}$, $R^{15}$ and/or $R^{16}$ in a base represented by $R^{1a}N(R^2)$— include for example monocyclic or bicyclic fused ring $C_{6-12}$ aromatic groups, such as phenyl, 1- or 2-naphthyl, 1- or 2-tetrahydronaphthyl, indanyl or indenyl groups. Each of these aromatic groups may be optionally substituted by one, two, three or more $R^{19}$ atoms or groups as defined below.

Heteroaromatic groups represented by the groups $R^2$, $R^{14}$, $R^{15}$ and/or $R^{16}$ include for example $C_{1-9}$ heteroaromatic groups containing for example one, two, three or four heteroatoms selected from oxygen, sulphur or nitrogen atoms. In general, the heteroaromatic groups may be for example monocyclic or bicyclic fused ring heteroaromatic groups. Monocyclic heteroaromatic groups include for example five- or six-membered heteroaromatic groups containing one, two, three or four heteroatoms selected from oxygen, sulphur or nitrogen atoms. Bicyclic heteroaromatic groups include for example eight- to thirteen-membered fused-ring heteroaromatic groups containing one, two or more heteroatoms selected from oxygen, sulphur or nitrogen atoms.

Particular examples of heteroaromatic groups of these types include pyrrolyl, furyl, thienyl, imidazolyl, N-$C_{1-16}$ alkylimidazolyl, oxazolyl, isoxazolyl, thiazolyl, isothiazolyl, pyrazolyl, 1,2,3-triazolyl, 1,2,4-triazolyl, 1,2,3-oxadiazolyl, 1,2,4-oxadiazolyl, 1,2,5-oxadiazolyl, 1,3,4-oxadiazolyl, 1,3,4-thiadiazole, pyridyl, pyrimidinyl, pyridazinyl, pyrazinyl, 1,3,5-triazinyl, 1,2,4-triazinyl, 1,2,3-triazinyl, benzofuryl, [2,3-dihydro]benzofuryl, benzothienyl, benzotriazolyl, indolyl, indolinyl, isoindolyl, indazolinyl, benzimidazolyl, imidazo[1,2-a]pyridyl, benzothiazolyl, benzoxazolyl, benzisoxazolyl, benzopyranyl, [3,4-dihydro]benzopyranyl, quinazolinyl, qunoxalinyl, naphthyridinyl, pyrido[3,4-b]pyridyl, pyrido[3,2-b]pyridyl, pyrido[4,3-b]-pyridyl, quinolinyl, isoquinolinyl, phthalazinyl, tetrazolyl, 5,6,7,8-tetrahydroquinolinyl, 5,6,7,8-tetrahydroisoquinolinyl, and imidyl, e.g. succinimidyl, phthalimidyl, or naphthalimidyl such as 1,8-naphthalimidyl.

Optional substituents which may be present on the aromatic or heteroaromatic groups represented by the groups $R^2$, $R^{14}$, $R^{15}$ and/or $R^{16}$ include one, two, three or more substituents, each selected from an atom or group $R^{19}$ in which $R^{19}$ is —$R^{19a}$ or —$Alk^3(R^{19a})_m$, where $R^{19a}$ is a halogen atom, or an amino (—$NH_2$), substituted amino, nitro, cyano, amidino, hydroxyl (—OH), substituted hydroxyl, formyl, carboxyl (—$CO_2H$), esterified carboxyl, thiol (—SH), substituted thiol, —$COR^{20}$ [where $R^{20}$ is an —$Alk^3(R^{19a})_m$, aryl or heteroaryl group], —$CSR^{20}$, —$SO_3H$, —$SO_3R^{20}$, —$SOR^{20}$, —$SO_2R^{20}$, —$SO_2NH_2$, —$SO_2NHR^{20}$, —$SO_2N(R^{20})_2$, —$CONH_2$, —$CSNH_2$, —$CONHR^{20}$, —$CSNHR^{20}$, —$CON[R^{20}]_2$, —$CSN(R^{20})_2$, —$N(R^{21})SO_2R^{20}$, [where $R^{21}$ is a hydrogen atom or a straight or branched alkyl group] —$N(SO_2R^{20})_2$, —$N(R^{21})SO_2NH_2$, —$N(R^{21})SO_2NHR^{20}$, —$N(R^{21})SO_2N(R^{20})_2$, —$N(R^{21})COR^{20}$, —$N(R^{21})CONH_2$, —$N(R^{21})CONHR^{20}$, —$N(R^{21})CON(R^{20})_2$, —$N(R^{21})CSNH_2$, —$N(R^{21})CSNHR^{20}$, —$N(R^{21})CSN(R^{20})_2$, —$N(R^{21})CSR^{20}$, —$N(R^{21})C(O)OR^{20}$, —$SO_2NHet^1$ [where —$NHet^1$ is an optionally substituted $C_{5-7}$cyclicamino group optionally containing one or more other —O— or —S— atoms or —$N(R^{21})$—, —C(O)— or —C(S)— groups], —$CONHet^1$, —$CSNHet^1$, —$N(R^{21})SO_2NHet^1$, —$N(R^{21})CONHet^1$, —$N(R^{21})CSNHet^1$, —$SO_2N(R^{21})Het^2$ [where $Het^2$ is an optionally substituted monocyclic $C_{5-7}$carbocyclic group optionally containing one or more —O— or —S— atoms or —$N(R^{21})$—, —C(O)— or —C(S)— groups], —$Het^2$, —$CON(R^{21})Het^2$, —$CSN(R^{21})Het^2$, —$N(R^{21})CON(R^{21})Het^2$, —$N(R^{21})CSN(R^{21})Het^2$, aryl or heteroaryl group; $Alk^3$ is a straight or branched $C_{1-6}$alkylene, $C_{2-6}$alkenylene or $C_{2-6}$alkynylene chain, optionally interrupted by one, two or three —O— or —S— atoms or —$S(O)_n$ [where n is an integer 1 or 2] or —$N(R^{21})$— groups; and m is zero or an integer 1, 2 or 3. It will be appreciated that when two $R^{20}$ or $R^{21}$ groups are present in one of the above substituents, the $R^{20}$ or $R^{21}$ groups may be the same or different.

When in the group —$Alk^3(R^{19a})_m$ m is an integer 1, 2 or 3, it is to be understood that the substituent or substituents $R^{19a}$ may be present on any suitable carbon atom in —$Alk^3$. Where more than one $R^{19a}$ substituent is present these may be the same or different and may be present on the same or different atom in —$Alk^3$. Clearly, when m is zero and no substituent $R^{19a}$ is present the alkylene, alkenylene or alkynylene chain represented by $Alk^3$ becomes an alkyl, alkenyl or alkynyl group.

When $R^{19a}$ is a substituted amino group it may be for example a group —$NHR^{20}$ [where $R^{20}$ is as defined above] or a group —$N(R^{20})_2$ wherein each $R^{20}$ group is the same or different.

When $R^{19a}$ is a halogen atom it may be for example a fluorine, chlorine, bromine, or iodine atom.

When $R^{19a}$ is a substituted hydroxyl or substituted thiol group it may be for example a group —$OR^{20}$ or a —$SR^{20}$ or —$SC(=NH)NH_2$ group respectively.

Esterified carboxyl groups represented by the group $R^{19a}$ include groups of formula —$CO_2Alk^4$ wherein $Alk^4$ is a straight or branched, optionally substituted $C_{1-8}$alkyl group such as a methyl, ethyl, n-propyl, i-propyl, n-butyl, i-butyl, s-butyl or t-butyl group; a $C_{6-12}$aryl$C_{1-8}$alkyl group such as an optionally substituted benzyl, phenylethyl, phenylpropyl, 1-naphthylmethyl or 2-naphthylmethyl group; a $C_{6-12}$aryl group such as an optionally substituted phenyl, 1-naphthyl or 2-naphthyl group; a $C_{6-12}$aryloxyC1-8alkyl group such as an optionally substituted phenyloxymethyl, phenyloxyethyl, 1-naphthyloxymethyl, or 2-naphthyloxymethyl group; an optionally substituted $C_{1-8}$alkanoyloxy$C_{1-8}$alkyl group, such as a pivaloyloxymethyl, propionyloxyethyl or propionyloxypropyl group; or a $C_{6-12}$aroyloxy$C_{1-8}$alkyl group such as an optionally substituted benzoyloxyethyl or benzoyloxypropyl group. Optional substituents present on the $Alk^4$ group include $R^{19a}$ substituents described above.

When $Alk^3$ is present in or as a substituent it may be for example a methylene, ethylene, n-propylene, i-propylene, n-butylene, i-butylene, s-butylene, t-butylene, ethenylene, 2-propenylene, 2-butenylene, 3-butenylene, ethynylene, 2-propynylene, 2-butynylene or 3-butynylene chain, optionally interrupted by one, two, or three —O— or —S—, atoms or —S(O)—, —$S(O)_2$— or —$N(R^{21})$— groups.

Aryl or heteroaryl groups represented by the groups $R^{19a}$ or $R^{20}$ include mono- or bicyclic optionally substituted $C_{6-12}$ aromatic or $C_{1-9}$ heteroaromatic groups as described above for the group $R^2$. The aromatic and heteroaromatic groups may be attached to the remainder of the compound of formula (1) by any carbon or hetero e.g. nitrogen atom as appropriate.

When —$NHet^1$ or —$Het^2$ forms part of a substituent $R^{19}$ each may be for example an optionally substituted pyrrolidinyl, pyrazolidinyl, piperazinyl, morpholinyl, thiomorpholinyl, piperidinyl, imidazolidinyl, oxazolidinyl or thiazolidinyl group. Additionally $Het^2$ may represent for example, an optionally substituted cyclopentyl or cyclohexyl group. Optional substituents which may be present on —$NHet^1$ or —$Het^2$ include those substituents described above in relation to $R^6$.

Particularly useful atoms or groups represented by $R^{19}$ include fluorine, chlorine, bromine or iodine atoms, or $C_{1-6}$alkyl, e.g. methyl, ethyl, n-propyl, i-propyl, n-butyl or t-butyl, optionally substituted $C_{3-10}$cycloalkyl e.g. cyclopentyl or cyclohexyl, optionally substituted phenyl, pyridyl, pyrimidinyl, pyrrolyl, furyl, thiazolyl, thienyl, morpholinyl, thiomorpholinyl, piperazinyl, pyrrolidinyl, pyrazolidinyl, imidazolidinyl, oxazolidinyl, thiazolidinyl or piperidinyl, $C_{1-6}$hydroxyalkyl, e.g. hydroxymethyl or hydroxyethyl, carboxy$C_{1-6}$alkyl, e.g. carboxyethyl, $C_{1-6}$alkylthio e.g. methylthio or ethylthio, carboxy$C_{1-6}$alkylthio, e.g. carboxymethylthio, 2-carboxyethylthio or carboxypropylthio, $C_{1-6}$alkoxy, e.g. methoxy, ethoxy, or isopropyloxy, hydroxy$C_{1-6}$alkoxy, e.g. 2-hydroxyethoxy, optionally substituted phenoxy, pyridyloxy, thiazolyoxy, phenylthio or pyridylthio, $C_{5-7}$cycloalkoxy, e.g. cyclopentyloxy, halo$C_{1-6}$alkyl, e.g. trifluoromethyl, halo$C_{1-6}$alkoxy, e.g. trifluoromethoxy, $C_{1-6}$alkylamino, e.g. methylamino or ethylamino, optionally substituted $C_{6-12}$aryl$C_{1-6}$alkylamino e.g. benzylamino, amino (—$NH_2$), amino$C_{1-6}$alkyl, e.g. aminomethyl or aminoethyl, $C_{1-6}$dialkylamino, e.g. dimethylamino or diethylamino, amino$C_{1-6}$alkylamino e.g. aminomethylamino, $Het^1NC_{1-6}$alkylamino, e.g. morpholinopropylamino, $C_{1-6}$alkylamino$C_{1-6}$alkyl, e.g. ethylaminoethyl, $C_{1-6}$dialkylamino$C_{1-6}$alkyl, e.g. diethylaminoethyl, amino$C_{1-6}$alkoxy, e.g. aminoethoxy, $C_{1-6}$alkylamino$C_{1-6}$alkoxy, e.g. methylaminoethoxy, $C_{1-6}$dialkylamino$C_{1-6}$alkoxy, e.g. dimethylaminoethoxy, diethylaminoethoxy, diisopropylaminoethoxy, or dimethylaminopropoxy, hydroxy$C_{1-6}$alkylamino e.g. hydroxyethylamino, imido, such as phthalimido or naphthalimido, e.g. 1,8-naphthalimido, nitro, cyano, amidino, hydroxyl (—OH), formyl [HC(O)—], carboxyl (—$CO_2H$), —$CO_2Alk^4$ [where $Alk^4$ is as defined above], $C_{1-6}$ alkanoyl e.g. acetyl, optionally substituted benzoyl, thiol (—SH), thio$C_{1-6}$alkyl, e.g. thiomethyl or thioethyl —$SC(=NH)NH_2$, sulphonyl (—$SO_3H$), —$SO_3Alk^4$, $C_{1-6}$alkylsulphinyl e.g. ethylsulphinyl, $C_{1-6}$alkylsulphonyl, e.g. methylsulphonyl, aminosulphonyl (—$SO_2NH_2$), $C_{1-6}$alkylaminosulphonyl, e.g. methylaminosulphonyl or ethylaminosulphonyl, $C_{1-6}$dialkylaminosulphonyl, e.g. dimethylaminosulphonyl or diethylaminosulphonyl, phenylaminosulphonyl, carboxamido (—$CONH_2$), $C_{1-6}$alkylaminocarbonyl, e.g. methylaminocarbonyl or ethylaminocarbonyl, $C_{1-6}$dialkylaminocarbonyl, e.g. dimethylaminocarbonyl or diethylaminocarbonyl, amino$C_{1-6}$ alkylaminocarbonyl, e.g. aminoethylaminocarbonyl, $C_{1-6}$dialkylamino$C_{1-6}$alkylaminocarbonyl, e.g. diethylaminoethylaminocarbonyl, aminocarbonylamino, $C_{1-6}$alkylam inocarbonylamino, e.g. methylaminocarbonylamino or ethylaminocarbonylamino, $C_{1-6}$dialkylaminocarbonylamino, e.g. dimethylaminocarbonylamino or diethylaminocarbonylamino, $C_{1-6}$alkylaminocabonyl$C_{1-6}$alkylamino, e.g. methylaminocarbonylmethylamino, aminothiocarbonylamino, $C_{1-6}$alkylaminothiocarbonylamino, e.g. methylaminothiocarbonylamino or ethylaminothiocarbonylamino, $C_{1-6}$dialkylaminothiocarbonylamino, e.g. dimethylaminothiocarbonylamino or diethylaminothiocarbonylamino, $C_{1-6}$alkylaminothiocarbonyl$C_{1-6}$alkylamino, e.g. ethylaminothiocarbonylmethylamino, —CONHC(=NH) $NH_2$, $C_{1-6}$alkylsulphonylamino, e.g. methylsulphonylamino or ethylsulphonylamino, $C_{1-6}$dialkylsulphonylamino, e.g. dimethylsulphonylamino or diethylsulphonylamino, optionally substituted phenylsulphonylamino, aminosulphonylamino (—$NHSO_2NH_2$), $C_{1-6}$alkylaminosulphonylamino, e.g. methylaminosulphonylamino or ethylaminosulphonylamino, $C_{1-6}$dialkylaminosulphonylamino, e.g. dimethylaminosulphonylamino or diethylam inosulphonylamino, optionally substituted morpholinesulphonylamino or morpholinesulphonyl$C_{1-6}$alkylamino, optionally substituted phenylaminosulphonylamino, $C_{1-6}$alkanoylamino, e.g. acetylamino, amino$C_{1-16}$alkanoylamino e.g. aminoacetylamino, $C_{1-6}$dialkylamino$C_{1-6}$alkanoylamino, e.g. dimethylaminoacetylamino, $C_{1-6}$alkanoylamino$C_{1-6}$ alkyl, e.g. acetylaminomethyl, $C_{1-6}$alkanoylamino$C_{1-6}$ alkylamino, e.g. acetamidoethylamino, $C_{1-6}$alkoxycarbonylamino, e.g. methoxycarbonylamino, ethoxycarbonylamino or t-butoxycarbonylamino or optionally substituted benzyloxy, pyridylmethoxy, thiazolylmethoxy, benzyloxycarbonylamino, benzyloxycarbonylamino$C_{1-6}$alkyl e.g. benzyloxycarbonylaminoethyl, thiobenzyl, pyridylmethylthio or thiazolylmethylthio groups.

Where desired, two $R^{19}$ substituents may be linked together to form a cyclic group such as a cyclic ether, e.g. a $C_{1-6}$alkylenedioxy group such as methylenedioxy or ethylenedioxy.

It will be appreciated that where two or more $R^{19}$ substituents are present, these need not necessarily be the same atoms and/or groups. In general, the substituent(s) may be present at any available ring position in the aromatic or heteroaromatic group represented by $R^2$, $R^{14}$, $R^{15}$ and/or $R^{16}$.

Particular examples of cyclic nitrogen bases represented by the group $R^{1a}N(R^2)$— in compounds of the invention include those wherein $R^{1a}$ is an optionally substituted four- to ten-membered, for example six-membered, mono- or bicyclic fused-ring cycloaliphatic or aromatic group containing one, two, three or more nitrogen atoms and optionally one or more other heteroatoms such as oxygen and sulphur atoms. Suitable examples include optionally substituted pyrrolidinyl, pyrrolinyl, piperidinyl, tetrahydropyridinyl, piperazinyl, tetrahydropyrimidinyl, homopiperazinyl, triazinyl, morpholinyl, thiomorpholinyl, thiazolinyl, thiazolidinyl, indolinyl, tetrahydroquinolinyl, tetrahydroisoquinlinyl, pyrrolyl, pyrazolyl, imidazolyl, imidazolinyl, imidazolidinyl, triazolyl, tetrazolyl, isoxazolyl, oxazolyl, oxazolidinyl, thiazolyl, isothiazolyl, oxadiazolyl, thiadiazolyl, indolyl, indazolyl, benzimidazolyl, benzoxazolyl, benzisoxazolyl, benzothiazolyl, pyridyl, pyrimidinyl, pyrazinyl, triazinyl, quinolinyl and isoquinolinyl groups. Optional substituents which may be present on these groups include one, two or three of those $R^{19}$ substituents described herein. The ring $R^{1a}$ will generally be attached to the —$N(R^2)$— group through any available ring carbon atom.

Cyclic nitrogen bases represented by the group $R^{1b}$ in compounds of the invention include those optionally substituted four- to ten-membered mono- or bicyclic fused-ring cycloaliphatic or aromatic groups containing one, two, three or more nitrogen atoms and optionally one or more other heteroatoms as just generally and particularly described for the group $R^{1a}$. The cyclic group $R^{1b}$ may be attached to the adjacent $Ar^2$ group through a ring carbon atom, or where appropriate a ring nitrogen atom.

Acyclic nitrogen bases represented by the group $R^{1b}$ in compounds of the invention include those acyclic groups as just generally and particularly described for the group $R^{1a}$.

When in the compounds of the invention the Ar group is a bicyclic ring it may be for example a ring of formula:

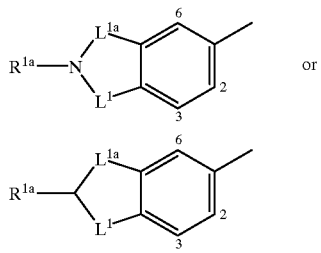

[where $R^{1a}N$ and $R^{1a}CH$ form the nitrogen base $R^{1c}$ described in formula (1)] in which each of the carbon atoms at positions 2-, 3- and 6- may optionally be substituted or replaced by a nitrogen atom as described above in relation to the ring $Ar^2$. In these compounds $R^{1a}$, $L^1$ and $L^{1a}$ may be as decribed previously. $L^{1a}$ may in particular be a —$CH_2$—, —$(CH_2)_2$— or —$(CH_2)_3$— chain.

Nitrogen bases represented by the group $R^{1d}$ in compounds of the invention include those acyclic and cyclic groups as just generally and particularly described for the group $R^{1a}$. The group $R^{1d}$ may be attached to the adjacent $L^1$ group through a carbon atom, or where appropriate a nitrogen atom.

When in the compounds of the invention the group Z contains a group $R^{13}$ which is an optionally substituted aliphatic, cycloaliphatic, heteroaliphatic, heterocycloalphatic, aromatic or heteroaromatic group, each of these groups may be any of those generally and previously particularly described for the group $R^2$. Optional substituents which may be present on such groups include those described for $R^2$, for example one, two or three $R^{19}$ substituents as described above when $R^{13}$ is an aromatic or heteroaromatic group. Additionally, when $R^{13}$ is an aliphatic or heteroaliphatic group it may be optionally substituted by an optionally substituted aromatic or heteroaromatic group of the type described above in relation to $R^2$.

When the group Z is —$C(R^{12a})(R^{13})$—$CH(R^{12b})$—, then $R^{12a}$ and $R^{12b}$ together with the carbon atoms to which they are attached may form for example a cyclopropyl group.

Derivatives of the carboxylic acid group R in compounds of the invention include caboxylic acid esters and amides. Particular esters and amides include —$CO_2Alk^4$ and —$CONR^9R^{10}$ groups as described herein. Biosteres of the carboxylic acid group R include tetrazoles, or other acids such as squaric acid, phosphoric acid, sulphonic acid, sulphinic acid, or boronic acid.

Aromatic or non-aromatic monocycles represented by $Ar^1$ in compounds of the invention include for example optionally substituted rings selected from:

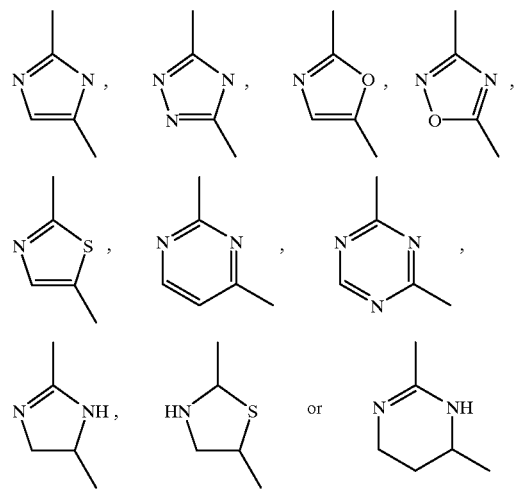

When a carbon atom is available in rings of these types, and in general in rings represented by $Ar^1$, it may be optionally substituted by a halogen atom or a straight or branched alkyl, haloalkyl, alkoxy, haloalkoxy or alkylthio group, or a —OH, —$CO_2H$, —$CO_2R^8$, —CN, —$NH_2$, —$NO_2$ or straight or branched alkylamino or dialkylamino group. Additionally, any suitable nitrogen atom when present may be optionally substituted, for example by a straight or branched alkyl group.

The presence of certain substituents in the compounds of formula (1) may enable salts of the compounds to be formed. Suitable salts include pharmaceutically acceptable salts, for example acid addition salts derived from inorganic or organic acids, and salts derived from inorganic and organic bases.

Acid addition salts include hydrochlorides, hydrobromides, hydroiodides, alkylsulphonates, e.g. methanesulphonates, ethanesulphonates, or isothionates, arylsulphonates, e.g. p-toluenesulphonates, besylates or napsylates, phosphates, sulphates, hydrogen sulphates, acetates, trifluoroacetates, propionates, citrates, maleates, fumarates, malonates, succinates, lactates, oxalates, tartrates and benzoates.

Salts derived from inorganic or organic bases include alkali metal salts such as sodium or potassium salts, alkaline earth metal salts such as magnesium or calcium salts, and organic amine salts such as morpholine, piperidine, dimethylamine or diethylamine salts.

Particularly useful salts of compounds according to the invention include pharmaceutically acceptable salts, especially acid addition pharmaceutically acceptable salts.

In one group of compounds of formula (1) Ar may be for example a group $R^{1a}N(R^2)L^1Ar^2$—, $R^{1b}Ar^2$ or a group:

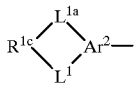

in which $R^{1a}$, $R^{1c}$, $R^2$, $L^1$, $L^{1a}$ and $Ar^2$ are as previously generally and particularly defined and $R^{1b}$ is a cyclic nitrogen base.

A particularly useful group of compounds according to the invention has the formula (1a):

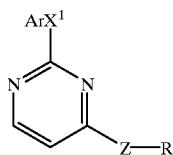

(1a)

in which Ar, $X^1$, Z and R are as defined for formula (1) and the salts, solvates, hydrates and N-oxides thereof.

In the compounds of formula (1a) and in general in compounds of the invention the pyrimidine ring may be additionally optionally substituted by one or two straight or branched alkyl, haloalkyl, haloalkoxy or alkoxy groups, or —OH, —CO$_2$H, —CO$_2$R$^8$, —CN, —NH$_2$, —NO$_2$ halogen or straight or branched alkylamino or dialkylamino groups.

In compounds of formula (1a) and in general in compounds of the invention the group Z is preferably a —CH(R$^{13}$)CH$_2$— or —C(R$^{13}$)=CH— group. In these compounds the group $R^{13}$ is preferably an optionally substituted aromatic or heteroaromatic group as defined herein. Particularly useful groups include optionally substituted phenyl and five- or six-membered heteroaromatic groups, e.g. optionally substituted pyridyl and pyrimidinyl groups.

In compounds of formula (1a) and in general in compounds of the invention the optional substituents on $R^{13}$ groups include one or more substituents which may be the same or different selected from halogen atoms, especially fluorine, chlorine or bromine atoms, $C_{1-6}$alkyl groups, specially methyl, ethyl and i-propyl groups, carboxyl (—CO$_2$H) or esterified carboxyl (—CO$_2$Alk$^4$) groups, amino (—NH$_2$) or substituted amino groups, especially aminoCl6alkylaminocarbonyl groups e.g. aminoethylaminocarbonyl groups, hydroxyl or $C_{1-6}$alkoxy groups, especially methoxy, ethoxy and isopropyloxy, halo$C_{1-6}$alkyl groups, especially trifluoromethyl, halo$C_{1-6}$alkoxy groups, especially trifluoromethoxy, thiol (—SH) or thio$C_{1-6}$alkyl groups, especially thiomethyl, nitro, cyano, amidino, $C_{1-6}$alkylsulphinyl or $C_{1-6}$alkylsulphonyl groups.

In the compounds of formula (1a) and in general in compounds of the invention, the group R is preferably a carboxylic acid (—CO$_2$H).

The group $X^1$ in general and in compounds of formula (1a) is preferably —O—, —S—, —NH— or —N(R$^5$)—. A particularly useful —N(R$^5$) group is —N(CH$_3$)—.

Particularly useful compounds of the invention include those wherein Ar is a group $R^{1a}N(R^2)$—L$^1$—Ar$^2$. $R^{1b}Ar^2$ or $R^{1d}L^1Ar^2$ in which $R^{1a}$, $R^{1b}$, $R^{1d}$, $R^2$, $L^1$ and $Ar^2$ are as previously generally and particularly defined. In these compounds when Ar is a group $R^{1a}N(R^2)$—L$^1$—Ar$^2$, R$^2$ may be in particular a hydrogen atom. $R^2$ may be in particular a hydrogen atom. $L^1$ may in particular by a group —C(R$^3$)(R$^4$)— or —C(O)— where $R^3$ and $R^4$ are as previously generally and particularly defined. An especially useful $L^1$ group is —CH$_2$—. $R^{1a}$ may in particular be a group $R^{14}R^{15}NC(X^2)$—, $R^{15}C(=NR^{14})$— or an optionally substituted four- to ten-membered, particularly six-membered, nitrogen-containing aromatic group optionally containing one or more other heteroatoms as described herein in relation to $R^{1a}$. Particularly useful $R^{1a}$ groups include H$_2$NC(=NH)—, imidazolinyl, benzimidazolyl and optionally substituted pyridyl groups. Especially useful optionally substituted pyridyl groups include pyridyl, 2-aminopyridyl and 2-methylaminopyridyl groups.

IIn these compounds when Ar is a group $R^{1b}Ar^2$, $R^{1b}$ may in particular be a group $R^{14}R^{15}NC(X^2)$, $R^{15}C(=NR^{14})$—, or an optionally substituted four to ten membered, particularly five or six-membered, nitrogen containing heterocycloaliphatic or aromatic group optionally containing one or more other heteroatoms as described herein in relation to $R^{1b}$. Particularly useful $R^{1b}$ groups include optionally substituted pyridyl and imidazoyl groups. Especially useful $R^{1b}$ groups include a 2-aminopyridyl and 2-methylaminopyridyl group.

In these compounds when Ar is a group $R^{1d}L^1Ar^2$, $R^{1d}$ may in particular be a group $R^{14}R^{15}NC(X^2)$—, $R^{15}C(=NR^{14})$— or an optionally substituted four to ten membered, particularly five or six membered, nitrogen containing heterocycloaliphatic or aromatic group optionally containing one or more other heteroatoms as described herein in relation to $R^{1a}$. Particularly useful $R^{1d}$ groups include H$_2$NC(=NH)— and optionally substituted imidazoyl, imidazolinyl, triazolyl and pyridyl groups. In these compounds $L^1$ may be in particular a group —C(R$^3$)(R$^4$)— where $R^3$ and $R^4$ are as previously generally and particularly defined. Particularly useful $L^1$ groups include —CH$_2$— and —CH(OH)—.

In these compounds and in general in compounds of the invention $Ar^2$ is an optionally substituted six-membered 1,4-arylene, especially a 1,4-phenylene group.

Particularly useful compounds of the invention include:
3-(4-[2-Aminoethyl]benzamide)-3-(2-[4-{(2-pyridinylamino)methyl}phenoxy]-4-pyrimidinyl) propanoic acid;
3-(2-{4-[(4,5-Dihydro-1H-imidazol-2-ylamino)methyl]phenoxy}-4-pyrimidinyl)-3-(4-fluorophenyl)propanoic acid;
3-{2-[4-({[Amino(imino)methyl]amino}methyl)phenoxy]-4-pyrimidinyl}-3-(4-benzoic acid)propanoic acid;
3-[2-(4-[({Amino(imino)methyl}amino)methyl]-N-methylaniliino)-4-pyrimidinyl]-3-(4-fluorophenol) propanoic acid;
3-(3-Methoxyphenyl)-3-(2-{4-{(2-pyridinylamino) methyl]phenoxy}-4-pyrimidinyl)propanoic acid;
3-[2-(4-{6-Amino-2-pyridinyl}phenoxy)-4-pyrimidinyl]-3-(4-carboxyphenyl)propanoic acid;
3-[2-(4-{2-(N-methylamino)-6-pyridinyl}phenoxy)-4-pyrimidinyl]-3-(4-carboxyphenyl)propanoic acid;

3-(2-[4-{(1H-1,3-Benzimidazol-2-yl-amino) methyl}phenoxy]4-pyrimidinyl)-3-(4-fluorophenyl) propanoic acid;

3-(3-Benzenecarboxylic acid)-3-(2-{4-[(2-pyridinylamino)methyl]phenoxy}-4-pyrimidinyl) propanoic acid;

and the salts, solvates, hydrates and N-oxides thereof.

Compounds according to the invention are potent and selective inhibitors of $\alpha_v$integrins. The ability of the compounds to act in this way may be simply determined by employing tests such as those described in the Examples hereinafter.

The compounds are of use in modulating cell adhesion and in particular are of use in the prophylaxis and treatment of diseases or disorders involving inappropriate growth or migration of cells. The invention extends to such a use and to the use of the compounds of formula (1) for the manufacture of a medicament for treating such diseases and disorders. Particular diseases include inflammatory diseases, and diseases involving angiogenesis, bone resorption or cellular or matrix over-expansion.

Particular uses to which the compounds of the invention may be put include the treatment or inhibition of tumour growth and metastasis; retinopathy; macular degeneration psoriasis; rheumatoid arthritis; osteoporosis; bone resorption following or due to joint replacement, hypercalcemia of malignancy, Paget's disease, glucocorticoid treatment, immobilisation-induced osteopenia, hyperparathyroidism or peridontal disease; vascular restenosis; atherosclerosis; inflammatory bowel disease; and psoriasis.

For the prophylaxis or treatment of disease the compounds according to the invention may be administered as pharmaceutical compositions, and according to a further aspect of the invention we provide a pharmaceutical composition which comprises a compound of formula (1) together with one or more pharmaceutically acceptable carriers, excipients or diluents.

Pharmaceutical compositions according to the invention may take a form suitable for oral, buccal, parenteral, nasal, topical or rectal administration, or a form suitable for administration by inhalation or insufflation.

For oral administration, the pharmaceutical compositions may take the form of, for example, tablets, lozenges or capsules prepared by conventional means with pharmaceutically acceptable excipients such as binding agents (e.g. pregelatinised maize starch, polyvinylpyrrolidone or hydroxypropyl methylcellulose); fillers (e.g. lactose, microcrystalline cellulose or calcium hydrogen phosphate); lubricants (e.g. magnesium stearate, talc or silica); disintegrants (e.g. potato starch or sodium glycollate); or wetting agents (e.g. sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents, emulsifying agents, non-aqueous vehicles and preservatives. The preparations may also contain buffer salts, flavouring, colouring and sweetening agents as appropriate.

Preparations for oral administration may be suitably formulated to give controlled release of the active compound.

For buccal administration the compositions may take the form of tablets or lozenges formulated in conventional manner.

The compounds for formula (1) may be formulated for parenteral administration by injection e.g. by bolus injection or infusion. Formulations for injection may be presented in unit dosage form, e.g. in glass ampoule or multi dose containers, e.g. glass vials. The compositions for injection may take such forms as suspensions, solutions or emulsions in oily or aqueous vehicles, and may contain formulatory agents such as suspending, stabilising, preserving and/or dispersing agents. Alternatively, the active ingredient may be in powder form for constitution with a suitable vehicle, e.g. sterile pyrogen-free water, before use.

In addition to the formulations described above, the compounds of formula (1) may also be formulated as a depot preparation. Such long acting formulations may be administered by implantation or by intramuscular injection.

For nasal administration or administration by inhalation, the compounds for use according to the present invention are conveniently delivered in the form of an aerosol spray presentation for pressurised packs or a nebuliser, with the use of suitable propellant, e.g. dichlorodifluoromethane, trichlorofluoromethane, dichlorotetrafluoroethane, carbon dioxide or other suitable gas or mixture of gases.

The compositions may, if desired, be presented in a pack or dispenser device which may contain one or more unit dosage forms containing the active ingredient. The pack or dispensing device may be accompanied by instructions for administration.

The quantity of a compound of the invention required for the prophylaxis or treatment of a particular condition will vary depending on the compound chosen, and the condition of the patient to be treated. In general, however, daily dosages may range from around 100 ng/kg to 100 mg/kg e.g. around 0.01 mg/kg to 40 mglkg body weight for oral or buccal administration, from around long/kg to 50 mglkg body weight for parenteral administration and around 0.05 mg to around 1000 mg e.g. around 0.5 mg to around 1000 mg for nasal administration or administration by inhalation or insufflation.

The compounds of the invention may be prepared by a number of processes as generally described below and more specifically in the Examples hereinafter. Many of the reactions describd are well-known standard synthetic methods which may be applied to a variety of compounds and as such can be used not only to generate compounds of the invention, but also where necessary the intermediates thereto.

In the following process description, the symbols R, Ar, $X^1$, $Ar^1$, $L^1$ and Z when used in the formulae depicted are to be understood to represent those groups described above in relation to formula (1) unless otherwise indicated. In the reactions described below, it may be necessary to protect reactive functional groups, for example hydroxy, amino, thio or carboxy groups, where these are desired in the final product, to avoid their unwanted participation in the reactions. Conventional protecting groups may be used in accordance with standard practice [see, for example, Green, T. W. in "Protective Groups in Organic Synthesis", John Wiley and Sons, 1991]. In some instances, deprotection may be the final step in the synthesis of a compound of formula (1) and the processes according to the invention described hereinafter are to be understood to extend to such removal of protecting groups.

Thus according to a further aspect of the invention, a compound of formula (1) in which R is a —$CO_2H$ group may be obtained by hydrolysis of an ester of formula (1c):

$$Ar—X^1—Ar^1—Z—CO_2Alk^4 \qquad (1c)$$

where $Alk^4$ is an alkyl group, for example a $C_{1-6}$alkyl group as described above.

The hydrolysis may be performed using either an acid or base depending on the nature of $Alk^4$, for example an organic acid such as trifluoroacetic acid optionally in an organic solvent such as a haloalkane e.g. dichloromethane, or an inorganic base such as sodium, lithium or potassium hydroxide optionally in an aqueous organic solvent such as an amide e.g. a substituted amide such as dimethylformamide, an ether e.g. a cyclic ether such as tetrahydrofuran or dioxane or an alcohol e.g. methanol at around ambient temperature to 60° C. Where desired mixtures of such solvents may be used.

Esters of formula (1c) in which $X^1$ is an —O— or —S— atom or —N($R^5$)— group may be prepared by displacement of a leaving atom or group in a compound of formula (2):

RZAr$^1$L (2)

[where L is a leaving atom or group], with a reagent ArX$^1$H [where X$^1$ is as just defined].

The reaction may be performed at an elevated temperature, for example the reflux temperature, where necessary in the presence of a solvent, for example a substituted amide such as dimethylformamide, or an ether, e.g. a cyclic ether such as tetrahydrofuran, optionally in the presence of a base, for example a hydride such as sodium hydride or an organic amine such as pyridine, or an inorganic base such as cesium or potassium carbonate.

Particular examples of leaving groups represented by L in compounds of formula (2) include halogen atoms such as a chlorine or bromine atom, and sulphonyloxy groups, for example alkylsulphonyloxy groups such as a methylsulphonyloxy group.

Alternatively esters of formula (1c) in which $X^1$ is a —N($R^5$)— group may be prepared by cross-coupling an amine of formula ArN($R^5$)H with an organic halide of formula Hal$^5$Ar$^1$ZR[where Hal$^5$ is a halogen atom such as a bromine or chlorine atom].

The reaction may be carried out in the presence of a metal complex catalyst such as a palladium complex e.g. dichloro[1,1'-bis(diphenylphosphino)ferrocene]palladium(II), in the presence of an organic base, for example sodium-t-butoxide, in a solvent such as an ether e.g. a cyclic ether such as tetrahydrofuran, at an elevated temperature e.g. the reflux temperature.

Intermediate compounds of formula (2) in which Z is a —CH($R^{13}$)CH$_2$— group and R is a —CO$_2$Alk$^4$ group may be prepared by reaction of an intermediate of formula (3):

R$^{13}$CH$_2$Ar$^1$L (3)

with an α-haloester HalCH$_2$CO$_2$Alk$^4$ [where Hal is a halogen atom such as a bromine atom] in the presence of a strong base, e.g. a silazide such as sodium or lithium hexamethyldisilazide in a solvent such as an ether, e.g. a cyclic ether such as tetrahydrofuran at a low temperature, e.g. around −78° C.

Intermediates of formula (3) may be prepared by cross-coupling a halide of formula (4):

Hal$^1$CH$_2$Ar$^1$L (4)

[where Hal$^1$ is a halogen atom such as a chlorine atom] with an organometallic reagent R$^{13}$MHal$^2$, where M is a metal atom such as a zinc atom, and Hal$^2$ is a halogen atom such as a bromine atom.

The reaction may be carried out in the presence of a metal cataylst, for example a metal complex catalyst such as a palladium complex, e.g. tetrakis(triphenylphosphine)palladium, in a solvent such as an ether, e.g. a cyclic ether such as tetrahydrofuran, at an elevated temperature e.g. the reflux temperature.

Intermediate compounds of formula (2) in which Z is a —C(R$^{13}$)=CH— group and R is a —CO$_2$Alk$^4$ group may be prepared by reaction of a ketone of formula (5):

R$^{13}$COAr$^1$L (5)

with a phosphonate (Alk$^5$O)$_2$P(O)CH$_2$CO$_2$Alk$^4$ [where Alk$^5$ is a $C_{1-6}$alkyl group] in the presence of a base.

Suitable bases include organometallic bases, for example an organolithium compound such as n-butyllithium or lithium diisopropylamide, hydrides such as sodium or potassium hydride, alkoxides, such as sodium hydroxides, e.g. sodium methoxide, and cyclic amines, for example 1,8-diazabicyclo[5.4.0]undec-7-ene.

The reaction may be performed in a suitable solvent, for example a polar aprotic solvent such as an amide, e.g. N,Ndimethylformamide; or a non-polar solvent such as an ether, e.g. a cyclic ether such as tetrahydrofuran or a halogenated hydrocarbon, e.g. dichloromethane. Preferably the reaction is carried out at a low temperature, for example from around −78° C. to around ambient temperature.

Intermediate ketones of formula (5) may be obtained by reaction of a halide of formula (6):

Hal$^3$Ar$^1$L (6)

[where Hal$^3$ is a halogen atom such as a chlorine atom] by halogen-metal exchange with a base such as n-butyllithium, followed by reaction with a nitrile R$^{13}$CN, an acid chloride R$^{13}$COCl or an ester R$^{13}$CO$_2$Alk$^5$ in a solvent such as tetrahydrofuran at a low temperature e.g. around −70° C. and subsequent treatment with an acid such as hydrochloric acid at around ambient temperature.

In another process according to the invention a compound of formula (1) in which $X^1$ is a —C(R$^5$)(R$^6$)— group may be prepared by cross-coupling a halogen of formula (7):

RZAr$^1$Hal$^4$ (7)

[where Hal$^4$ is a halogen atom such as a chlorine atom] with an organometallic reagent ArC(R$^5$)(R$^6$)MHal$^2$ [where M and Hal$^2$ are as defined above]. The reaction may be carried out as described above for the preparation of intermediates of formula (3).

Where in the general processes described above intermediates such as ArX$^1$H, and the halides of formulae (6) and (7) are not available commercially or known in the literature, they may be readily obtained from simpler known compounds by one or more standard synthetic methods employing substitution, oxidation, reduction or cleavage reactions. Particular substitution approaches include conventional alkylation, arylation, heteroarylation, acylation, thioacylation, halogenation, sulphonylation, nitration, formylation and coupling procedures. It will be appreciated that these methods may also be used to obtain or modify other intermediates and in particular compounds of formula (1) where appropriate functional groups exist in these compounds. Particular examples of such methods are given in the Examples hereinafter.

Thus, for example, ester groups such as —CO$_2$Alk$^4$ in the compounds of formula (1) and intermediates thereto may be converted to the corresponding acid [—CO$_2$H] by acid- or base-catalysed hydrolysis depending on the nature of the groups R$^8$ or Alk$^4$. Acid- or base-catalysed hydrolysis may be achieved for example by treatment with an organic or inorganic acid, e.g. trifluoroacetic acid in an organic solvent e.g. dichloromethane or a mineral acid such as hydrochloric acid in a solvent such as dioxane or an alkali metal hydroxide, e.g. lithium hydroxide in an aqueous alcohol, e.g. aqueous methanol.

In a further example amides $R^{1a}N(R^2)COAr^2X^1H$ may be obtained by reaction of an amine $R^{1a}N(R^2)H_2$ with an acid $HX^1ArCO_2H$ in the presence of a condensing agent, for example a diimide such as 1-(3-dimethylaminopropyl)-3-ethylcarbodiimide hydrochloride or $N,N^1$-dicyclohexylcarbodiimide, or a benzotriazole such as [0-(7-azabenzotriazol-1-yl)-1,1,3,3-tetramethyluronium] hexafluorophosphate advantageously in the presence of a catalyst such as a N-hydroxy compound e.g. a N-hydroxybenzotriazole such as 1-hydroxybenzotriazole.

The reaction may be performed in the presence of a base, such as an amine e.g. triethylamine or N-methylmorpholine optionally in the presence of a catalytic amount of 4-dimethylaminopyridine in a solvent such as a halogenated hydrocarbon e.g. dichloromethane, at for example ambient temperature.

In a further example, $—OR^{20}$ [where $R^{20}$ represents an alkyl group such as methyl group] in compounds of formula (1) and intermediates thereto may be cleaved to the corresponding alcohol —OH by reaction with boron tribromide in a solvent such as a halogenated hydrocarbon, e.g. dichloromethane at a low temperature, e.g. around −78° C.

Alcohol [—OH] groups may also be obtained by hydrogenation of a corresponding $—OCH_2R^{20}$ group (where $R^{20}$ is an aryl group) using a metal catalyst, for example palladium on a support such as carbon in a solvent such as ethanol in the presence of ammonium formate, cyclohexadiene or hydrogen, from around ambient to the reflux temperature. In another example, —OH groups may be generated from the corresponding ester [e.g. $—CO_2Alk^4$] or aldehyde [—CHO] by reduction, using for example a complex metal hydride such as lithium aluminium hydride or sodium borohydride in a solvent such as methanol.

In another example, alcohol —OH groups in the compounds may be converted to a corresponding $—OR^{20}$ group by coupling with a reagent $R^{20}OH$ in a solvent such as tetrahydrofuran in the presence of a phosphine, e.g. triphenylphosphine and an activator such as diethyl-, diisopropyl-, or dimethylazodicarboxylate.

Aminosulphonylamino [$—NHSO_2NH_2$] groups in the compounds may be obtained, in another example, by reaction of a corresponding amine [$—NH_2$] with sulphamide in the presence of an organic base such as pyridine at an elevated temperature, e.g. the reflux temperature.

In a further example amine ($—NH_2$) groups may be alkylated using a reductive alkylation process employing an aldehyde and a reducing agent. Suitable reducing agents include borohydrides for example sodium triacetoxyborohyride or sodium cyanoborohydride. The reduction may be carried out in a solvent such as a halogenated hydrocarbon, e.g. dichloromethane, a ketone such as acetone, or an alcohol, e.g. ethanol, where necessary in the presence of an acid such as acetic acid at around ambient temperature. Alternatively, the amine and aldehyde may be initially reacted in a solvent such as an aromatic hydrocarbon e.g. toluene and then subjected to hydrogenation in the presence of a metal catalyst, for example palladium on a support such as carbon, in a solvent such as an alcohol, e.g. ethanol.

In a further example, amine [$—NH_2$] groups in compounds of formula (1) and intermediates thereto may be obtained by hydrolysis from a corresponding imide by reaction with hydrazine in a solvent such as an alcohol, e.g. ethanol at ambient temperature.

In another example, a nitro [$—NO_2$] group may be reduced to an amine [$—NH_2$], for example by catalytic hydrogenation using for example hydrogen in the presence of a metal catalyst, for example palladium on a support such as carbon in a solvent such as an ether, e.g. tetrahydrofuran or an alcohol e.g. methanol, or by chemical reduction using for example a metal, e.g. tin or iron, in the presence of an acid such as hydrochloric acid.

In a further example amine ($—CH_2NH_2$) group may be obtained by reduction of nitrites (—CN), for example by catalytic hydrogenation using for example hydrogen in the presence of a metal catalyst, for example palladium on a support such as carbon, or Raney® nickel, in a solvent such as an ether e.g. tetrahydrofuran or an alcohol e.g. methanol or ethanol at a temperature from ambient to the reflux temprature, or by chemical reduction using for example a metal hydride e.g. lithium aluminium hydride, in a solvent such as an ether e.g. a cyclic ether such as tetrahydrofuran, at a temperature from 0° C. to the reflux temperature Aromatic halogen substituents in the compounds may be subjected to halogen-metal exchange with a base, for example a lithium base such as n-butyl or t-butyl lithium, optionally at a low temperature, e.g. around −78° C., in a solvent such as tetrahydrofuran and then quenched with an electrophile to introduce a desired substituent. Thus, for example, a formyl group may be introduced by using dimethylformamide as the electrophile; a thiomethyl group may be introduced by using dimethyldisulphide as the electrophile.

In another example, sulphur atoms in the compounds, for example when present in a group $L^1$ may be oxidised to the corresponding sulphoxide or sulphone using an oxidising agent such as a peroxy acid, e.g. 3-chloroperoxybenzoic acid, in an inert solvent such as a halogenated hydrocarbon, e.g. dichloromethane, at around ambient temperature.

Where desired, imidourea groups, for example $N(R^2)C(=NR^{16})NR^{14}R^{15}$ represented by $R^{1a}N(R^2)$ in compounds of the invention or intermediates thereto may be obtained by reaction of a corresponding amine, for example $—NHR^2$, with a guanidine containing a leaving group, e.g. $LC(=NR^{16})NR^{14}R^{15}$ where L is a leaving group such as a pyrazole group, in a solvent such as acetonitrile at an elevated temperature.

N-oxides of compounds of formula (1) may be prepared for example by oxidation of the corresponding nitrogen base using an oxidising agent such as hydrogen peroxide in the presence of an acid such as acetic acid, at an elevated temperature, for example around 70° C. to 80° C., or alternatively by reaction with a peracid such as peracetic acid or m-chloroperoxybenzoic acid in a solvent, e.g. dichloromethane or tert-butanol, at a temperature from the ambient temperature to the reflux temperature.

Salts of compounds of formula (1) may be prepared by reaction of a compound of formula (1) with an appropriate base in a suitable solvent or mixture of solvents e.g. an organic solvent such as an ether e.g. diethylether, or an alcohol, e.g. ethanol using conventional procedures.

Where it is desired to obtain a particular enantiomer of a compound of formula (1) this may be produced from a corresponding mixture of enantiomers using any suitable conventional procedure for resolving enantiomers.

Thus for example diastereomeric derivatives, e.g. salts, may be produced by reaction of a mixture of enantiomers of formula (1) e.g. a racemate, and an appropriate chiral compound, e.g. a chiral base. The diastereomers may then be separated by any convenient means, for example by crystallisation and the desired enantiomer recovered, e.g. by treatment with an acid in the instance where the diastereomer is a salt.

In another resolution process a racemate of formula (1) may be separated using chiral High Performance Liquid Chromatography. Alternatively, if desired a particular enantiomer may be obtained by using an appropriate chiral intermediate in one of the processes described above.

Chromatography, recrystalliation and other conventional separation procedures may also be used with intermediates or final products where it is desired to obtain a particular geometric isomer of the invention.

The following Examples illustrate the invention. All temperatures are in ° C. The following abbreviations are used:
THF—tetrahydrofuran;
Boc—butoxycarbonyl;
DMF—dimethyl formamide;
DMSO—dimethyl sulphoxide;
Pd(dppf)$_2$Cl$_2$—dichloro[1,1'-bis(diphenylphosphino)ferrocene]palladium (II);
EDC—1-(3-dimethylaminopropyl)-3-ethylcarboiimide hydrochloride;
DMAP—4-dimethylaminopyridine.

INTERMEDIATE 1

4-[(2-Pyridinylamino)methyl]phenol

4-Hydroxybenzaldehyde (3.9 g, 32 mmol) and 2-aminopyridine (3.0 g, 32 mmol) were stirred in toluene (100 ml) at room temperature for 5 min. After concentrating in vacuo the residue was dissolved in ethanol (50 ml) and hydrogenated over Pd/C (100 mg) under a hydrogen atmosphere, for 18 h. The reaction mixture was filtered, concentrated and the crude product was chromatographed (dichloromethane-silica) to yield the title compound as white crystals (3.6 g, 56%). $^1$H NMR (CDCl$_3$) δ 8.10 (1H, m), 7.49 (1H, m), 7.14 (2H, d, J 7.8 Hz), 6.79 (2H, d, J 7.8 Hz), 6.64 (1H, m), 6.47 (1 H, d, J 7.8 Hz), 4.79 (1H, br s) and 4.32 (2H, d, J 5.2 Hz).

INTERMEDIATE 2

2-Chloro-4-(4-fluorobenzyl)pyrimidine

4-Fluorobenzylbromide (12.7 g, 67.1 mmol) in THF (35 ml) was added to activated zinc (5.2 g, 80.5 mmol) under nitrogen. After the addition was complete the reaction was refluxed for 15 min. After cooling to room temperature the reaction was treated with tetrakis(triphenylphosphine)palladium (0) (2.27 g, 2 mmol) and 2,4-dichloropyrimidine (10 g, 67.1 mmol). The reaction was heated under reflux for 1 h, then quenched with saturated sodium hydrogen carbonate solution, extracted into dichloromethane, dried over magnesium suphate and concentrated in vacuo. Chromatography (dichloromethane-silica) yielded the itle compound (15.8 g, 88%). $^1$H NMR (CDCl$_3$) δ 8.48 (1H, d, J 6.5 Hz), 7.23 (2H, m), 7.05 (3H, m) and 4.10 (2H, s).

INTERMEDIATE 3

Methyl-3-(2-chloro-4-oynmidinnyl)-3-(4-fluorophenyl)propanoate

Intermediate 2 (5.0 g, 22.5 mmol) in THF (50 ml) was cooled to −78° under nitrogen and treated with sodium bis(trimethylsilyl)amide (1M solution in THF, 24.7 ml, 24.7 mmol). The reaction was stirred at −78° for 15 min, then treated with methyl bromoacetate (3.4 g, 22.5 mmol) in THF (10 ml). After stirring at −78° for 20 min the reaction was allowed to warm to room temperature, quenched with water and extracted into ethyl acetate. After drying over magnesium sulphate the filtrate was concentrated in vacuo and chromatographed (diisopropylether-silica) to yield the title compound (5.57 g, 84%). $^1$H NMR (CDCl$_3$) δ 8.44 (1H, d, J 5.1 Hz), 7.26 (2H, m), 7.06 (1H, d, J 5.1 Hz), 6.70 (2H, t, J 8.6 Hz), 4.54 (1H, dd, J 8.7, 6.0 Hz), 3.62 (3H, s), 3.44 (1H, dd, J 16.7, 8.7 Hz) and 2.90 (1H, dd, J 16.7, 6.5 Hz).

INTERMEDIATE 4

Methyl-3-[2-(4-cyanoanilino)-4-pyrmidionyl]-3-(4-flurorphenyl) prolanoate

Intermediate 3 (4 g, 13.58 mmol) and 4-aminobenzonitrile (1.6 g, 13.58 mmol) in DMF (3 ml) were heated to 1400 for 30 min. The reaction mixture was cooled and partitioned between saturated sodium hydrogen carbonate solution and ethyl acetate, the organic phase was separated, dried over magnesium suphate and concentrated in vacuo. The residual black tar was chromatographed (diisopropylether-silica) to yield the title comrnound as yellow crystals (4.0 g, 78%). $^1$H NMR (CDCl$_3$) δ 8.33 (1H, d, J 3.6 Hz), 7.77 (2H, d, J 8.7 Hz), 7.61 (2H, d, J 8.7 Hz), 7.51 (1H, br s), 7.28 (2H, m), 6.98 (2H, t, J 7.8 Hz), 6.69 (1H, d, J 5.2 Hz), 4.52 (1H, m), 3.60 (3H, s), 3.41 (1H, dd, J 16.5, 8.7 Hz) and 2.91 (1H, dd, J 16.5, 6.9 Hz).

INTERMEDIATE 5

Methyl-3-{2-[4-(aminomethyl)anuilinon]-4-pyrimidinyl}-3-(4-fluorophenyl)propanoate Intermediate 4 (3.85 g, 10.2 mmol) and para-toluenesulphonic acid (2.0 g, 10.2 mmol) in methanol (200 ml) were hydrogenated over 10% palladium on carbon (100 mg) under hydrogen at 50 psi. After 24 h the reaction was filtered, concentrated and the residue partitioned between ethyl acetate and 10% aqueous sodium hydroxide solution. The organic phase was separated, dried over magnesium suphate, evaporated in vacuo and the residue chromatographed (ethyl acetate-silica) to yield the title compound. $^1$H NMR (CDCl$_3$) δ 8.28 (1H, d, J 6.1 Hz), 7.59 (2H, d, J 8.7 Hz), 7.29 (4H, m), 7.09 (1H, br s), 7.00 (2H, m), 6.58 (1H, d, J 6.7 Hz), 4.48 (1H, m), 3.88 (2H, s), 3.62 (3H, s), 3.42 (1H, dd, J 15.6, 7.8 Hz) and 2.91 (1H, dd, J 15.6, 7.8 Hz). MS (ES) m/e 381 [M+H]$^+$.

INTERMEDIATE 6

3-{2-[4-(Aminomethy)anilino]-4-pyrmidinyl}-3-(4-fluorophenyl) propanoic acid

Intermediate 5 (480 mg, 1.26 mmol) and 0.101M sodium hydroxide (12.48 ml, 1.26 mmol) in dioxane (2 ml) and water (5 ml) were heated under reflux for 18 h. The dioxane was removed in vacuo and the remaining aqueous residue neutralised with 1M hydrochloric acid. After removal of the water in vacuo the residue was extracted into methanol, concentrated and washed with water, to yield the title compound (350 mg). $^1$H NMR (CDCl$_3$) δ 9.50 (1H, s), 8.30 (1H, d, J 5.0 Hz), 7.69 (2H, d, J 8.5 Hz), 7.37 (2H, m), 7.25 (2H, d, J 8.6 Hz), 7.10 (2H, t, J 8.9 Hz), 6.77 (1H, d, J 5.1 Hz), 4.42 (1H, m), 3.73 (2H, s), 3.15 (1H, dd, J 16.0, 8.5 Hz) and 2.76 (1H, dd, J 16.3, 6.9 Hz). MS (ES) m/e 367 [M+H]$^+$.

INTERMEDIATE 7

2-Chloro-4-(3,5-difluorobenzyi)pyrimidine

The title compound (4.2 g, 76%) was prepared from 3,5-dichlorobenzylbromide (5.0 g, 24.2 mmol) and 2,4- dichloropyrimidine (3.6 g, 24.2 mmol) in a similar manner to Intermediate 2. $^1$H NMR (CDCl$_3$) δ 8.51 (1H, d, J 5.0 Hz), 7.04 (1H, d, J 5.0 Hz), 6.72 (3H, m) and 4.10 (2H, s). MS (ES) m/e 241 [M+H]$^+$.

INTERMEDIATE 8

Methyl-3-(2-chloro-4-pyrmidinyl)-3-(3,5-difluorophenyl)propanoate

The title compound (4.26 g, 82%) was prepared from Intermediate 7 (4.2 g, 18.3 mmol) in a similar manner to Intermediate 3. $^1$H NMR (CDCl$_3$) δ 8.49 (1H, d, J 5.2 Hz), 7.04 (1H, d, J 5.2 Hz), 6.79 (2H, m), 6.62 (1H, m), 4.50 (1H, dd, J 8.6, 6.3 Hz), 3.60 (3H, s), 3.39 (1H, dd J 8.6, 6.3 Hz), and 2.90 (1H, dd. J 8.6, 6.3 Hz). MS (ES) m/e 313 [M +H]$^+$.

INTERMEDIATE 9

Ethyl-4-[(2-chloro-4-pyromidinyl)methyl]-2-furoate

The title compound (1.65 g, 40%)was prepared from 5-(chloromethyl)-2-furan carboxylate (2.84 g, 15.1 mmol) and 2,4-dichioropyrimidine (2.24 g, 15.1 mmol) in a similar manner to Intermediate 2. $^1$H NMR (CDCl$_3$) δ 8.52 (1H, d, J 5.5 Hz), 7.13 (1H, d, J 5.5 Hz), 7.11 (1H, d, J 5.0 Hz), 6.34 (1H, d, J 5.0 Hz), 4.35 (2H, q, J 7.1 Hz) and 4.20 (2H, s). MS (ES) m/e 267 [M+H]$^+$.

INTERMEDIATE 10 t-Butyl-3-[5-(ethoxycarbonyl)-3-furyl]-3-(2-chloro-4-pyrimdinyl propanoate

The title compound (1.8 g, 79%) was prepared from Intermediate 9 (1.6 g, 6.0 mmol) and t-butyl bromoacetate (879 μl, 6.0 mmol) in a similar manner to Intermediate 3. $^1$H NMR (CDCl$_3$) δ 8.51 (1H, d, J 6.1 Hz), 7.18 (1H, d, J 6.1 Hz), 7.09 (1H, d, J 5.5 Hz), 6.25 (1H, d, J 5.5 Hz), 4.65 (1H, m), 4.32 (2H, m), 3.25 (1H, dd, J 8.6, 6.3 Hz) and 2.95 (1H, dd, J 8.6, 6.3 Hz), 1.35 (9H, s). MS (ES) m/e 403 [M+Na]$^+$.

INTERMEDIATE 11 t-Butyl-3-(2-chloro-4-pyrimidinyl)-3-[4-fluorophenyl]propanoate

The title compound (4.5 g, 80%) was prepared from Intermediate 2 (3.26 g, 16.76 mmol) in a similar manner to Intermediate 10. $^1$H NMR (CDCl$_3$) δ 8.44 (1H, d, J 6.0 Hz), 7.30–7.21 (2H,m), 7.08–6.97 (3H, m), 4.49 (1H, t, J 8.0 Hz), 3.32 (1H, d, J 8.2 Hz), 2.84 (1H, d, J 8.2 Hz) and 1.35 (9H, s).

INTERMEDIATE 12

Ethyl-3-(2-chloro-4-pyrimidinyl)propanoate

To a stirred solution of zinc bromide (12.39 g, 55 mmol) in diethyl ether (150 ml) at room temperature under a nitrogen atmosphere was added 1-ethoxycyclopropyloxy trimethylsilane (8.72 g, 10 ml, 50 mmol). The reaction mixture was refluxed for 1 h. Upon cooling to room temperature THF (300 ml) was added. 2,4-Dichloropyrimidine (7.45 g, 50 mmol) was added as a solution in THF (100 ml), followed by tetrakis(triphenylphosphine) palladium (0) (1.156 g, 1.0 mmol) as a solution in THF (50 ml). The reaction mixture was heated under reflux for 3 h. Upon cooling, the reaction mixture was partitioned between saturated sodium bicarbonate solution (500 ml) and dichloromethane (500 ml). The aqueous layer was further washed with dichloromethane (100 ml) and the combined organic fractions dried over magnesium sulphate, filtered and the solvent removed by evaporation in vacuo. The title compound was isolated after purification by flash column chromatography (1:1 diethyl ether, hexane-silica) as a colourless oil (7.83 g, 73%); $^1$H NMR (CDCl$_3$) δ 8.49 (1H, d, J 5.0 Hz), 7.18 (1H, d, J 5.0 Hz), 4.13 (2H, q, J 7.0 Hz), 3.09 (2H, t, J 7.0 Hz), 2.83 (2H, t, J 7.0 Hz) and 1.25 (3H, t, J 7.0 Hz).

INTERMEDIATE 13

Ethyl-3-(2-[4-{(2-pyridinylamino)methyl}phenoxy]-4-pyrimidinyl) propanoate

To a stirred solution of Intermediate 1 (1.0 g, 5 mmol) in THF (20 ml) was added in a single portion sodium hydride (60% dispersion in mineral oil, 0.2 g, 5 mmol). The reaction mixture was stirred for 30 min at room temperature. Intermediate 12 (1.07 g, 5 mmol) was added as a solution in THF (10 ml). The reaction mixture was heated to reflux for 3 h. Upon cooling the reaction mixture was poured onto saturated sodium bicarbonate solution (50 ml) and extracted twice with dichloromethane (50 ml). The combined organic fractions were dried over magnesium sulphate, filtered and the solvent removed by evaporation in vacuo. Purification was by flash column chromatography (diethyl ether-silica) giving the title compound (0.95 g, 50%). $^1$H NMR (CDCl$_3$) δ 8.39 (1H, d, J 5.0 Hz), 8.16–8.10 (1H, m), 7.48–7.39 (3H, m), 7.20–7.15 (2H, m), 6.93 (1H, d, J 5.0 Hz), 6.61 (1H, dd, J 6.5, 1.0 Hz), 6.42 (1H, d, J 6.0 Hz), 4.92 (1 H, br s), 4.58 (2H, d, J 6.0 Hz), 4.12 (2H, q, J 8.0 Hz), 3.08 (2H, t, J 830 Hz), 2.54 (2H, t, J 8.0 Hz) and 1.27 (3H, t, J 8.0 Hz).

INTERMEDIATE 14

Ethyl-3-(2-chloro-4-pyrimidinyl)propanoate

To a stirred solution of borane dimethyl sulphide complex (1.42 ml, 15 mmol) in THF at 0° was added dropwise α-pinene (5 ml, 31.5 mmol). The reaction mixture was stirred at room temperature for 30 min. The reaction mixture was cooled to –35° and ethyl propionate (1.47 g, 1.52 ml, 15 mmol) added dropwise. The reaction mixture was stirred at room temperature for 2 h and then cooled to 0°. Acetaldehyde (5 ml, 3.94 g, 89 mmol) was added dropwise. The reaction mixture was heated to reflux for 1 h. Upon cooling the solvent and volatiles were removed by evaporation in vacuo. The residue was dissolved in THF (50 ml) and pinacol (1.8 g, 18 mmol) added. The reaction mixture was stirred for 1 h at room temperature. The solvent and volatiles were removed by evaporation in vacuo. To the crude product was added 2,4-dichloropyrimidine (2.24 g, 15 mmol) followed by cesium fluoride (4.56 g, 30 mmol) and tetrakis (triphenylphosphine)palladium (0) (0.88 g, 0.75 mmol). The reaction mixture was diluted with dioxane (50 ml) and heated under reflux for 3 h. Upon cooling the reaction mixture was poured into saturated sodium hydrogen carbonate solution (100 ml) and extracted twice with dichloromethane (100 ml). The combined organic fractions were dried over magnesium sulphate, filtered and the solvent removed by evaporation in vacuo. Purification by flash column chromatography (diisopropylethersilica) gave the title compound (1.59 g, 50%). $^1$H NMR (CDCl$_3$) δ 6.78 (1H, d, J 12 Hz), 6.62 (1H, d, J 12 Hz), 4.22 (2H, q, J 8 Hz) and 1.21 (3H, t, J 8 Hz).

INTERMEDIATE 15

Ethyl-3-(2-[-{(2-pyridinylamino)methyl}phenoxyl-4-pyrimidinyl) propanoate

To a stirred solution of Intermediate 14 (0.17 g, 0.8 mmol) and Intermediate 1 (0.18 g. 0.9 mmol) in DMF (5 ml) was added in a single portion cesium carbonate (0.167 g, 0.5 mmol) the reaction mixture was heated under reflux for 4 h. Upon cooling the reaction mixture was poured onto saturated sodium hydrogen carbonate solution (2.0 ml) and the product extracted twice with dichloromethane (20 ml). The combined organic fractions were dried over magnesium sulphate, filtered and the solvent removed by evaporation in vacuo. Purification by flash column chromatography (diethyl ether-silica) gave the title compound (0.02 g, 7%). $^1$H NMR (CDCl$_3$) δ 8.59 (1H, d, J 6 Hz), 8.08 (1H, br s), 7.49 (1H, d, J 16 Hz), 7.43 (2H, d, J 8 Hz), 7.52–7.4 (1H, m), 7.19 (2H, d, J 8 Hz), 7.07 (1H, d, J 6 Hz), 7.01 (1H, d, J 16 Hz), 6.62 (1H, br t, J 8 Hz), 6.45 (1H, br d, J 6 Hz), 4.55 (2H, br d, J 6 Hz), 4.29 (2H, q, J 8 Hz) and 1.31 (3H, t, J 8 Hz).

INTERMEDIATE 16

2-Chloro-4-(4-cyanobenzyl)pyrimidine

The title compound (1.5 g, 32%) was prepared from p-cyanobenzyl bromide (4.0 g, 2.04 mmol) in a similar manner to Intermediate 2 and used crude in the next step.

INTERMEDIATE 17 t-Butyl-3-(2-chloro-4-pyrimidinyl)-3-(4-cyanophenyl)propanoate

The title compound (1.6 g, 72%) was prepared from Intermediate 16 (1.5 g, 6.5 mmol) in a similar manner to Intermediate 10. $^1$H NMR (CDCl$_3$) δ 8.49 (1H, d, J 5.2 Hz), 7.61(2H, d, J 8.2 Hz), 7.42 (2H, d, J 8.2 Hz), 7.08 (1 H, d, J 5.2 Hz), 4.53 (1H, t, J 7.2 Hz), 3.35 (1H, dd, J 17, 8.2 Hz), 2.88 (1 H, dd, J 17, 7.2 Hz) and 1.38 (9H, s). MS (ES) m/e 344 [M+H]$^+$.

INTERMEDIATE 18

4-Benzyloxy-N'-(2-pyridinyl)benzamide

4-Benzyloxybenzoic acid (1.0 g, 4.38 mmol) was stirred overnight in dichloromethane (200 ml) with EDC (640 mg, 5.25 mmol) DMAP (2.44 mg, 2 mmol), 2-aminopyridine (412.2 mg, 4.38 mmol) and N-methyl morpholine (1 ml, 9 mmol). After this time the reaction was partitioned between dichloromethane (200 ml) and saturated sodium bicarbonate solution (200 ml) and the organics dried over magnesium sulphate. The solvents were removed in vacuo and the crude oil columned (ethyl acetate-silica) to yield the title compound (370 mg, 28%). $^1$H NMR (CDCl$_3$) δ 8.50 (1H, d, J 8.5 Hz), 8.30 (IH, d, J 8.2 Hz), 7.99 (2H, d, J 8.7 Hz), 7.84 (1H, dd, J 15.8, 7.2 Hz), 7.48–7.35 (5H, m), 7.16–7.02 (3H,m), 5.14 (2H, s). MS (ES) m/e 305 [M+H]$^+$.

INTERMEDIATE 19

4-Hydroxy-N'-(2-pyridinyl)benzamide

Intermediate 18 (370 mg, 1.21 mmol) was dissolved in ethanol (100 ml) and 10% palladium on carbon (1 g) added. The mixture was stirred under a hydrogen atmosphere for 5 h at room temeprature. After this time the mixture was filtered through Celite®, and the plug was washed with dichloromethane (2×100 ml). The combined washings were concentrated in vacuo to give the title compound (220 mg, 85%). $^1$H NMR (CDCl$_3$) δ 8.32 (1H, d, J 8.5 Hz), 7.86–7.75 (3H, m), 7.20–7.01 (1 H, m), 6.95–6.81 (2H, m). MS (ES) m/e 215 [M+H]$^+$.

INTERMEDIATE 20 t-Butyl-3-(4-fluorophenyl)-3-(2-[4-cyanophenoxy]-4-pyrimidinyl)propanoate

The title compound (5.1 g, 81%) was prepared from 4-cyanophenol (1.77 g, 14.9 mmol) and Intermediate 11 (5.0 g, 14.8 mmol)in a similar manner to Intermediate 13. $^1$H NMR (CDCl$_3$) δ 8.41 (1H, d, J 8.6 Hz), 7.58 (2H, d, J 9.2 Hz), 7.42 (2H, d, J 9.2 Hz), 7.22–7.12 (2H, m), 6.98-6.89 (3H, m), 4.48–4.40 (1H, m), 3.38–3.25 (1H, m), 2.88–2.71 (1H, m) and 1.29 (9H, s). MS (ES) m/e 420 [M+H]$^+$.

INTERMEDIATE 21 t-Butyl-3-(2-[4-aminomethylphenoxy)]4-pyremidinyl)-3-(4-fluorophenyl)propanoate

Raney® nickel (1 g) was washed with water (3×100 ml) and ethanol (2×100 ml). The metal was suspended in ethanol (150 ml) and concentrated ammonia solution (4 ml) and Intermediate 20 (5.1 g, 12.1 mmol) in ethanol (10 ml) added. The mixture was rapidly stirred under a hydrogen atmosphere for 3 h. The solution was filtered through Celite® and the plug washed with dichloromethane (3×100 ml). The solvent was removed in vacuo to yield the title compound as a yellow gum (4.4 g, 85%). $^1$H NMR (CDCl$_3$) δ 8.21 (1H, d, J 5.8 Hz), 7.41 (2H, d, J 8.6 Hz), 7.28–7.22 (2H, m), 7.12 (2H, d, J 8.6 Hz), 6.98–6.85 (2H, m), 6.68 (1H, d, J 5.8 Hz), 4.41 (1H, t, J 7.8 Hz), 3.98 (2H, s), 3.25–3.18 (1H, m), 2.82–2.68 (1H, m) and 1.28 (9H, s). MS (ES) m/e 424 [M+H]$^+$.

INTERMEDIATE 22 t-Butyl-3-(2-[4-{(4-nitro-2-pyridinyl)amino}methyl]phenoxy)-4-pyrimidinyl)-3-(4-fluorophenyl)propanoate The title compound (5.70 g, 70%) was prepared from Intermediate 21 (634 mg, 1.49 mmol) potassium carbonate (205 mg, 1.49 mmol) and 2-chloro-4-nitropyridine (237 mg, 1.49 mmol) in a similar manner to Intermediate 15. $^1$H NMR (CDCl$_3$) δ 9.10 (1H, s), 8.32 (1H, d, J 5.2 Hz), 8.19 (1H, d, J 8.2 Hz), 7.41 (2H, d, J 8.1 Hz), 7.20–7.15 (4H, m), 7.07–6.85 (3H, m), 6.41 (1H, d, J 8.4 Hz), 4.69 (2H, s), 4.42 (1H, t, J 7.2 Hz), 3.21 (1H, dd, J 15.2, 8.1 Hz), 2.81 (1H, dd, J 15.3, 7.9 Hz) and 1.31 (9H, s). M/S (ES) m/e 546 [M+H]$^+$.

INTERMEDIATE 23 t-Butl-3-[2-(4-{[(4-amino-2-pyridindyl)amino]methyl}phenoxy)-4-pyrimidinyl]-3-(4-fluorophenyl)propanoate Intermediate 22 (450 mg, 0.82 mmol) in ethanol (100 ml) was stirred with 10% palladium on carbon (1 g) under an atmosphere of hydrogen for 1 h. The solution was filtered through a plug of Celite® and concentrated in vacuo to give the title compound as a red gum (422 mg, 100%). $^1$H NMR (CDCl$_3$) δ 8.35 (1H, d, J 5.2 Hz), 7.60 (1H, s), 7.41 (2H, d, J 8.3 Hz), 7.28–7.19 (2H, m), 7.15 (2H, d, J 8.1 Hz), 7.10 (1H, d, J 7.2 Hz), 6.92–6.89 (2H, m), 6.81 (1H, d, J 5.2 Hz), 6.39 (1H, d, J 7.2 Hz), 4.49 (2H, s), 4.42 (1H, t, J 7.2 Hz), 3.21 (1H, dd, J 15.3 Hz, 8.1 Hz), 2.78 (1H, dd, J 15.3, 7.9 Hz), 1.31 (9H, s). MS (ES) m/e 516 [M+H]$^+$.

INTERMEDIATE 24 t-Butyl-3-(2-[4-{(1H-1,3-benzimidazol-2-yl-amino)methyl}phenoxy]-4-pyrimidinyl)-3-(4-fluornphenyl)propanoate 1,1-Thiocarbonyl diimidazole (629 mg, 3.54 mmol), imidazole (48 mg, 0.7 mmol) and Intermediate 21 (1.0 g, 2.36 mmol) were stirred at 0° in acetonitrile (100 ml) for 1 h then warmed to room temperature and stirred for 3 h. Phenylenediamine (509 mg, 4.72 mmol) was added and the mixture was stirred at 500 for 3 h. After this time the mixture was stirred at ambient temperature overnight. At this point the solvents were removed in vacuo and the crude foam heated in ethanol (100 ml) with red mercuric oxide (368 mg, 1.7 mmol) and sulphur (3 mg, 0.087 mmol) at reflux overnight. The mixture was cooled, filtered and the solvent removed in vacuo. The crude gum was subjected to column chromatography (ethyl acetate-silica) to yield the title compound as cream foam (550 mg, 43%). $^1$H NMR (CDCl$_3$) δ 8.20 (1H, d, J 5.2 Hz), 7.45–7.10 (8H, m), 7.12–6.82 (4H, m), 6.81–6.72 (1H, d, J 5.2 Hz), 4.70–4.62 (2H, m), 4.41 (1H, t, J 7.2 Hz), 3.12 (1H, dd, J 16.1, 7.1 Hz), 2.65 (1H, dd, J 15.8, 7.2 Hz) and 1.38 (9H, s). MS (ES) m/e 541 [M+H]$^+$.

INTERMEDIATE 25 t-Bulyl-3-[2-(4-cyanobenzyl)-4-pyrimidinyl]-3-(4-fluorophenyl) propanoate

Activated zinc (507 mg, 7.8 mmol) was suspended in THF (5 ml) and 4-cyanobenzylbromide (1.27 g, 6.5 mmol) in THF (5 ml) was added and the mixture refluxed for 30 min. Tetrakis(triphenylphosphine) palladium (0) (200 mg) and Intermediate 11 (2.19 g, 6.5 mmol) in THF (10 ml) were added and the mixture refluxed for 3 h. After cooling the mixture was partitioned between ethyl acetate (100 ml) and 10% ammonium chloride solution (100 ml) and the organics dried over magnesium sulphate. The solvent was removed in vacuo and the crude solid subjected to column chromatography (diisopropyl ether→ethyl acetate-silica) to yield the title compound as a yellow oil (2.2 g, 81%). $^1$H NMR (CDCl$_3$) δ 8.42 (1H, d, J 5.2 Hz), 7.58 (2H, d, J 8.6 Hz), 7.42 (2H, d, J 8.6 Hz), 7.20–7.12 (2H, m), 6.99–6.87 (3H, m), 4.48–4.40 (1H, m), 4.36 (2H, s), 3.27 (1H, dd, J 16.2, 8.9 Hz), 2.81 (1H, dd, J 16.2, 8.5 Hz) and 1.28 (9H, s). MS (ES) m/e 418 [M+H]$^+$.

INTERMEDIATE 26 t-Butyl-3-(2-[4-{aminomethyl}benzyl]-4-pyrimidinyl)-3-(4-fluorophenyl) propanoate The title compound (1.4 g, 64%) was prepared from Intermediate 25 (2.2 g, 5.2 mmol) in a similar manner to Intermediate 21. $^1$H NMR (CDCl$_3$) δ 8.42 (1H, d, J 5.2 Hz), 7.32 (2H, d, J 8.2 Hz), 7.22–7.15 (4H, m), 6.98–6.85 (3H, m), 4.42 (1H, t, J 8.4 Hz), 4.25 (2H, s), 3.79 (2H, s), 3.3 (1H, dd, J 16.2, 8.4 Hz), 3.32 (1H, dd, J 16.2, 8.4 Hz) and 1.28 (9H, s). MS (ES) m/e 422 [M+H]$^+$.

INTERMEDIATE 27 t-Butyl-3-(2-[4-([{N,N'-bis-boc((amino)imino)methyl}amino]methyl) phenoxy]-4-oyrimidinyl)-3-(4-fluorophenyl)pronanoate Intermediate 21 (200 mg, 0.49 mmol), N,N'-bis-boc-guanyl triflate (192 mg, 0.46 mmol) and triethylamine (70.7 ml, 0.49 mmol) were stirred in dichloromethane (10 ml) fo 12 h. The organics were then washed with saturated sodium bicarbonate solution (20 ml) and dried over magnesium sulphate. The solvent was removed in vacuo to yield a white foam (300 mg, 92%). $^1$H NMR (CDCl$_3$) δ 8.68–8.61 (1H, br m), 8.38 (1H, d, J 5.2 Hz), 7.38 (2H, d, J 8.6 Hz), 7.29–7.21 (2H, m), 7.18 (2H, d, J 8.6 Hz), 7.13–4.92 (2H, m), 6.82 (1H, d, J 5.2 Hz), 4.62 (2H, d, J 5.4 Hz), 4.43 (1H, t, 7.4 Hz), 3.25 (1 H, dd, J 16.5, 7.4 Hz), 2.78 (1H, dd, J 10.5, 7.4 Hz), 1.58 (9H, s), 1.59 (9H, s) and 1.28 (9H, s). MS (ES) m/e 665 [M+H]$^+$.

INTERMEDIATE 28

2-Ethoxyethyl-3-(2-[4-cyanoanilino]-4-pyrimidinyl)-3-(4-fluorophenyl) propanoate 4-Amino-benzonitrile (1.58 g, 13.37 mmol) and Intermediate 11 (4.5 g, 13.37 mmol) were dissolved in ethoxyethanol (50 ml) and the reaction mixture was heated under reflux for 3 h. Upon cooling the reaction mixture was poured into saturated sodium hydrogen carbonate solution (10 ml) and the product extracted twice with dichloromethane (100 ml). The combined organic fractions were dried over magnesium sulphate, filtered and the solvent removed by evaporation in vacuo. Purification by flash column chromatography (2:1 diethyl ether, hexane-silica) gave the title compound (3.2 g, 55%). $^1$H NMR (CDCl$_3$) δ 8.31 (1H, d, J 6.0 Hz), 7.78 (2H, d, J 10.0 Hz), 7.62 (2H, d, J 10.0 Hz), 7.58 (1H, br s), 7.23 (2H, t, J 8.0 Hz), 7.02 (2H, t, J 8.0 Hz), 6.66 (1H, d, J 6.0 Hz), 4.53 (1H, dd, J 8.0, 2.0 Hz), 4.28–4.12 (2H, m), 3.60–3.53 (2H, m), 3.48 (2H, q, J 8.0 Hz), 3.43 (1H, dd, J 16.0, 8.0 Hz), 2.92 (1H, dd, J 18.0, 8.0 Hz) and 1.21 (3H, t, J 8.0 Hz).

INTERMEDIATE 29

2-Ethoxyethyl-3-(2-[4-{aminomethyl}anilino]-4-pyrimidinyl)-3-(4-fluorophenyl)propanoate The title compound (1.05 g, 32%), purified by flash chromatography (20% methanol, 80% dichloromethane, silica) was prepared from Intermediate 28 (3.2 g, 7.35 mmol) in a similar manner to Intermediate 21. $^1$H NMR (CDCl$_3$) δ 8.23 (1H, d, J 5.0 Hz), 7.58 (2H, d, J 8.0 Hz), 7.35–7.20 (5H, m), 6.99 (2H, t, J 9.0 Hz), 6.52 (1H, d, 1 5.0 Hz), 4.50–4.42 (1H, m), 4.17 (2H, 5.0 Hz), 3.60–3.38 (5H, m), 2.92 (1H, dd, J 16.0, 7.0 Hz) and 1.18 (3H, t, J 7.0 Hz). MS (ES) m/e 439 [M+H]$^+$.

INTERMEDIATE 30

2-Ethoxyethyl-3-(4-fluorophenyl)-3-(2-[4-{(2-pyridinylamino)methyl}anilino]-4-pyrimidinyl) propanoate A stirred solution of the compound of Intermediate 29 (0.438 g, 1.0 mmol) in 2-fluoropyridine (10 ml) was heated to reflux for 4 h. Upon cooling the reaction mixture was poured onto saturated sodium hydrogen carbonate solution (50 ml) and extracted twice with dichloromethane (50 ml). The combined organic fractions were dried over magnesium sulphate, filtered and the solvent removed by evaporation in vacuo. Purification by flash column chromatography (diethyl ether-silica) gave the title compound (0.18 g, 38%). $^1$H NMR (CDCl$_3$) δ 8.21 (1H, d, J 6.0 Hz), 8.12 (1H, d, J 4.0 Hz), 7.62 (1H, br s), 7.58 (2H, d, J 8.0 Hz), 7.42 (1H, t, J 7.0 Hz), 7.33 (2H, d, 1 8.0 Hz), 7.31–7.22 (2H, m), 6.99 (1H, t, J 9.0 Hz), 6.59 (1H, dd, J 8.0, 1.0 Hz), 6.53 (1H, d, J 6.0 Hz), 6.39 (1H, d, 19.0 Hz), 5.12 (1H, br s), 4.50–4.43 (3H, m), 4.18 (2H, t, J 6.0 Hz), 3.58–3.36 (5H, m), 2.93 (1H, dd, J 16.0, 8.0 Hz) and 1.18 (3H, t, J 7.0 Hz).

INTERMEDIATE 31

2-Chloro-4-benzyl pyrimidine

The title compound (quantitiative yield) was prepared from benzyl bromide (1.71 g, 1.19 ml, 10 mmol) and 2,4-dichloropyrimidine (1.49 g, 10 mmol) in a similar manner to Intermediate 2, and was used without purification.

INTERMEDIATE 32 t-Butyl-3-(2-chloro-4-pyrimidinyl)-3-phenyl propanoate

The title compound (3.9 g, 97%) was prepared from Intermediate 31 (2.70 g, 12.5 mmol) in a similar manner to Intermediate 10. $^1$H NMR (CDCl$_3$) δ 8.41 (1H, d, J 5.2 Hz), 7.35–7.15 (5H, m), 7.54 (1H, d, J 5.2 Hz), 4.58–4.42 (1H, m), 3.28 (1H, dd, J 16.4, 8.1 Hz), 2.85 (1H, dd, J 16.4, 7.5 Hz) and 1.38 (9H, s). MS (ES) m/e 319 [M+H]$^+$.

INTERMEDIATE 33 t-Butyl-3-phenyl-3-(2-[4-{(2-pyrdinylamino) methyl}phenoxyl]-4-pyrimidinyl)propanoate The title compound (1.2 g, 49%) was prepared from Intermediate 1 (1.00 g, 5 mmol) and Intermediate 32 (1.59 g, 5 mmol) in a similar manner to Intermediate 13. $^1$H NMR (CDCl$_3$) δ 8.34 (1H, d, J 5.2 Hz), 7.48–7.39 (3H, m), 7.35–7.12 (7H, m), 6.87 (1H, d, J 5.2 Hz), 6.63–6.56 (1H, m), 6.39 (1H, d, J 8.2 Hz), 4.90 (1H, bs), 4.55 (2H, d, J 8.1 Hz), 4.45 (1H, t, J 8.2 Hz), 3.31 (1H, dd, J 16.2, 8.1 Hz), 2.78 (1H, dd, J 16.1, 7.9 Hz) and 1.30 (9H, s). MS (ES) m/e 483 [M+H]$^+$.

INTERMEDIATE 34

Methyl-4-[(2-Chloro-4-pyrimidinyl)methyl]-4-benzoate

The title compound (4.35 g, 63%) was prepared from methyl (4-bromomethyl)benzoate (5.0 g, 21.8 mmol) in a similar manner to Intermediate 2. $^1$H NMR (CDCl$_3$) δ 8.51 (1H, d, J 5.1 Hz), 8.03 (2H, d, J 8.4 Hz), 7.35 (2H, d, J 8.3 Hz), 7.03 (1H, d, J 5.1 Hz), 4.15 (2H, s) and 3.91 (3H, s). MS (ES) m/e 263 [M+H]$^+$.

INTERMEDIATE 35 t-Butyl-3-(2-chloro-4-pyrimidinyl)-3-[4-(methoxycarbonyl)pheny]propanoate

The title compound (4.34 g, 69%) was prepared from Intermediate 34 (4.36 g, 16.6 mmol) in a similar manner to Intermediate 10. $^1$H NMR (CDCl$_3$) δ 8.41 (1H, d, J 6.2 Hz), 7.95 (2H, d, J 8.6 Hz), 7.05 (2H, d, J 8.6 Hz), 7.12 (1H, d, J 6.2 Hz), 4.57 (1H, t, J 7.8 Hz), 3.87 (3H, s), 3.48–3.32 (1H, m), 2.91–2.81 (1H, m) and 1.29 (9H, s). MS (ES) m/e 378 [M+H]$^+$.

INTERMEDIATE 36 t-Butyl-3-[4-(methoxycarbonyl)phenyl]-3-(2-{4-[(2-pynridinylamino) methyl]phenoxy}-4-pyrimidinyl) propanoate The title compound (350 mg, 27%) was prepared from Intermediate 1 (500 mg, 2.5 mmol) and Intermediate 35 (941 mg, 2.5 mmol) in a similar manner to Intermediate 13. $^1$H NMR (CDCl$_3$) δ 8.38 (1H, d, J 6.4 Hz), 8.10 (1H, d, J 5.2 Hz), 7.89 (2H, d, J 8.6 Hz), 7.48–7.30 (5H, m), 6.59 (1H, t, J 5.2 Hz), 6.43 (1H, d, J 6.4 Hz), 4.59 (2H, d, J 5.2 Hz), 4.47 (1H, t, J 5.2 Hz), 3.80 (3H, s), 3.31–3.28 (1H, m), 2.91–2.72 (1H, m) and 1.28 (9H, 2). MS (ES) m/e 541 [M+H]$^+$.

INTERMEDIATE 37 t-Butyl-3-([N'-butoxycarbonyl{2-aminoethyl}]4-benzamide)-3-(2-[4-{(2-pyridinylamino) methyl}phenoxy]-4-pyrimidinyl)propanoate The compound of Example 19 (1.0 g, 1.9 mmol) in DMF (70 ml) was treated with N-bocethylenediamine (0.5 g, 2.9 mmol), diisopropylethylamine (0.37 g, 2.9 mmol), EDC (0.55 g, 2.9 mmol), 1-hydroxy-7-azabenzatriazole (0.39 g, 2.9 mmol) and stirred at room temperature overnight. Water was then added to the reaction and the mixture extracted into ethyl acetate. The organic layer was dried over magnesium sulphate and reduced in vacuo to an orange gum (1.1 g, 86%). $^1$H NMR (CDCl$_3$) δ 8.36 (1H, d, J 5.1 Hz), 8.19 (1H, m), 8.02 (1H, s), 7.70 (2H, d, J 8.4 Hz), 7.42 (3H, m), 7.30 (2H, d, J 8.2 Hz), 7.12 (2H, d, J 8.4 Hz), 6.85 (1H, d, J 5.1 Hz), 6.59 (1H, m), 6.41 (1H, d, J 8.4 Hz), 5.02 (1H, br m), 4.55 (2H, d, J 5.8 Hz), 4.47 (1H, m), 3.53 (2H, m), 3.43 (2H, m), 3.20 (1H, dd, J 8.6, 6.7 Hz), 2.82 (1H, dd, J 7.0, 6.3 Hz), 1.42 (9H, s) and 1.32 (9H, s). MS (ES) m/e 669 [M+H]$^+$.

INTERMEDIATE 38 t-Butyl-3-[2-(4-cyano-N-methylanilinol-4-pyrimidinyl]-3-(4-fluoroDhenyl)propanoate A mixture of 4-(N-methylamino)benzonitrile (1.189, 8.92 mmol) Intermediate 11 (2.0 g, 5.96 mmol) sodium t-butoxide (856 mg, 8.92 mmol) and Pd (dppf)$_2$Cl$_2$ (212 mg, 0.29 mmol) in THF (12 ml) were stirred at 80° for 8 h. The reaction was cooled, quenched with water and extracted into dichloromethane, dried over sodium sulphate and evaporated in vacuo. Purification by flash chromatography (4:1→3:2 hexane, diethyl ether-silica) gave the title compound (2.29, 85%) $^1$H NMR (CDCl$_3$) δ 8.20 (1H, d, J 5.0 Hz), 7.61 (2H, d, J 8.6 Hz), 7.46 (2H, d, J 8.6 Hz), 7.20 (2H, dd, J 8.6, 5.4 Hz), 6.94 (2H, t, J 8.6 Hz), 6.54 (1H, d, J 5.0 Hz), 4.33 (1H, dd, J 8.7, 6.9 Hz), 3.60 (3H, s), 3.17 (1H, dd, J 15.9, 8.7 Hz), 2.72 (1H, dd, J 15.9, 6.9 Hz) and 1.29 (9H, s). MS (ES) m/e 433 [M+H]$^+$.

INTERMEDIATE 39 t-Butyl-3-[2-(4-aminomethyl-N-methylanilino)-4-gyrimidinyl]-3-(4-fluororhenyl)propanoate The title compound (1.6 g, 72%) was prepared from Intermediate 38 (2.2 g, 5.04 mmol) in a similar manner to Intermediate 21. $^1$H NMR (CDCl$_3$) δ 8.12 (1H, d, J 5.0 Hz), 7.35 (2H, d, J 8.3 Hz), 7.28–7.20 (4H, m), 6.96 (2H, t, J 8.7 Hz), 6.39 (1H, d, J 5.0 Hz), 4.30 (1H, dd, J 8.4, 7.3 Hz), 3.90 (2H, s), 3.55 (3H, s), 3.21 (1H, dd, J 15.9, 8.4 Hz), 2.75 (1H, dd, J 15.9, 7.3 Hz) and 1.31 (9H, s). MS (ES) m/e 437 [M+H]$^+$.

INTERMEDIATE 40 t-Butyl-3-[2-4-{N,N'-bis-boc-({amino(imono) methyl}amino)methyl}-N-methylanilino)-4-pyromidinyl]-3-(4-fluorophenyl)propanoate The title compound (825 mg, 68%) was prepared from Intermediate 39 (800 mg, 1.8 mmol) in a similar manner to Intermediate 27. $^1$H NMR (CDCl$_3$) δ 8.63 (1H, br s), 8.16 (1H, dd, J 5.0 Hz), 7.46–7.23 (6H, m), 6.96 (2H, t, J 8.2 Hz), 6.42 (1H, d, J 5.0 Hz), 4.65 (2H, d, J 5.1 Hz), 4.30 (1H, dd, J 8.5, 7.1 Hz), 3.56 (3H, s), 3.20 (1H, dd, J 15.9, 8.5 Hz), 2.75 (1H, dd, J 15.9, 7.1 Hz), 1.53 (9H, s), 1.49 (9H, s) and 1.31 (9H, s). MS (ES) m/e 679 [M+H]$^+$.

INTERMEDIATE 41 t-Butyl-3-{2-[4-(aminomethyl)phenoxy]-4-pyrimidionyl]-3-(4-fluoronhenyl)propanoate The title compound (1.3 g, 38%) was prepared from 4-hydroxybenzylamine (1.0 g, 8.14 mmol) and Intermediate 11 (2.7 g, 8.14 mmol) in a similar manner to Intermediate 13. $^1$H NMR (CDCl$_3$) δ 8.13 (1H, d, J 5.2 Hz), 7.54 (2H, d, J 7.8

Hz), 7.24 (2H, dd, J 7.8, 6.9 Hz), 7.09 (2H, d, J 7.8 Hz), 6.99 (2H, t, J 7.8 Hz), 6.81 (1H, d, J 5.2 Hz), 4.43 (1H, t, J 6.9 Hz), 4.09 (2H, br s), 3.23 (1H, dd, J 16.5, 7.8 Hz), 2.79 (1H, dd, J 16.5, 6.9 Hz) and 1.29 (9H, s).

INTERMEDIATE 42 t-Butyl-3-(4-fluoroohenyl)-2-(2-{4-[(3,4,5,6-tetrahydro-2H-azepin-7-ylamino)methyl]phenoxy}-4-pyrimidinyl)propanoate Intermediate 41 (250 mg, 0.59 mmol) in acetonitrile (2 ml) was treated with 1-aza-methoxy-1-cycloheptene (75 mg, 0.59 mmol) and heated under reflux overnight. The solvent was removed in vacuo and the residue crystallised from diisopropylether, further purification by reverse phase chromatography (70% ethanol, 30%water-reverse phase silica) yielded the title compound (200 mg). $^1$H NMR (d$^6$ DMSO) δ 10.35 (1H, br s), 8.53 (1H, d, J 5.0 Hz), 7.63 (1H, d, J 8.5 Hz), 7.44 (1H, dd, J 8.7, 5.5 Hz), 7.29 (1H, d, J 5.0 Hz), 7.24–7.14 (4H, m), 4.76 (2H, s), 4.58 (1H, t, J 7.1 Hz), 3.60–3.57 (2H, m), 3.22 (1H, dd J 15.9, 8.8 Hz), 2.98–2.83 (3H, m), 1.82–1.69 (4H, br m), 1.691.59 (2H, br m) and 1.30 (9H, s).

INTERMEDIATE 43

4-Benzyloxybenzylalcohol

4-Benzyloxybenzaldehyde (5 g, 23.6 mmol) in ethanol (50 ml) was treated with sodium borohydride (450 mg, 11.8 mmol) and stirred at room temperature for 1 h. The reaction was quenched with 10% hydrochloric acid, the ethanol removed in vacuo and the aqueous residue extracted into dichloromethane, dried over magnesium sulphate and concentrated in vacuo. Chromatography (dichloromethane-silica) yielded the t compound (5.1 g). $^1$H NMR (CDCl$_3$) δ 7.48–7.25 (7H, m), 6.98 (2H, d, J 8.5 Hz), 5.10 (2H, s) and 4.52 (2H, s).

INTERMEDIATE 44

4-Benzyloxybenzylchloride

Intermediate 43 (1 g, 4.67 mmol) in dichloromethane (5 ml) was treated with thionyl chloride (0.34 ml, 4.59 mmol) and stirred at room temperature for 20 min. The reaction was concentrated in vacuo yielding the title compound (1.0 g). $^1$H NMR (CDCl$_3$) δ 7.45–7.32 (5H, m), 7.31 (2H, d, J 8.5 Hz), 6.98 (2H, d, J 8.5 Hz), 5.09 (2H, s) and 4.59 (2H, s).

INTERMEDIATE 45

1-(4-Benzyloxyphenylmethyl)-1H-imidazole

Intermediate 44 (1 g, 4.67 mmol) in DMF (10 ml) was treated with imidazole (635 mg, 9.34 mmol) and stirred at room temperature 2 h then heated under reflux for 1 h. The solvent was removed in vacuo and the residue partitioned between water and dichloromethane, the organic phase was separated, dried over magnesium sulphate and concentrated in vacuo. The resulting oil was chromatographed (94% ethyl acetate, 5% methanol, 1% triethylamine-silica) yielding the title compound (0.8 g, 65%). $^1$H NMR (CDCl$_3$) δ 7.53 (1H, s), 7.46–7.30 (5H, m), 7.10 (3H, m), 6.96 (2H, d, J 8.5 Hz), 6.89 (1H, s), 5.08 (2H, s) and 5.03 (2H, s).

INTERMEDIATE 46

1-(4-Hydroxylhenylmethyl)-1H-imidazole

Intermediate 45 (750 mg, 2.84 mmol) in THF (20 ml), ethanol (2 ml) and water (2 ml) was treated with hydrochloric acid (0.3 ml) and was hydrogenated at atmospheric pressure over 10% palladium on carbon (100 mg). After 2 h the catalyst was removed by filtration and the filtrate concentrated in vacuo yielding the title compound (545 mg). $^1$H NMR (CDCl$_3$) δ 8.7 (1H, s), 7.24 (1H,s ), 7.16 (1H, s), 7.08 (2H, d, J 8.5 Hz), 6.72 (2H, d, J 8.5 Hz) and 5.14 (2H, s).

INTERMEDIATE 47 t-Butyl-3-(4-fluoroohenyl)-3-{2-[4-(1-H-imidazol-1-ylmethyl)phenoxy]-4-pyrimidinyl}propanoate The title compound (0.8 g, 54%) was prepared from Intermediate 46 (545 mg, 3.13 mmol) and Intermediate 11 (1.05 g, 3.13 mmol) in a similar manner to Intermediate 13. $^1$H NMR (CDCl3) δ 8.38 (1H, d, J 5.1 Hz), 7.60 (1H, s), 7.25–7.14 (6H, m), 7.12 (1H, s), 6.99 (3H, m), 6.88 (1H, d, J 5.1 Hz), 5.18 (2H, s), 4.48 (1H, t, J 7.0 Hz), 3.24 (1H, dd, J 16.6, 8.5 Hz), 2.80 (1H, dd, J 16.5, 7.0 Hz) and 1.34 (9H, s).

INTERMEDIATE 48 t-Butyl-3-(2-{4-[(4,5-dihydro-1H-imidazol-2-ylamino)methyl]phenoxy}-4-pyrimidinyl)-3-(4-fluorophenyl)proganoate Intermediate 41 (350 mg, 0.83 mmol), 2-thiomethylimidazolinium iodide (187 mg, 0.8 mmol) and diisopropylethylamine (92 mg, 0.8 mmol) were dissolved in dioxane (5 ml) and heated under reflux 1 h. The solvent was removed in vacuo and the residue partitioned between saturated sodium hydrogen carbonate solution and dichloromethane, the organic phase was separated, dried over magnesium sulphate and concentrated yielding the title compound (275 mg). $^1$H NMR (CDCl$_3$) δ 8.34 (1H, d, J 5.2 Hz), 7.42 (2H, d, J 8.7 Hz), 7.23 (2H, dd, J 7.8, 6.9 Hz), 7.19 (2H, d, J 8.7 Hz), 7.00 (2H, t, 1 7.8 Hz), 6.95 (1H, d, J 5.2 Hz), 4.51 (2H, s), 4.44 (1H, t, 1 6.4 Hz), 3.63 (4H, br s), 3.21 (1H, dd, J 16.5, 7.8 Hz), 2.80 (1H, dd, J 16.5, 7.0 Hz) and 1.33 (9H, s).

INTERMEDIATE 49

1-(4-Benzyloxybenzyl)-1,2,4-trizine

Intermediate 43 (1.0 g, 4.7 mmol) in dichloromethane (10 ml) was treated with thionyl chloride (750 mg, 6.3 mmol) and stirred for 30 min. The solvent was removed in vacuo. 1,2,4-Triazole (810 mg, 11.7 mmol) was added to sodium hydride (60% dispersion in mineral oil, 470 mg, 11.7 mmol) in DMF and stirred at room temperature for 15 min. Intermediate 44 was added and the reaction stirred for 1 h before the solvent was removed in vacuo and the residue partitioned between saturated sodium hydrogen carbonate and dichloromethane. The organic phase was separated, dried over magnesium sulphate and concentrated in vacuo. Chromatography (98% dichloromethane, 2% methanol-silica) yielded the title compound (1.3 g). $^1$H NMR (CDCl$_3$) δ 8.01 (1H, s), 7.98 (1H, s), 7.46–7.30 (5H, m), 7.25 (2H, d, J 8.5 Hz), 6.99 (2H, d, J 8.5 Hz), 5.28 (2H, s) and 5.09 (2H, s).

INTERMEDIATE 50

4-Hydroxybenzyl-1,2,4-triazole

Intermediate 49 (1.3 g, 5.4 mmol) in ethanol (20 ml) was hydrogenated at atmospheric pressure over 10% palladium on carbon (100 mg) for 6 h. The catalyst was removed by filtration and the filtrate concentrated in vacuo yielding the title compound (650 mg). ¹H NMR (CDCl₃) δ 8.82 (1H, s), 7.82 (1H, s), 7.62 (1H, s), 6.87 (2H, d, J 8.5 Hz), 6.58 (2H, d, J 8.5 Hz) and 4.99 (2H, s).

INTERMEDIATE 51 t-Butyl-3-(4-fluoronhenyl)-3-{2-[4-(1H-1,2,4-triazol-1-ylmethyl)phenoxy]-4-pynrmidinyl}propanoate The title compound (1.15 g, 69%) was prepared from Intermediate 50 (0.639, 3.6 mmol) and Intermediate 11 (1.21 g, 3.6 mmol) in a similar manner to Intermediate 13. ¹H NMR (CDCl₃) δ 8.38 (1H. d, J 5.1 Hz), 8.10 (1H, s), 7.99 (1H, s), 7.33 (2H, d, J 8.5 Hz), 7.28–7.19 (4H, m), 6.99 (2H, t, J 8.5 Hz), 6.78 (1H, d, J 5.1 Hz), 5.49 (2H, s), 4.44 (1H, t, J 6.5 Hz), 3.23 (1H, dd, J 16.5, 8.5 Hz), 2.79 (1H, dd, J 16.5, 7.0 Hz) and 1.32 (9H, s).

INTERMEDIATE 52

4-Benzyloxybenzyl-1,3-benzyimidazole

The title compound (1.1 g. 75%) was prepared from Intermediate 43 (1.0 g, 4.7 mmol) and benzimidazole (1.4 g, 11.9 mmol) in a similar manner to Intermediate 49. ¹H NMR (CDCl₃) δ 7.93 (1H, s), 7.82 (1H, m), 7.44–7.22 (8H, m), 7.16 (2H, d, J 8.5 Hz), 6.94 (2H, d, J 8.5 Hz), 5.31 (2H, s) and 5.04 (2H, s).

INTERMEDIATE 53

4-Hydroxybenzyl-1,3-benzimidazole

The title compound (0.56 g, 71%) was prepared from Intermediate 52 (1.1 g, 3.5 mmol) in a similar manner to Intermediate 50. ¹H NMR (CDCl₃) δ 8.76 (1H, s), 7.62 (1H, s), 7.34 (1H, m), 6.99 (1H, m), 6.85 (1H, m), 6.73 (2H, d, J 8.5 Hz), 6.41 (2H, d, J 8.5 Hz) and 4.96 (2H, s).

INTERMEDIATE 54 t-Butyl-3-{2-[4-(1H-1,3-benzimidazol-1-ylmethyl)phenoxy]-4-pyrimidinyl}-3-(4-fluoronhenyl)propanoate The title compound (0.95 g, 73%) was prepared from Intermediate 53 (0.55 g, 2.50 mmol) and Intermediate 11 (0.84 g, 2.50 mmol) in a similar manner to Intermediate 13. ¹H NMR (CDCl₃) δ 8.38 (1H, d, J 5.1 Hz), 8.01 (1H, s), 7.98 (1H, d, J 7.8 Hz), 7.36–7.12 (9H, m), 6.95 (2H, t, J 8.5 Hz), 6.89 (1H, d, J 5.1 Hz), 5.42 (2H, s), 4.44 (1H, t, J 7.5 Hz), 3.22 (1H, dd, J 16.6, 8.5 Hz), 2.79 (1H, dd, J 16.6, 7.0 Hz) and 1.32 (9H, s).

INTERMEDIATE 55

1-(4-Benzyloxybenzyl)-2-nitroimidazole

The title compound (1.3 g, 100%) was prepared from Intermediate 43 (0.86 g, 4.0 mmol) and 2-nitroimidazole (0.5 g, 4.4 mmol) in a similar manner to Intermediate 49. ¹H NMR (CDCl₃) δ 7.42–7.32 (5H, m), 7.18 (3H, m), 7.01 (3H, m), 5.54 (2H, s) and 5.09 (2H, s).

INTERMEDIATE 56

2-Amino-1-(4-hydroxybenzyl)imidazole

The title compound (0.6 g, 78%) was prepared from Intermediate 55 (1.25 g, 4.06 mmol) in a similar manner to Intermediate 50. ¹H NMR (d⁶ DMSO) δ 7.70 (1H, s), 6.95 (2H, d, J 8.5 Hz), 6.69 (2H, d, J 8.5 Hz), 6.40 (2H, d, J 12.0 Hz), 4.74 (2H, s) and 4.57 (2H, br s).

INTERMEDIATE 57 t-Butyl-3-{2-[4-(2-amino-1H-imidazol-1-yimethyl)phenoxa]-4-pyrimidinyl}-3-(4-fluorophenyl)propanoate The title compound (1.1 g, 74%) was prepared from Intermediate 56 (0.57 g, 3.02 mmol) and Intermediate 11 (1.02 g, 3.03 mmol) in a similar manner to Intermediate 13. ¹H NMR (CDCl₃) δ 8.33 (1H, d, J 5.1 Hz), 7.28–7.13 (6H, m), 6.89 (1H, d, J 5.1 Hz), 6.71 (1H, s), 6.69 (2H, t, J 8.5 Hz), 6.62 (1H, s), 4.98 (2H, s), 4.46 (1H, t, J 8.5 Hz), 3.22 (1H, dd, J 16.5, 8.5 Hz), 2.78 (1H, dd, J 16.5, 7.8 Hz) and 1.33 (9H, s).

INTERMEDIATE 58

2-Chloro-4-(3-trifluoromethoxylhenylmethyl)pyrimidine

The title compound (1.25 g, 75%) was prepared from 3-trifluoromethoxybenzylbromide (1.48 g, 5.8 mmol) and 2,4-dichloropyrimidine (0.85 g, 5.8 mmol) in a similar manner to Intermediate 2. ¹H NMR (CDCl₃) δ 8.52 (1H, d, J 5.0 Hz), 7.38 (1H, t, J 7.0 Hz), 7.21–7.10 (3H, m), 7.03 (1H, d, J 5.0 Hz) and 4.12 (2H, s).

INTERMEDIATE 59

Methyl-3-(2-chloro-pyrimidin-4-yl)-3-(3-trofluoromethoxyphenyl) propanoate

The title compound (1.44 g, 94%) was prepared from Intermediate 60 (1.23 g, 4.26 mmol) in a similar manner to Intermediate 3. ¹H NMR (CDCl₃) δ 8.50 (1H, d, J 5.0 Hz), 7.37 (1H, t, J 8.5 Hz), 7.28–7.21 (1H, m), 7.20–7.08 (3H, m), 4.59 (1H, dd, J 7.8, 7.0 Hz), 3.67 (3H, s), 3.49 (1H, dd, J 16.5, 8.5 Hz) and 2.96 (1H, dd, J 16.5, 6.9 Hz).

INTERMEDIATE 60

Methyl-3-(2-{4-[(2-pyridimnylamino)methyl]phenoxy}-4-pyrimmdinyl)-3-(3-trifluoromethoxyphenyl)propanoate The title compound (1.35 g, 64%) was prepared from Intermediate 59 (1.44 g, 4.0 mmol) and Intermediate 1 (0.809) 4.0 mmol) in a similar manner to Intermediate 13. ¹H NMR (CDCl₃) δ 8.39 (1H, d, J 5.0 Hz), 8.12 (1H, d, J 6.5 Hz), 7.48–7.05 (9H, m), 6.89 (1H, d, 1 5.0 Hz), 6.61 (1H, t, J 6.5 Hz), 6.43 (1H, d, J 8.5 Hz), 4.88 (1H, br s), 4.60–4.47 (3H, m), 3.59 (3H,s), 3.37 (1H, dd, J 16.5, 8.5 Hz) and 2.86 (1H, dd, 1 16.5, 6.5 Hz).

INTERMEDIATE 61

2-Chloro-4-(3-cyanophenylmethyl)gyrimidine

The title compound (1.7 g, 73%) was prepared from 3-bromomethylbenzonitrile (2.0 g, 10.2 mmol) in a similar manner to Intermediate 2. ¹H NMR (CDCl₃) δ 8.54 (1H. d, J 5.2 Hz), 7.62–7.42 (4H, m), 7.08 (1H, d, J 5.2 Hz) and 4.14 (2H, s).

INTERMEDIATE 62

Methyl-3-(2-chloro-4-pyrimidinyl)-3-(3-cyanophenyl)propanoate

The title compound (1.44 g, 66%) was prepared from Intermediate 61 (1.67 g, 7.28 mmmol) in a similar manner to Intermediate 3. ¹H NMR (CDCl₃) δ 8.51 (1H, d, J 5.2 Hz), 7.53–7.52 (3H, m), 7.47 (1H, t, J 7.0 Hz), 7.12 (1H, d, J 5.2 Hz), 4.61 (1H, dd, J 7.8, 7.0 Hz), 3.66 (3H, s), 3.47 (1H, dd, J 16.5, 7.8 Hz) and 2.97 (1H, dd, J 16.5, 6.5 Hz).

INTERMEDIATE 63

Methyl-3-(3-cyanophenyl)-3-(2-{4-[(2-gyrodinylamino)methyl]phenoxy}-4-pyrimidinyl) propanoate The title compound (1.53, 49%) was prepared from Intermediate 62 (2.02 g, 6.7 mmol) and Intermediate 1 (1.30 g, 6.7 mmol) in a similar manner to Intermediate 13. ¹H NMR (CDCl₃) δ 8.43 (1H, d, J 5.2 Hz), 8.11 (1H, d, J 5.0 Hz), 7.59–7.50 (3H, m), 7.49–7.35 (4H, m), 7.16 (2H, d, J 8.5 Hz), 6.92 (1H, d, J 5.2 Hz), 6.59 (1H, dd, J 7.8, 7.0 Hz), 6.46 (1H, d, J 8.5 Hz), 4.97 (1H, br s), 4.61 (2H, d, J 7.0 Hz), 4.51 (1H, t, J 7.8 Hz), 3.51 (3H, s), 3.31 (1H, dd, J 16.5, 8.0 Hz) and 2.89 (1H, dd, J 16.5, 7.0 Hz).

INTERMEDIATE 64

2-Chloro-4-(3-methoxyohenylmethyl)pyrmidine

The title compound (1.95 g, 84%) was prepared from 3-methoxybenzylbromide (2.00 g, 9.5 mmol) in a similar manner to Intermediate 2. ¹H NMR (CDCl₃) δ 8.48 (1H, d, J 5.2 Hz), 7.26 (1H, t, J 7.0 Hz), 7.04 (1H, d, J 5.2 Hz), 6.38–6.29 (3H, m), 4.19 (2H, s) and 3.81 (3H, s).

INTERMEDIATE 65

Methyl-3-(2-chloro-4-pyrimidinyl-3-(3-methoxyphenyl)propanoate

The title compound (2.43 g. 95%) was prepared from Intermediate 64 (1.95 g, 8.32 mmol) in a similar manner to Intermediate 3. ¹H NMR (CDCl₃) δ 8.42 (1H, d, j 5.2 Hz), 7.24 (1H, t, J 7.5 Hz), 7.09 (1H, d, J 5.2 Hz), 6.88–6.78 (3H, m), 4.54 (1H, dd, J 8.0, 6.5 Hz), 3.81 (3H, s), 3.64 (3H, s), 3.49 (1H, dd, 16.5, 8.5 Hz) and 2.91 (1H, dd, 16.5, 7.0 Hz).

INTERMEDIATE 66

Methyl-3-(3-methoxyphenyl)-3-(2-{4-[(2-pyridinylamino)methyl]iphenoxy}-4-pyrimidinyl) propanoate The title compound (2.95 g, 80%) was prepared from Intermediate 65 (2.43 g, 7.93 mmol) and Intermediate 1 (1.59 g, 7.93 mmol) in a similar manner to Intermediate 13. ¹H NMR (CDCl₃) δ 8.36 (1H, d, J 5.2 Hz), 8.12 (1H, dd, J 4.6, 1.1 Hz), 7.47–7.39 (3H, m), 7.23–7.12 (3H, m), 6.87 (1H, d, J 5.2 Hz), 6.86–6.78 (4H, m), 6.61 (1H, dd, J 6.9, 6.1 Hz), 6.42 (1H, d, J 8.5 Hz), 4.88 (1H, br s), 4.57 (2H, d, J 7.0 Hz), 4.49 (1H, dd, J 7.8, 7.0 Hz), 3.79 (3H, s), 3.59 (3H, s), 3.39 (1H, dd, J 16.5, 8.5 Hz) and 2.86 (1H, dd, J 16.5, 6.5 Hz).

INTERMEDIATE 67

2-Chloro-4-(4-trifluoromethoxyphenylmethyl) pyrimidine

The title compound (1.9 g, 84%) was prepared from 4-trifluoromethoxybenzylbromide (2.0 g, 7.84 mmol) in a similar manner to Intermediate 2. ¹H NMR (CDCl₃) δ 8.48 (1H, d, J 5.2 Hz), 7.29 (2H, d, J 8.5 Hz), 7.18 (2H, d, J 8.5 Hz), 7.02 (1H, d, J 5.2 Hz) and 4.11 (2H, s).

INTERMEDIATE 68

Methyl-3-(2-chloro-4-pyrimidinyl)-3-(4-trifluoromethoxyphenyl) propanoate

The title compound (2.23 g, 95%) was prepared from Intermediate 67 (1.88 g, 6.52 mmol) in a similar manner to Intermediate 3. ¹H NMR (CDCl₃) δ 8.48 (1H, d, 15.2 Hz), 7.34 (2H, d, J 8.5 Hz), 7.17 (2H, d, J 8.5 Hz), 7.09 (1H, d, J 5.2 Hz), 4.59 (1H, dd, J 7.0, 6.0 Hz), 3.67 (3H, s), 3.48 (1H, dd, J 16.5, 8.5 Hz) and 2.94 (1H, dd, J 16.5, 6.5 Hz).

INTERMEDIATE 69

Methyl-3-(2-{4-[(2-pyridinylamino)methyl] phenoxy}-4-pyrimidinyl)-3-(4-trifluoromethoxyphenyl)propanoate The title compound (2.25 g, 69%) was prepared from Intermediate 68 (2.23 g, 6.2 mmol) and Intermediate 1 (1.2 g, 6.2 mmol) in a similar manner to Intermediate 13. ¹H NMR (CDCl₃) δ 8.41 (1H. d, J 5.2 Hz), 8.13 (1H, d, 5.3 Hz), 7.47–7.39 (3H, m), 7.32, 7.24 (2H, m), 7.20–7.09 (4H, m), 6.88 (1H, d, J 5.2 Hz), 6.61 (1H, dd, J 7.8, 7.0 Hz), 6.43 (1H, d, J 8.5 Hz), 4.89 (1H, br s), 4.59–4.48 (3H, m), 3.61 (3H, s), 3.36 (1H, dd, J 16.5, 8.5 Hz) and 2.88 (1H, dd, J 16.5, 6.5 Hz).

INTERMEDIATE 70

4-(4-Biophenyl-4-ylmethyl)-2-chloropyrimidine

The title compound (1.2 g, 89%) was prepared from 4-phenylbenzylchloride (1.0 g, 4.93 mmol) in a similar manner to Intermediate 2. ¹H NMR (CDCl₃) δ 8.50 (1H, d, J 5.2 Hz), 7.64–7.54 (4H, m), 7.48–7.40 (2H, m), 7.39–7.29 (3H, m), 7.07 (1H, d, J 5.2 Hz) and 4.18 (2H, s).

INTERMEDIATE 71

Methyl-[3-{4-biphenyl}-3-(2-chloro-4-pyrimidianyl)]propanoate

The title compound (1.43 g, 97%) was prepared from Intermediate 70 (1.179, 4.17 mmol) in a similar manner to Intermediate 3. ¹H NMR (CDCl₃) δ 8.48 (1H, d, J 5.2 Hz), 7.59–7.54 (4H, m), 7.48–7.39 (2H, m), 7.39–7.31 (3H, m), 7.13 (1H, d, J 5.2 Hz), 4.62 (1H, dd, J 7.8, 6.9 Hz), 3.68 (3H, s), 3.53 (1H, dd, J 16.5, 8.5 Hz) and 2.98 (1H, dd, J 16.5, 6.5 Hz).

INTERMEDIATE 72

Methyl-3-(4-biphenyl)-3-{2-[4-({2-pyridylamino}methyl)phenoxy]-4-pyrimidinyl}propanoate The title compound (1.50 g, 67%) was prepared from Intermediate 71 (1.43 g, 4.2 mmol) and Intermediate 1 (0.84 mg, 4.2 mmol) in a similar manner to Intermediate 13. ¹H NMR (CDCl₃) δ 8.38 (1H, d, J 5.2 Hz), 8.14 (1H, d, J 6.5 Hz), 7.59–7.51 (4H, m), 7.48–7.39 (5H, m), 7.39–7.31 (3H, m), 7.20 (2H, d, J 8.5 Hz), 6.93 (1H, d, J 5.2 Hz), 6.62 (1H, dd, J 6.9, 6.1 Hz), 6.42 (1H, d, J 8.5 Hz), 4.88 (1H, br s), 4.59 (3H, m), 3.62 (3H, s), 3.45 (1H, dd, J 16.5, 8.5 Hz) and 2.92 (1H, dd, J 16.5, 6.5 Hz).

INTERMEDIATE 73

2-Chloro-4-[(4-trifluoromethylphenyl)methyl] pyrimidine

The title comiound (2.23 g, 74%) was prepared from 4-trifluoromethylbenzylbromide (2.5 g, 10.5 mmol) in a similar manner to Intermediate 2. $^1$H NMR (d$^6$ DMSO) δ 8.69 (1H, d, J 5.2 Hz), 7.68 (2H, d, J 8.5 Hz), 7.52 (2H, d, J 8.5 Hz), 7.49 (1H, d, J 5.2 Hz) and 4.23 (2H, s).

INTERMEDIATE 74

Methyl-3-(2-chloro-4-pyrimidinyl)-3-(4-trifluoromethylphenyl) propanoate

The title compound (1.5 g, 53%) was preparped from Intermediate 73 (2.23 g, 8.2 mmol )in a similar manner to Intermediate 3. (d$^6$ DMSO) δ 8.68 (1H, d, J 5.2 Hz), 7.69 (2H, d, J 7.8 Hz), 7.61–7.56 (3H, m), 4.75 (1H, d, J 7.8 Hz), 3.53 (3H, s), 3.41 (1H, dd, J 16.5, 8.7 Hz) and 3.10 (1H, dd, J 17.4, 6.9 Hz).

INTERMEDIATE 75

Methyl-3-(2-{4-[(2-pyridinylamino)methyl]phenoxy}-4-pyrimidinyl)-3-(4-trifluoromethylphenyl)propanoate The title compound (1.60, 70%) was prepared from Intermediate 74 (1.5 g, 4.51 mmol) and Intermediate 1 (0.90 g, 4.51 mmol) in a similar manner to Intermediate 13. $^1$H NMR (d$^6$ DMSO) δ 8.44 (1H, d, J 6.5 Hz), 7.97 (1H, m), 7.64 (2H, d, J 8.7 Hz), 7.54 (2H, d, J 8.7 Hz), 7.40–7.32 (3H, m), 7.26 (1H, d, J 6.5 Hz), 7.11 (2H, d, J 8.7 Hz), 7.01 (1H, d, J 5.2 Hz), 6.51 (1H, d, J 8.7 Hz), 6.46 (1H, dd, J 6.1, 5.2 Hz), 4.67 (1H, t, J 7.0 Hz), 4.51 (2H, d, J 7.0 Hz), 3.51 (3H, s), 3.30 (1H, dd, J 16.5, 7.0 Hz) and 2.98 (1H, d, J 16.5, 7.0 Hz).

INTERMEDIATE 76

4-Benzyloxybenzonitrile

To a stirred solution of 4-cyanophenol (50 g, 0.42 mol) and potassium carbonate (150 g, 1.1 mol) in DMF (800 ml) was added benzyl bromide (75 ml, 0.63 mol). The reaction mixture was stirred for 2 h at room temperature before filtering off solid and reducing the filtrate in vacuo to give an oil. The solid precipitate was dissolved in water and the pH adjusted to 0.5 using 6.0M hydrochloric acid and extacted into ethyl acetate. The solvent was dried over magnesium sulphate and removed by evaporation in vacuo to give an oil. The two oil products were combined and triturated with diethyl ether/hexane to give a white solid, which was washed with hexane and dried to give the title compound (81 g, 93%). $^1$H NMR (CDCl$_3$) δ 7.5 (2H, d, 1 8.6 Hz), 7.45–7.30 (5H, br m), 7.0 (2H, d, J 8.6 Hz) and 5.14 (2H, s). MS (ES) m/e 210 [M+H]$^+$.

INTERMEDIATE 77

4-Benzyloxybenzylamine

To a stirred suspension of lithium alminium hydride (1.75 g, 0.46 mol) in THF (800 ml) at 0° was added 4-benzyloxybenzonitrile (43.0 g, 0.23 mol) in THF (600 ml), dropwise over 4 h. The reaction mixture was allowed to warm to room temperature and stirred for 16 h and then cooled to 0°. Water (30 ml) was added and 2M sodium hydroxide solution (80 ml) was then added dropwise with stirring. The resulting precipitate was filtered off washed with diethyl ether (100 ml) and toluene (200 ml). The fltrate was washed with sodium chloride solution, dried over sodium sulphate and the solvent removed by evaporation in vacuo, to give a waxy solid. The two soilds were combined to give the title compound (48.26 g, 110%). $^1$H NMR (CDCl$_3$) δ 7.46–7.25 (5H, br m), 7.23 (2H, d, J 8.75 Hz), 6.95 (2H, d, J 8.7 Hz), 5.07 (2H, s), 3.81 (2H, s) and 1.50 (2H, br s). MS (ES) m/e 197 [M+NH$_4$]$^+$.

INTERMEDIATE 78

1-(2-Aminophenyl)-3-(4-benzyloxybenzyl)-2-thiourea

To a stirred solution of 1,1'-thiocarbonyidiimidazole (12.5 g, 70 mmol) and imidazole (0.95 g, 140 mmol) in acetonitrile (250 ml) at 0° was added Intermediate 77 (11.46 g, 53.8 mmol) in acetonitrile (150 ml) dropwise. The reaction mixture was allowed to warm to room temperature and stirred for 2.5 h and then 1,2-phenylene diamine (10.2 g, 90 mmol) was added. The reaction mixture was stirred overnight. The cream precipitate was filtered off and dried to give the title compound (14.8 g, 88%). $^1$H NMR (d$^6$ DMSO) δ 8.87 (1H, s), 7.63 (1H, br s), 7.45–7.28 (5H, b m), 7.25 (2H, d J 8.7 Hz), 7.00–6.93 (4H, m), 6.74 (1H, dd, J 8.3, 1.3 Hz), 6.56 (1H, td, J 7.5, 1.4 Hz), 5.08 (2H, s), 4.62 (2H, d, J 5.4 Hz) and 3.32 (2H, s). MS (ES) m/e 364 [M+H]$^+$.

INTERMEDIATE 79

2-(4-{Benzyloxybenzyl}amino)benzimidazole

A stirring solution of Intermediate 78 (3.63 g, 0.01 mol), mercuric oxide (4.33 g, 0.02 mol) and sulphur (64 mg, 0.03 mol) in ethanol (100 ml) was heated under reflux for 48 h. Upon cooling the reaction mixture was filtered through Celite® and the filtrate solvent removed by evaporation in vacuo. The crude product was purified by flash column chromatography (ethyl acetate→90% ethyl acetate, 10% methanol-silica) giving the title compound as white solid (1.5 g, 46%). $^1$H NMR δ 10.72 (1H, br s), 7.44–7.39 (5H, br m), 7.29 (2H, d, J 8.6 Hz), 7.11 (1H, v br s), 7.10 (1H, d, J 8.9 Hz), 6.95 (2H, d, J 8.7 Hz), 6.99–6.90 (1H, br m), 6.84 (2H, dd, J 5.9, 3.7 Hz), 5.07 (2H, s) and 4.42 (2H, d, J 5.9 Hz). MS (ES) m/e 330 [M+H]$^+$.

INTERMEDIATE 80

2-(4-{Hydroxybenzyl}amino)benzimidazole

The title comDound (7.3 g, 100%) was prepared from Intermediate 79 (10.07 g, 0.03 mol) in a similar manner to Intermediate 50. $^1$H NMR (d$^6$ DMSO) δ 10.68 (1H, br s), 9.24 (1H, br s), 7.19–7.10 (5H, m), 6.90–6.81 (4H, m), 6.70 (2H, d, J 8.5 Hz) and 4.37 (2H, d, J 5.6 Hz). MS (ES) m/e 240 [M+H]$^+$.

INTERMEDIATE 81

Ethyl-3-[2-(4-cyanoanilino)-4-pyrimidinyl]propanoate

Intermediate 12 (5.0 g, 23.3 mmol) and 4-aminobenzonitrile (2.76 g, 23.3 mmol) in ethanol (25 ml) were heated under refux for 6 h. The ethanol was then removed in vacuo and the resulting solid triturated with diethyl ether, filtered and dried to give the title compound (6.5 g, 94%). $^1$H NMR (CDCl$_3$) δ 8.35 (1H, d, J 5.1 Hz), 7.77 (2H, d, J 8.8 Hz), 7.60 (2H, d, J 8.8 Hz), 6.76 (1H, d, J 5.1 Hz), 4.13 (2H, q, J 7.1 Hz), 3.04 (2H, t, J 7.1 Hz), 2.83 (2H, t, J 7.1 Hz) and 1.24 (3H, t, J 7.1 Hz). MS (ES) m/e 297 [M+H]$^+$.

INTERMEDIATE 82

Ethyl-3-[2-(4-aminomethylanilino-4-pyrimidinyl]propanoate

The title compound (700 mg, 69%) was prepared from Intermediate 81 (1.0 g, 3.38 mmol) in a similar manner to Intrmediate 21. ¹H NMR (CDCl₃) δ 8.09 (1H, d, J 5.1 Hz), 7.47 (2H, d, J 8.4 Hz), 7.12 (2H, d, J 8.4 Hz), 6.48 (1H, d, J 5/1 Hz), 4.05–3.90 (5H, m), 2.83 (2H, t, J 7.1 Hz), 2.66 (2H, t, J 7.1 Hz) and 1.07 (3H, t, J 7.1 Hz). MS (ES) m/e 301 [M+H]⁺.

INTERMEDIATE 83

Ethyl-3-[2-{4-[2-pyridinylamino]methyl)anilino}-4-pyrimidinyl]propanoate

The title compound (400 mg, 46%) was prepared from Intermediate 82 (700 mg, 2.33 mmol) in a similar manner to Intermediate 30. ¹H NMR (CDCl₃) δ 8.27 (1H,d, J 5.0 Hz), 8.11 (1H, dd, J 5.0, 1.0 Hz), 7.59 (2H, d, J 8.5 Hz), 7.40 (1H, dt, J 7.0, 1.9 Hz), 7.32 (2H, d, J 8.4 Hz), 7.12 (1H, s), 6.62 (1H, d, 15.0 Hz), 6.59–6.56 (1H, m), 4.90–4.80 (1H, m), 4.46 (2H, d, J 5.7 Hz), 4.13 (2H, q, J 7.1 Hz), 2.9 (2H, t, J 7.1 Hz), 2.81 (2H, t, J 7.1 Hz) and 1.23 (3H, t, J 7.1 Hz). MS (ES) m/e 378 [M+H]⁺.

INTERMEDIATE 84

Benzyl-4-bromophenylether

The title compound (6.22 g, 82%) was prepared from 4-bromophenol (5.0 g, 28.9 mmol), benzyl bromide (3.44 ml, 28.9 mmol) and cesium carbonate (10.36 g, 31.8 mmol) in a similar manner to Intermediate 76. ¹H NMR (CDCl₃) δ 7.50–7.30 (7H, m), 6.86 (2H, d, J 8.8 Hz) and 5.05 (2H, s).

INTERMEDIATE 85

Benzyl-4-(6-chloropyridyin-2-yl)phenyl ether

To a solution of Intermediate 84 (2.0 g, 7.60 mmol) in THF (20 ml) at −78° was added n-butyl lithium (1.6M solution in hexanes, 3.34 ml, 8.37 mmol). The reaction mixture was stirred for 0.5 h and zinc chloride (1.14 g, 8.37 mmol) was added. After a further hour the reaction mixture was warmed to ambient temperature. The reaction was treated with 2,6-dichloropyridine (1.35 g, 9.13 mmol) and tetrakis(triphenylphosphine) palladium (0) (266 mg, 0.23 mmol). The reaction was heated under reflux for 18 h, then quenched with water, extracted into dichloromethane, dried over sodium sulphate and concentrated in vacuo. Recrystallisation from hexane/dichloromethane gave the title compound as a cream powder (2.3 g, 100%). ¹H NMR (CDCl₃) δ 7.96 (2H, d, J 8.9 Hz), 7.66 (1H, t, J 7.7 Hz), 7.57 (1H, d, J 7.7 Hz), 7.57–7.33 (5H, m), 7.19 (1H, d, J 7.7 Hz), 7.06 (2H, d, J 8.9 Hz) and 5.13 (2H, s).

INTERMEDIATE 86

Benzyl-4-[6-(4-methoxybenzylamino)pyridin-2-yl]phenyl ether

The title compound (0.74 g, 33%) was prepared from Intermediate 85 (1.6 g, 5.65 mmol) and 4-methoxybenzylamine (1.1 ml, 8.47 mmol) in a similar manner to Intermediate 38. ¹H NMR (CDCl₃) δ 7.98 (2H, d J 8.7 Hz), 7.49–7.37 (6H, m), 7.34 (2H,d, J 8.6 Hz), 7.06 (2H, d, J 8.7 Hz), 7.02 (1H, d, J 7.6 Hz), 6.90 (2H, d, J 8.6 Hz), 6.29 (1H d, J 8.2 Hz), 5.13 (2H, s), 4.96 (1H, t, J 5.3 Hz), 4.52 (2H, d, J 5.6 Hz) and 3.81 (3H, s). MS (ES) m/e 397 [M+H]⁺.

INTERMEDIATE 87

4-[6-(4-Methoxybenzylamino)-pyridin-2-yl] phenol

The title compound (500 mg, 87%) was prepared from Intermediate 86 (740 mg, 1.87 mmol) in a similar manner to Intermediate 50. ¹H NMR (CDCl₃) δ 7.73 (2H, d, J 8.6 Hz), 7.45 (1H, t, J 7.9 Hz), 7.26 (2H, d, J 8.6 Hz), 6.93 (1H, d, J 7.5 Hz), 6.85 (2H, d, J 8.6 Hz), 6.73 (2H, d, J 8.6 Hz), 6.27 (1H, d, J 8.3 Hz), 5.26 (1H, br s), 4.43 (2H, s) and 3.77 (3H, s). MS (ES) m/e 307 [M+H]⁺.

INTERMEDIATE 88 t-Butly-3-[2-{4-(2-(4-methoxybenzylamino)-6-pyridinyl)phenoxy}-4-pyrimidinyl]-3-(4-fluorophenyl)propanoate The title compound (300 mg, 30%) was prepared from Intermediate 87 (500 mg, 1.63 mmol) and Intermediate 11 (658 mg, 1.96 mmol) in DMF in a similar manner to Intermediate 13. ¹H NMR (CDCl₃) 5 8.38 (1H, d, J 5.14 Hz), 8.05 (2H, d, J 8.7 Hz), 7.49 (1H, t, J 7.8 Hz), 7.33 (2H, d, J 8.7 Hz), 7.28–7.22 (4H, m), 7.07 (1H, d, J 7.3 Hz), 6.98 (2H, t, J 8.7 Hz), 6.90–6.87 (3H, m), 6.34 (1H, d, J 8.1 Hz), 4.88 (1H, br s), 4.54 (2H, s), 4.43 (1H, t, J 7.7 Hz), 3.80 (3H, s), 3.25 (1H, dd, J 16.1, 8.6 Hz), 2.78 (1H, dd, J 16.1, 7.1 Hz) and 1.32 (9H, s). MS (ES) m/e 607 [M+H]⁺.

INTERMEDIATE 89

Benzyl-4-(2-oyrimidyl)phenyl ether

Tetrakis(triphenylphosphine)palladium (0) (185 mg, 0.16 mmol) was added to a stirred solution of 2-bromopyrimidine (523 mg, 3.29 mmol) in dioxane (4 ml). After 0.5 h, 4-benzyloxybenzene boronic acid (8.25 mg, 3.62 mmol) in dioxane (2 ml) and 2M sodium carbonate solution(4.1 ml, 8.23 mmol) were added. The reaction mixture was heated to reflux for 24 h, cooled, quenched with water and extracted into dichloromethane. The organics were dried over sodium sulphate and evaporated. Purification of the residue by flash chomatorgaphy (6:1 hexane, ethyl acetate-silica) gave the title compound (760 mg, 88%) ¹H NMR (CDCl₃) δ 8.75 (2H, d, J 4.8 Hz), 8.41 (2H, d, J 8.9 Hz), 7.48–7.32 (5H, m), 7.12 (1H, t, J 4.8 Hz), 7.08 (2H, d J 8.9 Hz), and 5.15 (2H, s). MS (ES) m/e 263 [M+H]⁺.

INTERMEDIATE 90

4-(2-Pyrmidyl)phenol

The title compound (230 mg, 46%) was prepared from Intermediate 89 (760 mg, 2.90 mmol) in a similar manner to Intermediate 50. ¹H NMR (MeOD) δ 8.72 (2H, d, J 4.9 Hz), 8.21 (2H, d, J 8.8 Hz), 7.21 (1H, t, J 4.9 Hz) and 6.86 (2H, d, J 8.9 Hz). MS (ES) m/e 173 [M+H]⁺.

INTERMEDIATE 91 t-Butyl-3-[2-(4-{2-pyrimlidinyl}plhenoxy)-4-pyrimidinyl]-3-(4-fluorophenyl propanoate The title compound (400 mg, 63%) was prepared from Intermediate 90 (230 mg, 1.34 mmol) and Intermediate 11 (472 mg, 1.40 mol) in a similar manner to Intermediate 13. ¹H NMR (CDCl₃) 5 8.76 (2H, d, J 4.8 Hz), 8.51 (2H, d, J 8.7 Hz), 8.36 (1H, d, J 5.0 Hz), 7.27 (2H, d, J 8.7 Hz), 7.22 (2H, dd, J 8.6, 5.4 Hz), 7.14 (1H, t, J 4.8 Hz), 6.94 (2H, t, J 8.6 Hz), 6.87 (1H, d, J 5.0 Hz), 4.11 (1H, dd, J 8.6, 6.9 Hz), 3.22 (1H, dd, J 16.1, 8.6 Hz), 2.75 (1H, dd, J 16.1, 6.9 Hz) and 1.29 (9H, s). MS (ES) m/e 473 [M+H]⁺.

INTERMEDIATE 92

Benzyl-4-(4.5-dichloro-2-imidazole)phenyl ether

The title compound (510 mg, 49%)was prepared from 2-bromo-4,5-dichloroimidazole (710 mg, 3.29 mmol) in a similar manner to Intermediate 89. $^1$H NMR (CDCl$_3$) δ 7.70 (2H, d, J 8.9 Hz), 7.45–7.31 (5H, m), 7.04 (2H, d, J 8.9 Hz) and 5.12 (2H, s). MS (ES) m/e 319 [M+H]$^+$.

INTERMEDIATE 93

4-(2-Imidazole)phenol

The title compound (570 mg, 88%) was prepared from Intermediate 92 (1.0 g, 3.14 mmol) in a similar manner to Intermediate 50. $^1$H NMR (d$^6$ DMSO) δ 9.59 (1H, s), 7.72 (2H, d, J 8.5 Hz), 7.01 (2H, s), 6.79 (2H, d, J 8.5 Hz) and 3.31 (1H, s). MS (ES) m/e 161 [MH+]$^+$.

INTERMEDIATE 94 t-Butyl-3-(2-{4-(2-imidazole)phenoxy}-4-pyrimidinyl)-3-(4-fluorophenyl)proganoate The title compound (860 mg, 91%) was prepared from Intermediate 93 (330 mg, 2.06 mmol) and Intermediate 11 (764 mg, 2.27 mmol) in a similar manner to Intermediate 13. $^1$H NMR (CDCl$_3$) δ 8.28 (1H, d, J 5.0 Hz), 7.97 (2H, d, J 8.6 Hz), 7.18–7.08 (6H, m), 6.87 (2H, t, J 8.6 Hz), 6.80 (1H, d, J 5.0 Hz), 4.35 (1H, dd, J 8.5, 7.1 Hz), 3.13 (1H, dd J 16.1, 8.5 Hz), 2.70 (1H, dd, J 16.1, 7.1 Hz) and 1.22 (9H, s). MS (ES) m/e 461 [M+H]$^+$.

INTERMEDIATE 95 t-Butyl-3-[2-({4-(6-{4-methoxybenzyl}amino)-2-pyridinyl}phenoxy)-4-pyrimidinyl]-3-(4-methoxycarbonylphenyl)propanoate The title compound (700 mg, 47%) was prepared from Intermediate 87 (700 mg, 2.20 mmol) and Intermediate 35 (10.4 g, 2.75 mmol) in a similar manner to Intermediate 13. $^1$H NMR (CDCl$_3$) δ 8.40 (1H, d, J 5.3 Hz), 8.09 (2H, d, J 8.6 Hz), 7.98 (2H, d, J 8.7 Hz), 7.80–7.73 (1H, m), 7.55 (1H, t, J 7.9 Hz), 7.41–7.20 (7H, m), 7.03 (1H, d, J 7.3 Hz), 6.90 (2H, d, J 8.7 Hz), 6.38 (1H, d, J 7.9 Hz), 4.49–4.58 (3H, m), 3.90 (3H, s), 3.30 (3H, s), 3.31 (1H, dd, J 16.5, 8.5 Hz), 2.84 (1H, dd, J 16.5, 7.4 Hz) and 1.33 (9H, s). MS (ES) m/e 647 [M+H]$^+$.

INTERMEDIATE 96

Benzyl-3-bromophenyl ether

The title compound (15.2 g, 100%) was prepared from 3-bromophenol (10.0 g, 57.8 mmol) in a similar manner to Intermediate 84. $^1$H NMR (CDCl$_3$) δ 7.43–7.31 (5H, m), 7.15–7.08 (3H, m), 6.90 (1H, d, J 7.7 Hz) and 5.03 (2H, s). MS (ES) m/e 263 [M+H]$^+$.

INTERMEDIATE 97

Benzyl-3-(6-chloro-2-pyridinyl)phenyl ether

The title compound (6.0 g, 88%) was prepared from Intermediate 96 (6.0 g, 22.8 mmol) and 2,6-dichloropyridine (4.05 g, 27.4 mmol) in a similar manner to Intermediate 85. $^1$H NMR (CDCl$_3$) δ 7.70–7.50 (4H, m), 7.45–7.25 (7H, m), 7.10–7.05 (1H, m) and 5.05 (2H, s). MS (ES) m/e 298.5 [M+H]$^+$.

INTERMEDIATE 98

Benzyl-3-(5-{4-methoxybenzyl}amino-2-pyridinyl)phenyl ether

The title comgound (2.0 g, 68%) was prepared from Intermediate 97 (2.2 g, 7.39 mmol) and 4-methoxybenzylamine (1.51 ml, 11.6 mmol) in a similar manner to Intermediate 38. $^1$H NMR (CDCl$_3$) δ 7.98 (2H, d, J 8.7 Hz), 7.49–7.37 (6H, m), 7.33 (2H, d, J 8.6 Hz), 7.06 (2H, d, J 8.7 Hz), 7.02 (1H, d, J 7.6 Hz), 6.90 (2H, d, J 8.6 Hz), 6.30 (1H, d, J 8.2 Hz), 5.13 (2H, s), 4.96 (1H, br t, J 5.3 Hz), 4.52 (2H, d, J 8.6 Hz) and 3.81 (3H, s). MS (ES) m/e 397 [M+H]$^+$.

INTERMEDIATE 99

3-(5-{4-Methoxybenzyl}amino-2-ynrdinyl)phenol

The title compound (280 mg, 55%) was prepared from Intermediate 98 (650 mg, 1.64 mmol) in a similar manner to Intermediate 50. $^1$H NMR (CDCl$_3$) δ 7.45 (1H, s), 7.43 (2H, t, J 7.9 Hz), 7.28–7.21 (3H, m), 6.96 (1H, d, J 7.4 Hz), 6.90–6.78 (3H, m), 6.32 (1H, d, J 8.3 Hz), 4.44 (2H, s) and 3.78 (3H, s). MS (ES) m/e 307 [M+H]$^+$.

INTERMEDIATE 100 t-Butyl-3-[2-(3-{5-(4-methoxybenzyl)amino-2-pyridinyl}phenoxy)-4-pyrimidinyl]-3-(4-fluorophenyl)propanoate The title compound (150 mg, 27%) was prepared from Intermediate 99 (280 mg, 0.92 mmol) and Intermediate 11 (309 mg, 0.92 mmol) in a similar manner to Intermediate 13. $^1$H NMR (CDCl$_3$) δ 8.37 (1H, d, J 5.0 Hz), 7.89 (1H, d, J 7.9 Hz), 7.84 (1H, s), 7.50–7.45 (3H, m). 7.32–7.17 (3H, m), 7.06 (1H, d, J 7.4 Hz), 6.92 (2H, t, J 9.7 Hz), 6.35 (1H, d, J 7.9 Hz), 4.50 (2H, s), 4.42 (1H, dd, J 7.4, 7.1 Hz), 3.79 (3H, s), 3.25 (1H, dd, J 16.1, 7.4 Hz), 2.77 (1H, dd, J 16.1, 7.1 Hz) and 1.30 (9H, s).

INTERMEDIATE 101

Ethyl-3-(2-{4-[(1H-1,3-benzimadzol-2-ylamino)methyl]phenoxy}-4-pyrimidinyl)propanoate The title compound (0.7 g, 39%) was prepared from Intermediate 80 (1.0 g, 4.66 mmol) and Intermediate 12 (1.11 g, 4.66 mmol) in a similar manner to Intermediate 13. $^1$H NMR (CDCl$_3$) δ 8.38 (1H, d, J 5.0 Hz), 7.38 (2H, d, 8.5 Hz), 7.20–7.05 (5H, m), 6.98–6.93 (2H, m), 4.59 (2H, s), 4.10 (2H, q, J 7.1 Hz), 3.06 (2H, t, J 7.2 Hz), 2.78 (2H, t, J 7.2 Hz) and 1.23 (3H, t, J 7.1 Hz).

INTERMEDIATE 102

Ethyl-3-[2-(N-allyl-4-cyanoanioino)-4-pyromidinyl]propanoate

Intermediate 81 (1 g, 3.38 mmol) was dissolved in DMF (10 ml) and sodium hydride (60% dispersion in mineral oil, pre-washed with hexane, 0.14 g, 3.55 mmol) was added followed by allyl bromide (0.59 ml, 6.76 mmol). The reaction mixture was heated to 120° under a nitrogen atmosphere for 24 h and then quenched with saturated sodium hydrogen carbonate solution.

The organics were extracted into dichloromethane, dried over sodium sulphate, filtered and concentrated in vacuo. Purification by flash-chromatography (1.3 ethyl acetate, dichioromethane-silica ) gave the title compound as a yellow oil (0.62 g, 55%). $^1$H NMR (CDCl$_3$) δ 8.23 (1H, d, J 5.0 Hz), 7.60 (2H, d, J 8.7 Hz), 7.47 (2H, d, J 8.8 Hz), 6.62 (1H, d, J 5.0 Hz), 5.15 (2H, d, J 1.3 Hz), 4.69–4.67 (2H, m), 4.10 (2H, q, J 7.1 Hz), 2.95 (2H, t, J 7.0 Hz), 2.72 (2H, t, J 7.0 Hz) and 1.22 (3H, t, J 6.2 Hz).

INTERMEDIATE 103

Ethyl-3-{2-[4-aminomethyl)-N-propylaniino]-4-pyrimidionyl}propanoate

The title compound (0.63 g, 100%) was prepared from Intermediate 102 (0.62 g, 1.85 mmol) in a similar manner to Intermediate 21. $^1$H NMR (d$^6$ DMSO) δ 8.13 (1H, d, 4.9 Hz), 7.47 (2H, d, J 8.2 Hz), 7.29 (2H, d, J 8.0 Hz), 6.61 (1H, d, J 5.0 Hz), 4.06–4.00 (4H, m), 3.89 (2H, t, J 7.3 Hz), 2.82 (2H, t, I 6.7 Hz), 2.66 (2H, t, 6.8 Hz), 1.54 (2H, m), 1.15 (3H, t, J 7.1 Hz) and 0.83 (3H, t, J 7.4 Hz). MS (ES) m/e 343 [M+H]$^+$.

INTERMEDIATE 104

Ethyl-3-(2-{N-propyl-4-[(2-pyridinylamino)methyl]anilino}-4-pyrimidinyl)propanoate The title compound (0.6 g, 77%) was prepared from Intermediate 103 (0.63 g, 1.85 mmol) in a similar manner to Intermediate 30. $^1$H NMR (CDCl$_3$) δ 8.13 (2H, d, J 4.9 Hz), 7.42–7.30 (3H, m), 7.26–7.21 (2H, m), 6.44–6.42 (2H, m), 4.52 (2H, d, J 5.7 Hz), 4.13 (2H, q, J 7.2 Hz), 3.91 (2H, m), 2.92 (2H, t, J 7.1 Hz), 2.74 (2H, t, J 7.0 Hz), 1.71–1.62 (2H, m), 1.25 (3H, t, J 7.1 Hz) and 0.91 (3H, t, J 7.4 Hz). MS (ES) m/e 420 [M+H]$^+$.

INTERMEDIATE 105

1-Trityl-1H-imidazole

Imidazole (10.0 g, 146.9 mmol) was added to sodium hydride (60% dispersion in mineral oil, pre-washed in hexane, 6.5 g, 161.6 mmol) in DMF (200 ml), triphenylmethylchloride (41.0 g, 146.9 mmol) was then added and the reaction mixture stirred at room temperature for 18 h. The mixture was poured onto ice and the solid precipitate formed filtered off and partitioned between water and dichloromethane. The organic phase was washed with brine and dried over sodium sulphate and concentrated in vacuo to give the title compound (37.8 g, 83%). $^1$H NMR (CDCl$_3$) δ 7.42–7.03 (1H, m). MS (ES) m/e 311 [M+H]$^+$.

INTERMEDIATE 106

(1-Trityl-1H-imidazol-2-yl)-(4-{benzyloxy}phenyl)methanol

Intermediate 105 (10.0 g, 32.2 mmol) was dissolved in THF (100 ml) and cooled to −78°. n-Butyl lithium (1.6M solution in hexanes, 22.14 ml, 34.8 mmol) was added followed by 4-benzyloxybenzaldehyde (6.84 g, 32.2 mmol). The reaction mixture was stirred for 3 h and partitioned between water and ethyl acetate. The organic layer was dried over sodium sulphate, filtered and concentrated in vacuo. Purification by flash chromatography (dichloromethane→ethyl acetate-silica) gave the tite compound (9.29 g, 55%). $^1$H NMR (CDCl$_3$) δ 7.41–7.06 (22H, m), 6.85–6.74 (3H, m), 6.67 (2H, d, J 8.8 Hz), 5.02 (2H, s).

INTERMEDIATE 107

Benzyl-4-{(1H-imidazol-2-ylmethyl}phenol

Intermediate 106 (6.53 g, 12.51 mmol) was dissolved in dichloromethane (50 ml) and added to trifluoroacetic acid (50 ml) and triethylsilane (14.3 ml, 86.5 mmol). The reaction mixture was stirred under nitrogen overnight and then concentrated in vacuo. The residue was then partitioned between 1M hydrochloric acid and ether. The aqueous layer was basified with 10% sodium hydroxide and then extracted into dichloromethane and concentrated in vacuo. Purification by flash chromatography (95% dichloromethane, 5% methanol-silica) gave the title compound (0.92 g, 28%). $^1$H NMR (CDCl$_3$) δ 7.42–7.36 (5H, m), 7.17 (2H, d, J 8.6 Hz), 6.95 (4H, d, J 8.6 Hz), 5.06 (2H, s), 4.08 (2H, s). MS (ES) m/e 265 [M+H]$^+$.

INTERMEDIATE 108

4-(1H-Imidazol-2-ylmethyl)phenol

The title compound (0.27 g, 45%) was prepared from Intermediate 107 (0.92 g, 3.48 mmol) in a similar manner to Intermediate 50. $^1$H NMR (d$^6$ DMSO) δ 7.00 (2H, d, J 8.6 Hz), 6.87 (2H, s), 6.67 (2H, d, J 8.6 Hz), 3.82 (2H, s). MS (ES) m/e 175 [M+H]$^+$.

INTERMEDIATE 109

Ethyl-3-(2-{4-[1H-imidazol-2-ylmethyl]phenoxy}-4-pyrimidinyl) propanoate

The title compound (0.25 g, 46%) was prepared from Intermediate 108 (0.27 g, 1.55 mmol) and Intermediate 12 (0.33 g, 1.55 mmol) in a similar manner to Intermediate 13. $^1$H NMR (CDCl$_3$) δ 8.29 (1H, d, J 5.0 Hz), 7.19 (2H, d, J 8.5 Hz), 7.06–7.02 (2H, m), 6.90–6.88 (3H, m), 4.07–4.00 (4H, m), 3.00 (2H, t, J 7.1 Hz), 2.71 (2H, t, J 7.1 Hz), 1.16 (3H, t, J 7.1 Hz).

INTERMEDIATE 110

[4-(Benzyloxy)phenyl]-(1H-imidazol-2-yl)methanol

Intermediate 106 (5.67 g, 10.86 mmol) was dissolved in CH$_3$OH (~50 ml) and concentrated hydrochloric acid (10 ml) was added. The reaction mixture was stirred overnight then basified with saturated sodium hydrogen carbonate solution. The resulting precipitate was collected and triturated with hot toluene to leave the title compound as a white solid (1.59 g, 52%). $^1$H NMR (d$^6$ DMSO) δ 7.43–7.26 (7H, m), 6.93 (2H, d, J 8.7 Hz), 6.86 (2H, s), 6.01 (1H, d, J 4.13 Hz), 5.64 (1H, s), 5.01 (2H, s), MS (ES) m/e 281 [M+H]$^+$.

INTERMEDIATE 111

4-[Hydroxy(1H-imidazol-2-yl)methyl]phenol

The title compound (0.67 g, 100%) was prepared from Intermediate 110 (1.0 g, 3.57 mmol) in a similar manner to Intermediate 50. $^1$H NMR (d$^6$ DMSO) δ 7.15 (2H, d, J 8.5 Hz), 6.89 (2H, s), 6.67 (2H, d, J 8.5 Hz), 5.61 (1H, s).

INTERMEDIATE 112

Ethyl-3-(4-fluorophenyl)-3-(2-{4-hydroxy(1H-imidazol-2-yl)methyl phenoxy}-4-pyrimidinyl)propanoate The title compound (0.75 g, 45%) was prepared from Intermediate 111 (0.69 g, 3.63 mmol) and Intermediate 116 (1.08 g, 3.63 mmol) in a similar manner to Intermediate 13. $^1$H NMR (CDCl$_3$) δ 8.26 (1H, d, J 5.1 Hz), 7.41 (2H, d, J 7.1 Hz), 7.26–7.19 (4H, m), 7.09 (2H, d, J 8.55 Hz), 6.96 (2H, t, J 8.5 Hz), 6.83 (2H, d, J 5.1 Hz), 5.88 (1H, s), 4.48 (1H, d, J 2.1 Hz), 4.10 (2H, q, J 2.9 Hz), 3.32–3.24 (1H, m), 2.85–2.77 (1H, m), 1.12 (3H, t, J 7.1 Hz) MS (ES) m/e 463 [M+H]$^+$.

INTERMEDIATE 113

2-Chloro-4-(3-bromobenzyl)pyrmidine

The title compound (4.8 g, 70%) was prepared from 3-bromobenzyl bromide (6.0 g, 24 mmol) in a similar manner to Intermediate 2. $^1$H NMR (CDCl$_3$) δ 8.50 (1H, d, J 5.1 Hz), 7.41 (2H, m), 7.19 (2H, m), 7.03 (1H, m) and 4.07 (2H, s). MS (ES) m/e 285 [M+H]$^+$.

INTERMEDIATE 114 t-Butyl-3-(2-Chloro-4-pyrimidinyl)-3-(3-bromonhenyl)propanoate

The title compound (5.59, 83%) was prepared from Intermediate 113 (4.84 g, 17.1 mmol) in a similar manner to Intermediate 10. $^1$H NMR (CDCl$_3$) δ 8.45 (1H, d, J 5.1 Hz), 7.40 (2H, m), 7.21 (2H, m), 7.02 (1H, d, J 5.1 Hz), 4.47 (1H, dd, J 9.0, 6.5 Hz), 3.34 (1H, dd, J 16.3, 9.0 Hz), 2.80 (1H, dd, J 16.3, 6.5 Hz), 1.35 (9H, s). MS (ES) m/e 419 [M+Na]$^+$.

INTERMEDIATE 115 t-Butyl-3-(3-bromophenyl)-3-(2-{4-[(2-pyridinylamino)methyl]phenoxy}-4-gvrimidinyl)propanoate The title compound (6.0 g, 76%) was prepared from Intermediate 1 (3.10 g, 15.5 mmol) and Intermediate 114 (5.59 g, 14.1 mmol) in a similar manner to Intermediate 13. $^1$H NMR (CDCl$_3$) δ 8.37 (1H, d, J 5.1 Hz), 8.09 (1H, d, J 5.1 Hz), 7.44 (5H, m), 7.17 (6H, m), 6.86 (1H, d, J 5.1 Hz), 6.61 (1H, m), 6.43 (1H, d, J 8.5 Hz), 4.55 (2H, d, J 5.4 Hz), 4.40 (1H, dd, J 8.6, 6.9 Hz), 3.23 (1H, dd, J 16.1, 8.6 Hz), 2.77 (1H, dd, J 16.1, 8.6 Hz), 1.32 (9H, s). MS (ES) m/e 562.9 [M+H]$^+$.

INTERMEDIATE 116

Ethyl-3-(2-chloro-4-pyrimidinyl)-3-(4-fluorolphenyl)propanoate

The title compound (13.8 g, 94%) was prepared from Intermediate 2 (10.0 g, 44.4 mmol) and ethyl bromoacetate (7.52 g, 45 mmol) in a similar manner to Intermediate 3. $^1$H NMR (CDCl$_3$) δ 8.45 (1H, d, J 5.1 Hz), 7.26 (2H, m), 7.04 (3H, m), 4.55 (1H, dd, J 8.7, 6.5 Hz), 4.07 (2H, m), 3.43 (1H, dd, J 16.6, 8.7 Hz), 2.90 (1H, dd, J 16.6, 6.0 Hz) and 1.18 (3H, t, J 7.2 Hz). MS (ES) m/e 309 [M+H]$^+$.

INTERMEDIATE 117

Methyl-4-benzyloxybenzoate

The title compound (26.6 g, 110%) was prepared from methyl 4-hydroxybenzoate (15.2 g, 125 mmol) utilising sodium hydride as base, in a similar manner to Intermediate 76. $^1$H NMR (CDCl$_3$) δ 8.00 (2H, d, J 8.9 Hz), 7.82–7.73 (5H, br m), 6.99 (2H, d, J 8.9 Hz), 5.12 (2H, s) and 3.89 (3H, s). MS (ES) m/e 243 [M+H]$^+$.

INTERMEDIATE 118

4-Benzyloxybenzoic acid

A solution of Intermediate 117 (26.6 g, 109 mol) in a mixture of dioxane (200 ml), THF (200 ml) and water (250 ml) was treated with lithium hydroxide mono hydrate (6.3 g, 150 mmol) and the reaction mixture stirred for 16 h at 200. The solvents were removed in vacuo and the residue partitioned between water and ether to give a white solid. This was filtered off as crop 1. The filtrate was extracted with ether dried over magnesium sulphate and evaporated in vacuo to give crop 2. The two crops were combined, dissolved in methanol/water and acidified to pH1 with 6M aqueous hydrochloric acid. The white precipitate was filtered off washed well with water and dried under high vacuum to give the title compound as a white solid (20.2 g, 88%). $^1$H NMR (CDCl$_3$) δ 8.06 (2H, d, J 8.8, 2.2 Hz), 7.45–7.36 (5H, m), 7.02 (2H, d, J 8.8, 2.0 Hz) and 5.14 (2H, s).

INTERMEDIATE 119

(2-Trimethylsilyl)ethyl 4-benzyloxybenzoate

To a stirred solution of Intermediate 118 (20.2 g, 90 mmol), DMAP (2.2 g, 20 mmol), and 2-(trimethylsilyl)ethanol (19 ml, 130 mmol), in dichloromethane was added 1,2-dicyclohexylcarboiimide (20.1 g, 100 mmol). The reaction mixture was stirred at room temperature for 16 h before being evaporated in vacuo to a white solid. The solid was triturated with diethyl ether and the white precipitation removed by filtration. The filtrate was evaporated in vacuo to give the title compound as a colourless oil (31.1 g). $^1$H NMR (CDCl$_3$) δ 7.99 (2H, m), 7.45–7.30 (5H, br m), 6.99 (2H, m), 5.12 (2H, s), 4.39 (2H, m), 1.11 (2H, m) and 0.08 (9H, s).

INTERMEDIATE 120

4-[(2-Trimethylsilyl)ethyloxycarbonyl]phenol

The title compound (21.5 g, 96%) was prepared from Intermediate 119 (31.1 g, 80 mmol) in a similar manner to Intermediate 50. $^1$H NMR (CDCl$_3$) δ 7.90 (2H, d, J 8.8 Hz), 6.86 (2H, d, J 8.8 Hz), 4.37 (2H, m), 1.08 (2H, m) and 0.07 (9H, s).

INTERMEDIATE 121

Benzyl-3-(2-chloro-4-pyrimidinyl)-3-(4-fluorophenyl)propanoate

The title compound (12.6 g, 78%) was prepared from Intermediate 2 (9.7 g, 43.6 mmol) and benzyl bromoacetate (7.05 ml, 44.5 mmol) in a similar manner to Intermediate 3. $^1$H NMR (CDCl$_3$) δ 8.45 (1H, d, J 5.1 Hz), 7.30 (7H, m), 7.00 (3H, m), 5.10 (2H, s), 4.50 (1H, m), 3.50 (1H, m) and 2.95 (1H. m). MS (ES) m/e 371 [M+H]$^+$.

INTERMEDIATE 122

Benzyl-3-(4-fluorophenyl)-3-[2-(4-{2-trimethylsilyl)ethyloxy carbonyl}phenoxy)-4-pyrimidinyl]proganoate The title compound (4.3 g, 87%) was prepared from Intermediate 120 (2.6 g, 10.9 mmol) and Intermediate 121 (3.23 g, 8.71 mmol) in a similar manner to Intermediate 15. $^1$H NMR (CDCl$_3$) δ 8.37 (1H, d, J 5.1 Hz), 8.10 (2H, d, J 8.9 Hz), 7.34–7.28 (3H, m), 7.30–7.17 (6H, m), 6.96 (2H, t, J 9.4 Hz), 6.88 (1H, d, J 5.1 Hz), 5.05 (1H, d, J 12.3 Hz), 5.0 (1H, d, J 12.3 Hz), 4.50 (1H, dd, J 8.7, 6.1 Hz), 4.43 (2H, m), 3.37 (1H, dd, J 16.4, 8.7 Hz), 2.89 (1H, dd, J 16.4, 6.6 Hz), 1.14 (2H, m) and 0.99 (9H, s). MS (ES) m/e 573 [M+H]h.

INTERMEDIATE 123

3-(4-Fluorophenyl)-3-[2-(4-{2-trimethylsilyl)ethyloxycarbonyl}phenoxy)-4-pyrimidinyl]propanoic acid To a stirred solution of Intermediate 122 (4.3 g, 7.6 mmol) and cyclohexene (40 ml) in degassed propan-2-ol under nitrogen was added 10% palladium on carbon (500 mg) and the mixture heated under reflux for 72 h. The reaction mixture was filtered through Celite® and the solvent removed in vacuo. The residue was purified by chromatography (99% dichloromethane,1% methanol-silica) to give the title compound (1.91 g, 52%). $^1$H NMR (CDCl$_3$) δ 8.39 (1H, d, J 5.0 Hz), 8.10 (2H, d, J 8.7 Hz), 7.25–7.18 (4H, m), 6.98 (2H, t, J 8.6 Hz), 6.88 (1H, d, J 5.0 Hz), 4.48 (1H, m), 4.46–4.09 (2H, m), 3.35 (1H, dd, J 17.0, 8.8 Hz), 2.84 (1H, dd, J 17.0, 6.1 Hz), 1.26–1.12 (2H, m) and 0.97 (9H, s). MS (ES) m/e 483 [M+H]+.

INTERMEDIATE 124

Ethyl-3-[2-(4-cyanophenol)-4-pyrimidinyl]propanoate

The title compound (2.2 g, 77%) was prepared from 4-cyanophenol (1.19 g, 10.0 mmol) and Intermediate 12 (2.15 g, 10.0 mmol) in a similar manner to Intermediate 13. The crude product was used without purification.

INTERMEDIATE 125

Ethyl-3-[2-{4-(aminomethyl)phenyl}-4-pyrimidinyl]propanoate

The title compound (0.6 g, 26%) was prepared from Intermediate 124 (2.2 g, 7.7 mmol) in a similar manner to Intermediate 21. $^1$H NMR (CDCl$_3$) δ 8.39 (1H, d, J 6.0 Hz), 7.36 (2H, d, J 8.0 Hz), 7.18 (2H, d, J 8.0 Hz), 6.92 (1H, d, J 6.0 Hz), 4.12 (2H, q, J 8.0 Hz), 3.92 (2H, s), 3.07 (2H, t, J 8.0 Hz), 2.83 (2H, t, J 8.0 Hz) and 1.23 (3H, t, J 8.0 Hz).

INTERMEDIATE 126

Ethyl-3-{2-(4-[(4,5-dihydro-1H-imidazol-2-ylamino)methyl]phenoxy}-4-pyrimidinyl)propanoate The title compound (0.38 g, 50%) was prepared from Intermediate 125 (0.6 g, 2.0 mmol) in a similar manner to Intermediate 48. $^1$H NMR (CDCl$_3$) δ 8.43 (1H, d, J 7.0 Hz), 7.40 (2H, d, J 8.0 Hz), 7.14 (2H, d, J 8.0 Hz), 6.97 (1H, d, J 7.0 Hz), 4.53 (2H, s), 4.09 (2H, t, J 8.0 Hz), 3.62 (4H, s), 3.03 (2H, t, J 8.0 Hz), 2.75 (2H, t, J 8.0 Hz) and 1.21 (3H, t, J 8.0 Hz).

INTERMEDIATE 127

Benzyl-4-[6-{4-methoxybenzyl)-N-methylamino}pyridin-2-yl]phenyl ether

The title compound (640 mg, 49%) was prepared from Intermediate 86 (1.279, 3.20 mmol) and methyl iodide (219 μl, 3.52 mmol) in a similar manner to Intermediate 102. $^1$H NMR (CDCl$_3$) δ 8.01 (2H, d, J 8. Hz), 7.51–7.31 (6H, m), 7.23 (2H, d, J 8.7 Hz), 7.03 (2H, d, J 8.8 Hz), 7.00 (1H, d, J 6.4 Hz), 6.85 (2H, d, J 8.7 Hz), 6.43 (1H, d, J 8.3 Hz), 5.13 (2H, s), 4.86 (2H, s), 3.80 (3H, s) and 3.10 (3H, s). MS (ES) m/e 411 [M+H]+.

INTERMEDIATE 128

4-[6-{(4-Methoxybenzyl)-N-methylamino}-pyridin-2-yl]phenol

The title compound (500 mg, 100%) was prepared from Intermediate 127 (640 mg, 1.62 mmol) in a similar manner to Intermediate 50. $^1$H NMR (CDCl$_3$) δ 7.94 (2H, d, J 8.7 Hz), 7.48 (1H, dd, J 8.3, 7.5 Hz), 7.22 (2H, d, J 8.7 Hz), 6.99 (1H, d, J 7.5 Hz), 6.86 (4H, d, J 8.3 Hz), 6.42 (1H, d, J 8.3 Hz), 4.85 (2H, s), 3.79 (3H, s) and 3.10 (3H, s). MS (ES) m/e 321 [M+H]+.

INTERMEDIATE 129 t-Butyl-3-[6-(4-{2-({4-methoxybenzyl}-N-methylamino)pyridin-2-yl}phenoxy)-4-pyrimidinyl]-3-(4-methoxycarbonylphenyl)propanoate The title compound (600 mg, 56%) was prepared from Intermediate 128 (500 mg, 1.62 mmol) and Intermediate 35 (670 mg, 1.78 mmol) in a similar manner to Intermediate 13. $^1$H NMR (CDCl$_3$) δ 8.38 (1H, d, J 5.0 Hz), 8.10 (2H, d, J 8.7 Hz), 7.96 (2H, d, J 8.3 Hz), 7.52 (1H, dd, J 8.4, 7.5 Hz), 7.37 (2H, d, J 8.3 Hz), 7.23 (4H, d, J 8.7 Hz), 7.07 (1H, d, J 8.5 Hz), 6.87 (1H, d, J 5.0 Hz), 6.85 (2H, d, J 8.7 Hz), 6.47 (1H, d, J 8.4 Hz), 4.87 (2H, s) 4.52 (1H, dd, J 8.6, 6.9 Hz), 3.90 (3H, s), 3.79 (3H, s), 3.31 (1H, dd, J 16.3, 8.6 Hz), 3.11 (3H, s), 2.83 (1H, dd, J 16.3, 6.9 Hz) and 1.42 (9H, s). MS (ES) m/e 661 [M+H]+.

INTERMEDIATE 130

Ethyl-3-(2-[N-benzyl-4-cyanoanilino]-4-pyrimidinyl)propanoate

To an ice cold suspension of Intermediate 81 (1.0 g, 3.38 mmol) in THF was added potassium bis(trimethylsilyl)amide (0.5 Min THF, 7.05 ml, 3.55 mmol). The solution was then cooled to −78° and benzyl bromide (0.8 ml, 6.76 mmol) was added. The reaction mixture was allowed to warm slowly to room temperature and stirred overnight, quenched with saturated sodium hydrogen carbonate solution and extracted into dichloromethane, dried over sodium sulphate and evaporated in vacuo. Purification by flash chromatography (98% dichloromethane, 2% methanol-silica) gave the title compound as a yellow oil (400 mg, 31%). $^1$H NMR (CDCl$_3$) δ 8.24 (1H, d, J 5.0 Hz), 7.56 (2H, d, J 8.8 Hz), 7.42 (2H, d, J 8.8 Hz), 7.32–7.16 (5H, m), 6.63 (11H, d, J 5.0 Hz), 5.35 (2H, s), 4.05 (2H, q, J 7.1 Hz), 2.96 (2H, t, J 7.1 Hz), 2.67 (2H, t, J 7.1 Hz) and 1.20 (3H, t, J 7.1 Hz). MS (ES) m/e 387 [M+M]+.

INTERMEDIATE 131

Ethyl-3-(2-[4-aminomethyl-N-benzylanilino]-4-pyrimidinyl)propanoate

The title compound (400 mg, 99%) was prepared from Intermediate 130 (400 mg, 1.04 mmol) in a similar manner to Intermediate 21. $^1$H NMR (CDCl$_3$) δ 8.02 (1H, d, J 5.2 Hz), 7.43 (2H, d, J 8.3 Hz), 7.26–7.15 (7H, m), 6.54 (1H, d, J 5.2 Hz), 5.19 (2H, s), 4.10–3.95 (4H, m), 2.95 (2H, t, J 7.1 Hz), 2.68 (2H, t, J 7.1 Hz) and 1.56 (3H, t, J 7.1 Hz). MS (ES) m/e 391 [M+H]+.

INTERMEDIATE 132

Ethyl-3-(2-[4-{(2-pyridinylamino)methyl}-N-benzylanilino]-4-pyrmidinyl)pronanoate The title compound (250 mg, 52%) was prepared from Intermediate 131 (400 mg, 1.02 mmol) in a similar manner to Intermediate 30. $^1$H NMR (CDCl$_3$) δ 8.17 (1H, d, J 5.0 Hz), 8.09 (1H, dd, J 5.0, 1.1 Hz), 7.42–7.36 (1H, m), 7.31 (2H, d, J 8.4 Hz), 7.27–7.19 (7H, m), 6.60–6.55 (1H, m), 6.49 (1H, d, J 5.0 Hz), 6.37 (1H, d, J 8.4 Hz), 5.24 (2H, s), 5.06–4.97 (1H, m), 4.47 (2H, d, J 5.7 Hz), 4.05 (2H, q, J 7.1 Hz), 2.93 (2H, t, J 7.1 Hz), 2.68 (2H, t, J 7.1 Hz) and 1.20 (3H, t, J 7.1 Hz). MS (ES) m/e 468 [M+H]+.

INTERMEDIATE 133

2-[4-(Benzyloxyo)phenyl]-N'-methylethanimidamide

To a cooled (0°) solution of trimethylaluminium (2.0 M solution in toluene, 3.25 ml) in toluene (50 ml) was added portionwise methylamine hydrochloride (438 mg, 6.5 mmol). The mixture was stirred at room temperature for 20 min, then 4-benzyloxyphenylacetonitrile (1.0 g, 4.47 mmol)

in toluene (2 ml) was added, and the mixture heated to reflux for 14 h. The mixture was allowed to cool and poured onto a slurry of log of silica in 50 ml of chloroform. The silica slurry was stirred for 30 min then filtered. The silica was washed with chloroform (100 ml) then the washings discarded. The silica plug was then washed with methanol (200 ml) and the methanol washings concentrated in vacuo to yield the title compound as a gummy solid (10 g, 94%). $^1$H NMR (d$^6$ DMSO) δ 7.43–7.21 (7H, m), 6.91 (2H, d, J 10.1 Hz), 5.21 (2H, s), 3.61 (2H, s) and 3.12 (3H, s). MS (ES) m/e 255 [M+H]$^+$.

INTERMEDIATE 134

2-(4-Hydroxyphenol)-N'-methylethanimidamide

The title compound (600 mg, 87%) was prepared from Intermediate 133 (1.03 g, 4.2 mmol) in a similar manner to Intermediate 50. $^1$H NMR (d$^6$ DMSO) δ 7.22 (2H, d, J 8.8 Hz), 6.72 (2H, d, J 8.8 Hz), 3.62 (2H, s) and 2.8 (3H, s). MS (ES) m/e 165 [M+H]$^+$.

INTERMEDIATE 135 t-Butyl-3-(4-fluorophenyl)-3-(2-{4-[(2-imino-2-methylamino)ethy]phenoxy}-4-pyrimidinyl) propanoate The title compound (350 mg, 16%) was prepared from Intermediate 134 (600 mg, 4.87 mmol) and Intermediate 11 (1.6 g, 4.8 mmol) in a similar manner to Intermediate 13. $^1$H NMR (CDCl$_3$+CD$_3$OD) δ 8.11 (1H, d, J 6.2 Hz), 7.31–6.71 (9H, m), 4.32 (1H, t, J 8.2 Hz), 3.82 (2H, s), 3.21 (1H, dd, J 15.2, 7.8 Hz), 2.72 (3H, s), 2.62 (1H, dd, J 15.0, 7.8 Hz) and 1.21 (9H, s). MS (ES) m/e 465 [M+H]$^+$.

INTERMEDIATE 136 t-Butyl-3-{2-[4-(N,N'-bis-boc{[amino(imono) methyl]amono}methyl) phenoxy]-4-pyrimidinyl}-3-[4-(methoxycarbonyl)phenyl]propanoate The title compound (1.1 g, 19%) was prepared from p-cyanophenol (0.95 g, 7.97 mmol) and Intermediate 35 (3.0 g, 7.97 mmol) sequentially by the methods used to prepare Intermediates 13, 21 and 27.1 H NMR (CDCl$_3$) δ 8.32 (1H, d, J 5.4 Hz), 7.95 (2H, d, J 8.4 Hz), 7.42–7.38 (4H, m), 7.14 (2H, d, J 8.6 Hz), 6.89 (1H, d, J 5.4 Hz), 4.68 (2H, s), 4.51 (1H, t, J 8.2 Hz), 3.89 (3H, s), 3.31 (1H, dd, J 16.4, 8.4 Hz), 2.81 (1H, dd, J 16.2, 8.4 Hz), 1.52 (9H, s), 1.49 (9H, s) and 1.31 (9H, s). MS (ES) 725 [M+H]$^+$.

INTERMEDIATE 137

N''-[4-(Benzyloxy)benzyl]-2-pyridinecarboximidamide

The title compound (800 mg, 84%) was prepared from Intermediate 77 (1.0 g, 4.9 mmol) 2-cyanopyridine (312 mg, 3.0 mmol) and triethylaluminium in a similar manner to Intermediate 133. $^1$H NMR (d$^6$DMSO) δ 8.58 (1H, d, J 10.0 Hz), 8.18 (1H, d, J 10.0 Hz), 7.84 (1H, t, J 10.0 Hz), 7.51–7.31 (6H, m), 7.21 (1H, t, J 10 Hz), 7.01–6.92 (3H, m), 5.08 (2H, s) and 4.30 (2H, s). MS (ES) m/e 318 [M+H]$^+$.

INTERMEDIATE 138

N'-(4-Hydroxybenzyl)-2-pyridinecarboximidamide

The title compound (470 mg, 82%) was prepared from Intermediate 137 (800 mg, 2.51 mmol) in a similar manner to Intermediate 50. $^1$H NMR (d$^6$ DMSO) δ 8.72 (1H, d, J 8.0 Hz), 8.17 (1H, d, J 8.2 Hz), 7.82 (1H, t, J 8.2 Hz), 7.49 (1H, t, J 8.2 Hz), 7.19 (2H, d, J 8.3 Hz), 6.68 (2H, d, J 8.3 Hz) and 4.22 (2H, s). MS (ES) m/e 228 [M+H]$^+$.

INTERMEDIATE 139 t-Butyl-3-(4-fluorophenyl)-3-{2-(4-[({imino(2-pyridinyl)methyl}amino) methyl]phenoxy)4-pyromidinyl}propanoate The title compound (200 mg, 15%) was prepared from Intermediate 138 (476 mg, 2.09 mmol) and Intermediate 11 (702 mg, 2.09 mmol) in a similar manner to Intermediate 13. $^1$H NMR (CDCl$_3$) δ 8.53 (1H, d, J 7.8 Hz), 8.32 (1H, d, J 7.8 Hz), 7.84 (1H, t, J 7.8 Hz), 7.42–6.91 (10H, m), 6.81 (1H, d, J 6.2 Hz), 4.72 (2H, s), 4.38 (1H, t, J 8.6 Hz), 3.21 (1H, dd, J 16.2, 8.6 Hz), 2.72 (1H, dd, J 16.2, 8.6 Hz) and 1.28 (9H, s). MS (ES) m/e 528 [M+H]$^+$.

INTERMEDIATE 140

Resin bound 3-(4-Fluorophenyl)-3-[2-(4-{2-[trimethylsily]ethyloxycarbonyl}phenoxy)-4-pyrimidinyl]propanoic acid A slurry of Wang resin (Advanced Chem Tech, 1.16 g, 0.70 mmol/g, 0.81 mmol equivalent) in a mixture of dichloromethane (4 ml) and DMF (4 ml) was treated with Intermediate 123, DMAP (99 mg, 0.81 mmol) and N,N'-diisopropylcarbodiimde (0.20 g, 1.63 mmol). The resulting mixture was agitated at room temperature for 48 h, then filtered and the resin washed thoroughly with dichloromethane, DMF and methanol to give the derivatised resin (Intermediate 140).

INTERMEDIATE 141

Resin bound 3-(4-Fluorophenyl)-3-[2-(4-carboxyphenoxy)-4-pyrimidinyl]propanoic acid Derivatised resin (Intermediate 140) (2.60 g) was suspended in DMF (10 ml) and treated with tetrabutylammonium fluoride (1.0M solution in THF, 18 ml, 18 mmol). The resulting mixture was agitated for 1 h at room temperature then filtered and the resin washed thoroughly with dichloromethane, DMF and methanol to give the derivatised resin (Intermediate 141).

INTERMEDIATE 142

Resin bound 3-(4-Bromophenyl)-3-[2-(4-({2-pyrodinylamino}methyl) phenoxy)-4-pyrimidinyl] propanoic acid A slurry of Wang resin (2.0 g, 0.70 mmol/g, 1.40 mmol equivalent) in a mixture of dichloromethane (10 mL) and DMF (10 mL) was treated with the compound of Example 45 (2.10 g, 4.20 mmol), DMAP (171 mg, 1.40 mmol) and N,N'-diisopropylcarbodiimide (0.70 mL, 4.20 mmol). The resulting mixture was agitated at room temperature for 48 h, then filtered and the resin washed thoroughly with dichloromethane, DMF and methanol to give the derivatised resin (Intermediate 142).

INTERMEDIATE 143

2-Chloro-4-[3-methoxycarbonylphenyl]methyl) pyrimidine

The title compound (2.4 g, 86%) was prepared from methyl 3-bromomethylbenzoate (2.5 g, 10.9 mmol) and 2,4-dichloropyrimidine (1.63 g, 10.9 mmol) in a similar manner to Intermediate 2. $^1$H NMR (d$^6$ DMSO) δ 8.67 (1H, d, J 6.5 Hz), 7.90 (1H, br s), 7.84 (1H, t, J 6.9 Hz), 7.54 (1H, m), 7.47 (2H, m), 4.20 (2H, s), 3.82 (3H, s).

INTERMEDIATE 144

Methyl-3-(2-chloro-4-pyrimidinyl)-3-(3-methoxycarbonylphenyl) proganoate

The title compound (2.60 g, 86%) was prepared from Intermediate 143 (2.38 g, 9.07 mmol) in a similar manner to Intermediate 3. $^1$H NMR (d$^6$ DMSO) δ 8.68 (1H, d, J 6.1 Hz), 7.92 (1H, s), 7.81 (1H, d, J 8.5 Hz), 7.59 (1H, d, J 6.1 Hz), 7.47 (1H, t, J 7.8 Hz), 4.72 (1H, t, J 7.9 Hz), 3.86 (3H, s), 3.53 (3H, s), 3.39 (1H, dd, J 17.0, 8.5 Hz), 3.08 (1H, dd, 17.0, 7.8 Hz).

INTERMEDIATE 145

Methyl-3-(3-methoxycarbonylphenyl)-3-(2-[4-{(2-pyridinylamino)methyl}phenoxy]-4-pyrimidinyl) propanoate The title compound (0.98 g, 51%) was prepared from Intermediate 144 (1.30 g, 3.89 mmol) and Intermediate 1 (0.78 g, 3.89 mmol) in a similar manner to Intermediate 13. $^1$H NMR (d$^6$ DMSO) δ 8.46 (1H, d, J 6.5 Hz), 7.94 (1H, d, J 5.2 Hz), 7.90 (1H, s), 7.81 (1H, d, J 7.8 Hz), 7.61 (1H, d, J 7.8 Hz), 7.42 (1H, t, J 8.0 Hz), 7.40–7.30 (3H, m), 7.27 (1H, d, J 6.5 Hz), 7.10 (2H, d, J 8.5 Hz), 7.04 (1H, t, J 6.5 Hz), 6.51–6.43 (2H, m), 4.64 (1H, t, J 6.9 Hz), 4.49 (2H, br s), 3.86 (3H, s), 3.49 (3H, s), 3.28 (1H, dd, J 16.5, 8.5 Hz), 2.78 (1H, dd, J 16.5, 7.8 Hz).

EXAMPLE 1

3-{2-[4-({[Amino(imino)methyl]amino}methyl)anilno]-4-pyromidinyl}-3-(4-fluorophenyl)propanoic acid (i) Intermediate 6 (200 mg, 0.55 mmol) and N,N'-bis-boc-1-guanylpyrazole (169 mg, 0.55 mmol) were stirred in acetonitrile (2 ml) at room temperature overnight, then heated under reflux for 2 h. The reaction was concentrated in vacuo and chromatographed (ethyl acetate-silica) to yield 3-{2-[4-(N,N'-bis-boc{[amino(imino)methyl]amino}methyl)anilino]-4-pyrimidinyl}-3-(4-fluorophenyl)propanoic acid (100 mg). $^1$H NMR (CDCl$_3$) δ (v. broad spectrum). 8.52 (1H, br m), 8.05 (2H, br m), 7.50 (2H, br m), 7.12 (2H, br m), 7.04 (1H, br m), 6.80 (2H, br m), 6.30 (1H, br m), 4.50 (2H, br m), 4.39 (1H, br m), 3.18 (1H, br m), 2.70 (1H, br m), 1.49 (9H, s) and 1.43 (9H, s). MS (ES) m/e 609 [M+H]$^+$.

(ii) The 3-{2-[4-(N,N'-bis-boc{[amino(imino)methyl]amino}methyl) anilino]-4-pyrimidinyl}-3-(4-fluorophenyl) propanoic acid (100 mg, 0.16 mmol) in dichloromethane (20 ml) with trifluoroacetic acid (4 ml) was stirred at room temperature for 2 h. The reaction was concentrated in vacuo and purified by HPLC (55% water, 45% methanol, 0.1% trifluoroacetic acid-C$_{18}$ reverse phase silica) to yield the title compound (60 mg). $^1$H NMR (CDCl$_3$) δ 8.27 (1H, d, J 5.2 Hz), 7.72 (2H, d, J 8.7 Hz), 7.38 (2H, m), 7.36 (2H, d, J 8.7 Hz), 7.03 (2H, t, J 7.8 Hz), 6.71 (1H, d, J 5.2 Hz), 4.48 (1H, m), 4.37 (2H, s), 3.39 (1H, dd, J 16.5, 8.7 Hz) and 2.91 (1H, dd, J 16.5, 7.8 Hz). MS (ES) m/e 409 [M+H]$^+$.

EXAMPLE 2

Methyl-3-(4-fluorophenyl)-3-(2-{4-[(2-pyridinylamino)methyl]phenoxy}-4-pyramidinyl) propanoate The title compound was prepared from Intermediate 1 (0.68 g, 3.4 mmol) and Intermediate 3 (1.0 g, 3.4 mmol) in a similar manner to Intermediate 13. $^1$H NMR(CDCl$_3$) δ 8.35 (1H, d, J 5.1 Hz), 8.11 (1H, m), 7.41 (3H, m), 7.22 (2H, m), 7.14 (2H, d, J 8.6 Hz), 6.97 (2H, t, J 8.7 Hz), 6.85 (1H, d, J 5.0 Hz), 6.60 (1H, m), 6.40 (1H, d, J 8.4 Hz), 4.88 (1H, br t), 4.55 (2H, d, J 5.8 Hz), 4.49 (1H, dd, J 8.5, 6.7 Hz), 3.5 (3H, s), 3.34 (1H, dd, J 8.51 Hz) and 2.84 (1H, dd, J 16.2, 6.7 Hz). MS (ES) m/e 459 [M+H]$^+$.

EXAMPLE 3

3-(4-Fluorophenyl-3-(2-{4-[2-pyrodinylamino)methyl]phenoxy}-4-pyrimidinyl)propanoic acid The compound of Example 2 (422 mg, 0.92 mmol) in methanol:water (4 ml 1:1) was treated with 0.101M sodium hydroxide (9.21 ml, 0.92 mmol) and heated under reflux for 18 h. The methanol was removed in vacuo and the resulting aqueous residue neutralised with 2M hydrochloric acid. The resulting cloudy solution was extracted into dichloromethane, dried over magnesium sulphate and concentrated in vacuo. Chromatography (ethyl acetate-silica) yielded the title compound as a white foam. $^1$H NMR (d$^6$ DMSO) δ 8.33 (1H, d, J 5.1 Hz), 7.84 (1H, d, J 6.7 Hz), 7.54 (1H, t, J 8.4 Hz), 7.31 (2H, d, J 8.5 Hz), 7.19 (2H, m), 7.10 (2H, d, J 8.6 Hz), 6.93 (2H, t, J 8.7 Hz), 6.83 (1H, d, J 5.1 Hz), 6.61 (1H, t, J 6.1 Hz), 6.53 (1H, d, J 8.7 Hz), 4.53 (1H, q, J 5.3 Hz), 4.44 (2H, s), 3.23 (1H, dd, J 16.5, 9.7 Hz) and 2.69 (1H, dd, J 16.5, 5.4 Hz). MS (ES) m/e 445 [M+H]$^+$.

EXAMPLE 4

Methyl-3-(3,5-difluorophenyl)-3-(2-{4-[(2-pyridinylamino)-methyl]phenoxy}-4-pyrmidinyl) propanoate The title compound (410 mg, 27%) was prepared from Intermediate 1 (0.64 g, 3.2 mmol) and Intermediate 8 (1.0 g, 3.2 mmol) in a similar manner to Intermediate 13. $^1$H NMR (CDCl$_3$) δ 8.41 (1H, d J 5.0 Hz), 7.15 (2H, d, m), 6.90 (1H, d, J 5.0 Hz), 6.81 (2H, m), 6.62 (2H, m), 6.42 (1H, d, J 8.4 Hz), 5.61 (1H, br s), 4.59 (2H, d, J 6.3 Hz), 4.41 (1H, dd, J 8.5, 6.4 Hz), 3.60 (3H, s), 3.28 (1H, dd, J 8.5, 6.4 Hz) and 2.81 (1H, dd, J 8.5, 6.4 Hz). MS (ES) m/e 477 [M+H]$^+$.

EXAMPLE 5

3-(3,5-Difluorophenyl)-3-(2-{4-[(2-pyridinylamino)-methyl]phenoxy}-4-pyrimidinyl)propanoic acid lithium salt The compound of Example 4 (40 mg, 0.088 mmol) in THF (10 ml) and water (5 ml) was stirred at room temperature and lithium hydroxide monohydrate (37 mg, 0.88 mmol) added. The solution was stirred at room temperature for 72 h, then the solvents were removed in vacuo, and the crude white solid partitioned between ethyl acetate (10 ml) and water (10 ml). The water layer was freeze dried and the title compound was obtained as a white solid. $^1$H NMR (d$^6$ DMSO) δ 8.29 (1H, d, J 5.1 Hz), 7.81 (1H, d, J 5.1 Hz), 7.21 (4H, m), 7.09 (1H, d, J 5.1 Hz), 6.80 (4H, m), .6.52 (1H, t, J 10.0 Hz), 6.42 (1H, t, J 5.8 Hz), 6.39 (1H, d, J 8.6 Hz), 4.42 (1H, t, J 7.9 Hz), 4.34 (2H, s), 2.98 (1H, dd, J 15.6, 8.4 Hz) and 2.77 (1H, dd, J 15.2, 7.5 Hz). MS (ES) m/e 463 [M+H]$^+$.

EXAMPLE 6 t-Butly-3-[5-(ethoxycarbonyl)-3-furyl]-3-(2-{4-[(2-pyridinylamino) methyl]phenoxy}-4-pyrimidinyl) propanoate The title compound (300 mg, 21%).was prepared from Intermediate 1 (1.09, 2.63 mmol) and Intermediate 10 (1.0 g, 2.63 mmol) in a similar manner to Intermediate 13. $^1$H NMR (CDCl$_3$) δ 8.39 (1H, d, J 6.5 Hz), 8.02 (1H, m), 7.49 (1H, m), 7.36 (2H, d, J 8.6 Hz), 7.12 (2H, d, J 8.6 Hz), 7.05 (1H, d, J 5.5 Hz), 6.97 (1H, d, J 6.5 Hz), 6.68 (1H, t, J 8.6 Hz), 6.50 (1H, d, J 8.6 Hz), 6.22 (1H, d, J 5.5 Hz), 4.60 (1H, t, J 8.6 Hz), 4.52 (2H, s), 4.31 (2H, m), 3.14 (1H, dd, J 8.6, 6.3 Hz), 2.91 (1H, dd, J 8.6, 6.3 Hz) and 1.32 (12H, m). MS (ES) m/e 544 [M+H]$^+$.

EXAMPLE 7

3-[5-(Ethoxycarbonyl)-3-furyl]-3-(2-{4-[(2-pyrndinylamino)methyl]phenoxy}-4-pyrimidinyl) propanoic acid trifluoroacetic acid salt The compound of Example 6 (300 mg) in dichloromethane (2 ml) and trifluoroacetic acid (1 ml) was stirred for 12 h. The solvent was then removed and the crude product subjected to radial chromatography (94% dichloromethane, 5% methanol, 1% trifluoroacetic acid-4 mm silica plate) to yield the title compound (180 mg, 67%). $^1$H NMR (d$^6$ DMSO) δ 8.49 (1H, d, J 6.0 Hz), 7.92 (1H, d, J 8.0 Hz), 7.81 (1H, t, J 8.0 Hz), 7.42 (2H, d, J 8.0 Hz), 7.22 (4H, m), 7.02 (1H, d, J 8.0 Hz), 6.81 (1H, t, J 8.0 Hz), 6.49 (1H, d, J 5.5 Hz), 4.62 (1H, t, J 7.7 Hz), 4.58 (2H, s), 4.25 (2H, q, J 6.5 Hz), 3.15 (1H, dd, J 8.6, 6.3 Hz), 2.91 (1H, dd, J 8.6, 6.3 Hz) and 1.25 (3H, t, J 8.6 Hz).

EXAMPLE 8

3-(2-{4-[(2-Pyridylamino)methyl]phenoxy}-4-pynrmidinyl)propanoic acid

The title compound (0.44 g, 50%) was prepared from Intermediate 13 (0.91 g, 2.4 mmol) in a similar manner to the compound of Example 3. $^1$H NMR (d$^6$ DMSO) δ 8.41 (1H, d, J 5 Hz), 7.44 (1H, d, J 6 Hz), 7.40–7.30 (3H, m), 7.13 (1H, d, J 5 Hz), 7.09 (2H, d, J 8 Hz), 7.02 (1H, br t, J 6 Hz), 6.52–6.42 (2H, m), 4.47 (2H, br s), 2.90 (2H, t, J 7 Hz) and 2.62 (2H, t, J 7 Hz). MS (ES) m/e 351 [M+H]$^+$.

EXAMPLE 9

3-(2-}4-[(2-Pyridinylamino)methyl]phenoxy}-4-pyrimidinyl)proenoic acid

The title compound (0.23 g, 22%) was prepared from Intermediate 15 (0.48 g, 1.27 mmol) in a similar manner to the compound of Example 3. $^1$H NMR (d$^6$ DMSO) δ 8.62 (1H, d, J 5 Hz), 7.95 (1H, d, J 1 Hz), 7.47 (1H, d, J 5 Hz), 7.37 (2H, d, J 9 Hz), 7.40–7.34 (1H, m), 7.29 (1H, d, J 16 Hz), 7.13 (2H, d, J 9 Hz), 7.04 (1H, t, J 6 Hz), 6.88 (1H, d, J 16 Hz), 6.51 (1H, d, J 8 Hz), 6.48–6.45 (1H, m) and 4.48 (2H, d, J 5 Hz). MS (ES) m/e 349 [M+H]$^+$.

EXAMPLE 10

3-(4-Cyanophenyl)-3-(-{4-[(2-pyridinylamino) methyl]phenoxy}-4-pyrimidinyl)propanoic acid tirfluoroacetic acid salt The title compound (775 mg, 80%) was prepared from Intermediate 1 (428 mg, 2.14 mmol) and Intermediate 17 (660 mg, 2.14 mmol) by the methods used to prepare Intermediate 13 and the compound of Example 7. $^1$H NMR (d$^6$ DMSO) δ 8.43 (1H d, J 5.2 Hz), 7.94 (1H, s), 7.72 (2H, d, J 7.9 Hz), 7.50 (2H, d, J 7.9 Hz), 7.41–7.21 (3H, m), 7.22 (H, d, J 5 Hz), 7.11–6.92 (3H, m), 6.51–6.32 (2H, m), 4.52 (1H, t, J 5.1 Hz), 4.41 (2H, s), 3.18–3.01 (1H, m) and 2.87–2.62 (1H, m). MS (ES) m/e 452 [M+H]$^+$.

EXAMPLE 11

3-(4-Fluorophenyl)-3-(2-[4-{(2-pyridinylamino) carbonyl}phenoxy]-4-pyrimidenyl)propanoic acid trifluoroacetic acid salt The title compound (75 mg, 17%) was prepared from Intermediate 19 (220 mg, 0.97 mmol) and Intermediate 11 (326 mg, 0.97 mmol) in a similar manner to the compound of Example 10. $^1$H NMR (d$^6$ DMSO) δ 8.49 (1H, d, J 5.4 Hz), 8.32 (1H, d, J 5.1 Hz), 8.21–8.05 (3H, m,), 7.91–7.80 (1H, m), 7.41–7.06 (8H, m), 4.52 (1H, t, J 7.1 Hz), 3.22–3.11 (1H, m), 2.88–2.71 (1H, m). MS (ES) m/e 459 [M+H]$^+$.

EXAMPLE 12

3-[2-(4-{[(4-Amino-2-pyridinyl)amino] methyl}phenoxy)-4-pyrimidinyl]-3-(4-fluorophenyl) propanoic acid trifluoroacetic acid salt The title compound (100 mg, 18%) was prepared from Intermediate 23 (500 mg, 0.92 mmol) in a similar manner to the compound of Example 7. $^1$H NMR (d$^6$ DMSO) δ 8.42 (1H, d, J 5.2 Hz), 7.49–7.28 (6H, m), 7.21–7.02 (5H, m), 6.82 (1H, d, J 5.1 Hz), 4.51–4.42 (3H, m), 3.11 (1H, dd, J 15.5, 8.1 Hz), 2.72 (1H, dd, J 15.5, 7.9 Hz). MS (ES) m/e 460 [M+H]$^+$.

EXAMPLE 13

3-(2-[4-{(1H-1,3-Benzimidazol-2-yl-amino) methyl}phenoxy]-4-pyrimidinyl)-3-(4-fluorophenyl) propanoic acid trifluoroacetic acid salt The title compound (200 mg, 65%) was prepared from Intermediate 24 (350 mg, 0.64 mmol) in a similar manner to the compound of Example 7. $^1$H NMR (d$^6$ DMSO) δ 8.42 (1H, d, J 5.0 Hz), 7.47 (2H, d, J 8.4 Hz), 7.25 7.39 (4H, m), 7.22–7.11 (4H, m), 7.18–7.1 (2H, m), 4.61 (2H, d, J 5.1 Hz), 4.51 (1H, t, J 7.9 Hz), 3.15 (1H, dd, J 16.6, 8.6 Hz), 2.75 (1H, dd, J 16.5, 6.7 Hz). MS (ES) m/e 484 [M+H]$^+$.

EXAMPLE 14

3-(2-[4-([{Amino(imino)methyl}amino]methyl) benzyl]-4-pyrimidinyl)-3-(4-fluorophenyl)propanoic acid Intermediate 26 (620 mg, 1.47 mmol) was dissolved in dichloromethane (10 ml) and N,N'bis-boc guanyl triflate added (570 mg, 1.47 mmol). The mixture was stirred for 12 h then trifluoroacetic acid (3 ml) was added, and the mixture stirred for a further 2 h. The solvents were removed in vacuo, and the crude foam subjected to radial chromatography (100% dichloromethane→10% methanol, 90% dichloromethane+1 drop trifluoroacetic acid-4 mm silica plate). The title compound was isolated as an off white foam (130 mg, 22%). $^1$H NMR (d$^6$ DMSO) δ 8.54 (1H, d, J 5.5 Hz), 7.99–7.90 (1H, m), 7.39–6.99 (9H, m), 4.48 (1H, t, J 8.6 Hz), 4.31 (2H, d, J 7.5 Hz), 4.15 (2H, s), 3.32, 3.15 (1H, m), 2.91–2.79 (1H, m). MS (ES) m/e 408 [M+H]$^+$.

EXAMPLE 15

3-(2-[4-([{Amino(imino)methyl}amino]methyl) phenoxyl-4-pyrmidinyl)-3-(4-fluorophenyl) propanoic acid The title compound (130 mg, 70%) isolated as a bis hydrate mono trifluoroacetic acid salt was prepared from Intermediate 27 (300 mg, 0.45 mmol) in a similar manner to the compound of Example 7. $^1$H NMR (d$^6$ DMSO) δ 8.41 (1H, d, J 5.2 Hz), 8.04–7.91 (1H, m), 7.41–7.02 (9H, m), 4.48 (1H, t, J 8.2 Hz), 4.37 (2H, d, J 7.6 Hz), 3.14 (1H, dd, J 16.5, 8.2 Hz), 2.81 (1H, dd, J 16.5, 8.2 Hz). MS (ES) m/e 410 [M+H]$^+$.

EXAMPLE 16

3-(4-Fluorophenyl)-3-(2-[4{(2-pyridinylamino) methyl}anilino]-4-pyrimidinyl)propanoic acid The title compound (57 mg, 34%) was prepared from Intermediate 30 (0.18 g, 0.38 mmol) in a similar manner to the compound of Example 3. $^1$H NMR (CDCl$_3$) δ 8.14 (1H, d, J 6.0 Hz), 7.85 (1H, d, J 4.0 Hz), 7.81 (1H, br s), 7.58–7.42 (3H, m), 7.33–7.13 (4H, m), 6.95 (2H, t, J 9.0 Hz), 6.60–6.49 (2H, m), 6.42 (1H, d, J 8.0 Hz), 4.53 (1H, dd, J 8.0, 6.0 Hz), 3.41 (1H, dd, J 16.0, 10.0 Hz) and 2.83 (1H, dd, J 16.0, 6.0 Hz). MS (ES) m/e 444 [M+H]$^+$.

EXAMPLE 17

3-Phenyl-3-(2-[4-{(2-pyridinylamino) methyl}phenoxy]-4-pyrimidinyl) propanoic acid trifluoroacetic acid salt The title compound (370 mg, 34%) was prepared from Intermediate 33 (1.2 g, 2.4 mmol) in a similar manner to the compound of Example 7. $^1$H NMR (d$^6$ DMSO) δ 8.91 (1H, br s), 8.41 (1H, d, J 5.2 Hz), 7.91 (1H, d, J 6.8 Hz), 7.85 (1H, t, J 8.6 Hz), 7.41 (2H, d, J 8.6 Hz), 7.35–7.10 (8H, m), 7.05 (1H, d, J 8.6 Hz), 6.82 (1H, t, J 6.8 Hz), 4.58 (2H, s), 4.49 (1H, t, J 8.6 Hz), 3.18 (1H, dd, J 16.4, 7.2 Hz) and 2.78 (1H, dd, J 15.8, 8.6 Hz). MS (ES) m/e 427 [M+H]$^+$.

EXAMPLE 18

3-[4-(Methoxycarbonyl)phenyl]-3-(2-{4-[(2-pyridinylamino)methyl]phenoxy}-4-pyrnmidinyl) pronanoic acid trifluoroacetic acid salt The title compound (260 mg, 75%) was prepared from Intermediate 36 (310 mg, 0.57 mmol) in a similar manner to the compound of Example 7. $^1$H NMR (d$^6$ DMSO) δ 8.39 (1H, d, J 8.6 Hz), 7.92 (1H, d, J 5.1 Hz), 7.81 (2H, d, J 8.6 Hz), 7.41 (2H, d, J 8.6 Hz), 7.39–7.31 (3H, m), 7.21 (1H, d, J 5.1 Hz), 7.08–6.99 (3H, m), 6.52–6.41 (2H, m), 4.52 (1H, t, J 5.1 Hz), 4.45 (2H, d, J 5.1 Hz), 3.78 (3H, s), 3.25–3.21 (1H, m) and 2.88–2.72 (1H, m). MS (ES) m/e 485 [M+H]$^+$.

EXAMPLE 19 t-Butyl-3-(4-benzoicacid)-3-(2-[4-{(2-pyridinylamino)methyl}phenoxy]-4-pyrimidinyl) propanoate The title compound was prepared from Intermediate 36 (3.1 g, 5.7 mmol) in a similar manner to the compound of Example 5. $^1$H NMR (CDCl$_3$) δ 8.38 (1H, d, J 5.1 Hz), 7.96 (3H, m), 7.52 (1H, m), 7.42 (2H, 2, J 8.4 Hz), 7.28 (2H, d, 7.7 Hz), 7.10 (2H, d, J 8.5 Hz), 6.93 (1H, d, J 5.1 Hz), 6.62 (1H, m), 6.50 (1H, m), 4.55 (2H, br s), 4.47 (1H, m), 3.20 (1H, dd, J 16.3, 8.8 Hz), 2.81 (1H, dd, J 16.2, 6.7 Hz), and 1.32 (9H, 2). MS (ES) m/e 527 [M+H]$^+$.

EXAMPLE 20

3-(4-[2-Aminoethyl]benzamide)-3-(2-[4-{(2-pyridinylamino)methyl}phenoxy]-4-pyrimidinyl) propanoic acid trifluoroacetic acid salt The title compound (1.0 g, 80%) was prepared from Intermediate 37 (1.1 g, 1.6 mmol) in a similar manner to the compound of Example 7. $^1$H NMR (d$^6$ DMSO) δ 8.45 (1H, d, J 5.1 Hz), 8.20 (1H, br s), 7.98 (1H, m), 7.78 (2H, d, J 8.4 Hz), 7.52 (1H, m), 7.40 (4H, m), 7.25 (1H, m), 7.25 (2H, m), 6.68 (1H, m), 6.58 (1H, m), 4.57 (3H, m), 3.55 (2H, m), 3.21 (1H, dd, J 16.3, 7.9 Hz), 3.05 (2H, m) and 2.90 (1H, dd, J 16.2, 5.7 Hz). MS (ES) m/e 513 [M+H]$^+$.

EXAMPLE 21

3-(4-Benzoic acid)-3-(2-[4-{(2-pyradinylamino) methyl}phenoxy]-4-pyrimidinyl)propanoic acid trifluoroacetic acid salt The title compound (148 mg, 83%) was prepared from the compound of Example 19 (200 mg, 0.38 mmol) in a similar manner to the compound of Example 7. $^1$H NMR (CDCl$_3$) δ 8.24 (1H, d, J 5.1 Hz), 7.78 (2H, d, J 8.3 Hz), 7.75 (2H, m), 7.26 (3H, m), 7.16 (2H, d, J 8.3 Hz), 7.05 (2H, d, J 8.5 Hz), 6.8 (1H, d, J 5.1 Hz), 6.72 (2H, m), 4.48 (2H, s), 4.42 (1H, m), 3.13 (1H, dd, J 16.8, 8.9 Hz), 2.66 (1H, dd, J 16.9, 6.0 Hz). MS (ES) m/e 471 [M+H]$^+$.

EXAMPLE 22

3-[2-(4-[({Amino(imono)methyl}amino)methyl]-N-methylaniliino)-4-pyrimidinyl]-3-(4-fuorophenyl) nropanlooc acid trifluoroacetic acid salt The title compound (536 mg, 83%) was prepared from Intermediate 40 (825 mg, 1.2 mmol) in a similar manner to the compound of Example 7. $^1$H NMR (d$^6$ DMSO) δ 8.17 (1H, d, J 5.0 Hz), 8.07 (1H, br t, J 5.7 Hz), 7.36–7.29 (6H, m), 7.10 (2H, t, J 8.9 Hz), 6.64 (1H, d, J 5.0 Hz), 4.40–4.30 (3H, m), 3.47 (3H, s), 3.16 (1H, dd, J 16.3, 8.7 Hz), 2.75 (1H, dd, J 16.3, 6.6 Hz), MS (ES) m/e 423 [M+H]$^+$.

EXAMPLE 23

3-(4-Fluorophenyl)-3-(2-{4-[(3,4,5,6-tetrahydro-2H-azepin-7-ylamino) methyllphenoxy}-4-pyrimidonyl) propanoic acid trifluoroacetic acid salt The title compound (106 mg, 60%) was prepared from Intermediate 42 (200 mg, 0.39 mmol) in a similar manner to the compound of Example 7. 1H NMR (d$^6$ DMSO) δ 9.77 (1H, br t), 9.38 (1H, br t), 8.44 (1H, d, J 5.1 Hz), 7.41 (4H, m), 7.28 (3H, m), 7.17 (2H, d, J 8.9 Hz), 4.55 (1H, t, J 6.8 Hz), 4.48 (2H, br d, J 4.3 Hz), 3.47 (2H, v br s), 3.24 (1H dd, J 16.5, 7.8 Hz), 2.86 (1H, dd, J 16.5, 6.9 Hz), 1.72 (4H, m) and 1.62 (2H, m).

EXAMPLE 24

3-(4-Fluorophenyl)-3-{2-[4-(1H-imidazol-ylmethyl) phenoxy]-4-pyrimidinyl}propanoic acid trifluoroacetic acid salt The title compound (500 mg, 76%) was prepared from Intermediate 47 (750 mg, 1.54 mmol) in a similar manner to the compound of Example 7. $^1$H NMR (d$^6$ DMSO) δ 9.28 (1H, s), 8.43 (1H, d, J 5.0 Hz), 7.82 (1H, t, J 1.7 Hz), 7.70 (1H, t, J 1.7 Hz), 7.48 (2H, d, J 8.6 Hz), 7.34 (2H, dd, J 5.5, 8.8 Hz), 7.23 (3H, m), 7.10 (2H, t, J 8.9 Hz), 5.45 (2H, s), 4.51 (1H, t, J 7.7 Hz), 3.18 (1H, dd, J 16.6, 8.8 Hz) and 2.83 (1H, dd, J 16.6, 6.7 Hz). MS (ES) m/e 419 [M+H]$^+$.

EXAMPLE 25

3-(2-{4-[(4,5-Dihydro-1H-imidazol-2-ylamino) methy]phenoxy}-4-pyrimidinyl)-3-(4-fluorophenyl) propanoic acid trifluoroacetic acid salt The title compound (120 mg, 45%) was prepared from Intermediate 48 (268 g, 0.61 mmol) in a similar manner to the compound of Example 7. $^1$H NMR (d$^6$ DMSO) δ 8.74 (1H, m), 8.43 (1H, d, J 5.0 Hz), 7.33 (4H, m), 7.15 (5H, m), 4.51 (1H, t, J 7.67 Hz), 4.40 (2H, br d, J 6.1 Hz), 3.60 (4H, br m), 3.19 (1H, dd, J 16.6, 8.75 Hz), 2.83 (1H, dd, J 16.6, 6.6 Hz). MS (ES) m/e 436 [M+H]$^+$.

EXAMPLE 26

3-(4-Fluorophenyl)-3-{2-[4-(1H-1,2,4-triazol-1-ylmethyl)phenoxy]-4-pyrimidinyl}propanoic acid trifluoroacetic acid salt The title comDound (0.7 g, 71%) was prepared from Intermediate 51 (1.14 g, 2.34 mmol) in a similar manner to the compound of Example 7. $^1$H NMR (d$^6$ DMSO) δ 8.69 (1H, s), 8.42 (1H, d, J 5.1 Hz), 8.00 (1H, s), 7.36–7.31 (4H, m), 7.20 (1H, d, J 5.1 Hz), 7.17–7.07 (4H, m), 5.44 (2H, s), 4.51 (1H, t, J 8.6 Hz), 3.18 (1H, dd, J 16.5, 8.7 Hz) and 2.80 (1H, dd, J 16.5, 6.7 Hz). MS (ES) m/e 420 [M+H]$^+$.

EXAMPLE 27

3-{2-[4-(1H-1,3-Benzyimidazol-1-ylmethyl)phenoxy]-4-pyrimidinyl}-3-(4-fluorophenyl)propanoic acid trifluoroacetic acid salt The title compound (250 mg, 31%) was prepared from Intermediate 54 (0.91 g, 1.74 mmol) in a similar manner to the compound of Example 7. $^1$H NMR (d$^6$ DMSO) δ 9.40 (1H, s), 8.40 (1H, d, J 5.1 Hz), 7.80 (2H, m), 7.45 (4H, m), 7.30 (2H, m), 7.20 (3H, m), 7.10 (2, t, J 8.9 Hz), 5.70 (2H, s), 4.50 (1H, dd, J 8.7, 6.8 Hz), 3.10 (1H, dd, J 16.6, 8.7 Hz), 2.80 (1H, dd, J 16.5, 6.7 Hz). MS (ES) m/e 469 [M+H]$^+$.

EXAMPLE 28

3-{-2-[4-(2-Amino-1H-imidazol-1-ylmethyl)phenoxy}-4-pyrimidinyl}-3-(4-fluoronhenyl)propanoic acid trifluoroacetic acid salt The title compound (550 mg, 65%) was prepared from Intermediate 57 (0.95 g, 1.94 mmol) in a similar manner to the compound of Example 7. $^1$H NMR (d$^6$ DMSO) δ 8.40 (1H, d, J 5.1 Hz), 7.80 (2H, br s), 7.31 (4H, m), 7.20 (3H, m), 7.10 (3H, m), 7.01 (1H, s), 5.10 (2H, s), 4.50 (1H, t, J 7.7 Hz), 3.20 (1H, dd, J 16.6, 8.8 Hz) and 2.80 (1H, dd, J 16.6, 6.8 Hz). MS (ES) m/e 434 [M+H]$^+$.

EXAMPLE 29

3-(2-{4-[(2-Pyridinylamino)methyl]phenoxy}-4-pyrimidinyl)-3-(3-trifluoromethoxyphenyl)propanoic acid The title compound (1.0 g, 74%) was prepared from Intermediate 60 (1.35 g, 2.66 mmol) in a similar manner to the compound of Example 3. $^1$H NMR (d$^6$ DMSO) δ 9.18 (1H, br s), 8.48 (1H, d, J 5.0 Hz), 8.01 (1H, d, J 6.5 Hz), 7.92 (1H, d, J 7.8 Hz), 7.48–7.38 (3H, m), 7.37–7.31 (2H, m), 7.28 (1H, d, J 5.0 Hz), 7.24–7.16 (3H, m), 3.22 (1H, dd, J 16.6, 8.7 Hz) and 2.88 (1H, dd, J 16.5, 6.8 Hz). MS (ES) m/e 511 [M+H]$^+$.

EXAMPLE 30

3-(3-Cyanophenyl)-3-(2-[4-{(2-pyridinylamino)methyl}phenyl}-4-pyrimidinyl)propanoic acid The title compound (650 mg, 44%) was prepared from Intermediate 63 (1.53 g, 3.3 mmol) in a similar manner to the compound of Example 3. $^1$H NMR (d$^6$ DMSO) δ 8.46 (1H, d, J 5.1 Hz), 7.82 (1H, t, J 1.5 Hz), 7.71–7.64 (2H, m), 7.49 (1H, t, J 7.8 Hz), 7.40–7.34 (3H, m), 7.25 (1H, d, J 5.1 Hz), 7.1 (2H, d, J 8.5 Hz), 7.0 (1H, t, J 6.0 Hz), 6.5 (1H, d, J 8.2 Hz), 6.48–6.45 (1H, m), 4.59 (1H, t, J 7.7 Hz), 4.49 (2H, d, J 4.8 Hz), 3.2 (1H, dd, J 16.6, 8.5 Hz) and 2.90 (1H, dd, J 16.6, 7.0 Hz). MS (ES) m/e 452 [M+H]$^+$.

EXAMPLE 31

3-(3-Methoxyohenyl)-3-(2-{4-[(2-pyrdidnylamino)methyl]phenoxy}-4-pyrimidinyl)propanoic acid The title compound (1.7 g, 59%) was prepared from Intermediate 66 (2.95 g, 6.28 mmol) in a similar manner to the compound of Example 3. $^1$H NMR (d$^6$ DMSO) δ 12.10 (1H, br s), 8.30 (1H, d, J 5.1 Hz), 7.80 (1H, dd, J 4.6, 1.1 Hz), 7.51 (1H, t, J 7.6 Hz), 7.27 (2H, d, J 8.5 Hz), 7.10–7.03 (4H, m), 6.80–6.70 (4H, m), 6.60 (1H, t, J 6.2 Hz), 4.40 (2H,s), 4.30 (1H, dd, J 8.9, 6.5 Hz), 3.60 (3H, s), 3.10 (1H, dd, J 16.6, 9.0 Hz), 2.70 (1H, dd, J 16.6, 6.5). MS (ES) m/e 457 [M+H]$^+$.

EXAMPLE 32

3-(2-{4-[(2-Pyrndinylamino)methyl]phenoxy}-4-pyrimidinyl)-3-(4-trifluoromethoxyphenyl)pronanoic acid The title compound (1.35 g, 58%) was prepared from Intermediate 69 (2.37 g, 4.54 mmol) in a similar manner to the compound of Example 3. $^1$H NMR (d$^6$ DMSO) δ 12.20 (1H, br s), 8.40 (1H, d, J 5.1 Hz), 7.91 (1H, d, J 5.3 Hz), 7.80 (1H, m), 7.39 (4H, m), 7.22 (3H, m), 7.14 (2H, d, J 8.5 Hz), 7.00 (1H, d, J 9.0 Hz), 6.80 (1H, t, J 6.5 Hz), 4.5 (3H, m), 3.16 (1H, dd, J 16.6, 8.8 Hz) and 2.82 (1H, dd, J 16.6, 6.7 Hz). MS (ES) m/e 511 [M+H]$^+$.

EXAMPLE 33

3-(4-Biphenyl)-3-{2-[4-({2-pyridinylamino}methyl)phenoxy]-4-pyrimidinyl}proganoic acid The title compound (850 mg, 61%) was prepared from Intermediate 72 (1.47 g, 2.77 mmol) in a similar manner to the compound of Example 3. $^1$H NMR (d$^6$ DMSO) δ 8.46 (1H, d, J 5.2 Hz), 7.97 (1H, d, J 6.5 Hz), 7.69 (1H, t, J 7.8 Hz), 7.61–7.54 (4H, m), 7.47–7.31 (7H, m), 7.28 (1H, d, J 5.2 Hz), 7.19 (2H, d, J 8.5 Hz), 6.88 (1H, d, J 8.5 Hz), 6.72 (1H, t, J 6.5 Hz), 4.54 (3H, br s), 3.27 (1H,dd, J 16.5, 7.8 Hz) and 2.89 (1H, dd, J 16.5, 6.5 Hz). MS (ES) m/e 503 [M+H]$^+$.

EXAMPLE 34

3-(2-{4-](2-Pyridinylamino)methyl]phenoxy}-4-pyrimidinyl)-3-(4-trifluoromethylphenyl)propanoic acid The title compound (0.81 g, 54%) was prepared from Intermediate 75 (1.54 g, 3.03 mmol) in a similar manner to the compound of Example 5. $^1$H NMR (d$^6$ DMSO) δ 8.54 (1H, d, J 5.1 Hz), 8.04 (1H, d, J 3.2 Hz), 7.74 (2H, d, J 8.3 Hz), 7.64 (2H, d, J 8.2 Hz), 7.47–7.43 (3H, m), 7.34 (1H, d, J 5.1 Hz), 7.19 (2H, d, J 8.5 Hz), 7.14 (1H, t, J 6.1 Hz), 6.61 (1H, d, J 8.4 Hz), 6.58–6.54 (1H, m), 4.71 (1H, t, J 7.7 Hz), 4.59 (2H, d, J 4.9 Hz), 3.31 (1H, m) and 3.01 (1H, m). MS (ES) m/e 495 [M+H]$^+$.

EXAMPLE 35

3-[-2-(4-{(2-Pyridinylamino)methyl}anilino)-4-poramidiny]propanoic

The title compound (332 mg, 89%) was prepared from Intermediate 83 (400 mg, 1.06 mmol) in a similar manner to the compound of Example 5. $^1$H NMR (d$^6$ DMSO) δ 8.29 (1H, d, J 5.0 Hz), 7.92 (1H, d, J 3.9 Hz), 7.67 (2H, d, J 8.4 Hz), 7.42–7.33 (1H, m), 7.22 (2H, d, J 8.4 Hz), 6.70 (1H, d, J 5.0 Hz), 6.59–4.45 (2H, m), 4.38 (2H, m), 2.84 (2H, t, J 7.1 Hz) and 2.69 (2H, t, J 7.1 Hz). MS (ES) m/e 350 [M+H]$^+$.

EXAMPLE 36

3-{2-{4-(2-Amino-6-pyridinyl)phenoxy}-4-pyrimidinyl]-3-(4-fluorophenyl)propanoic acid trifluoroacetic acid salt Intermediate 88 (300 mg, 0.49 mmol) was dissolved in trifluoroacetic acid (20 ml) and the resulting solution stirred for 4 h. The trifluoroacetic acid was then removed in vacuo. The residue was purified by radial chromatography (5%→20% methanol in dichloromethane-4 mm silica plate). Freeze drying from methanol/water gave the title compound as a white solid (145 mg, 69%) $^1$H NMR (d$^6$ DMSO) δ 8.48 (1H, d, J 5.1 Hz), 7.93 (2H, d, J 8.6 Hz), 7.19–7.10 (3H, m), 6.77 (1H, br s), 4.54 (1H, dd, J 8.8, 6.7 Hz), 3.20 (1H, dd J 16.6, 8.8 Hz) and 2.83 (1H, dd, J 16.6, 6.7 Hz). MS (ES) m/e 431 [M+H]$^+$.

EXAMPLE 37

3-[2-(4-{2-Pyrimidinyl}phenoxy)-4-pyrimidinyl]-3-(4-fluorophenyl) propanoic acid trifluoroacetic acid salt The title compound (167 mg, 47%) was prepared from Intermediate 91 (400 mg, 0.85 mmol) in a similar manner to the compound of Example 7. $^1$H NMR (d$^6$ DMSO) δ 8.91 (2H, d, J 4.9 Hz), 8.50 (1H, d, J 5.0 Hz), 8.45 (2H, d, J 8.8 Hz), 7.44 (1H, t, J 4.9 Hz), 7.40–7.31 (4H, m), 7.25 (1H, d, J 5.0 Hz), 7.11 (2H, t, J 8.8 Hz), 4.53 (1H, dd, J 8.8, 6.7 Hz), 3.19 (1H, dd, J 16.6, 8.8 Hz) and 2.81 (1H, dd, J 16.6, 6.7 Hz). MS (ES) m/e 417 [M+H]$^+$.

EXAMPLE 38

3-[2-(4-{2-Imidazole}phenoxgy)-4-pyrimidinyl]-3-(4-fluorophenyl) propanoic acid trifluoroacetic acid salt The title compound (232 mg, 33%) was prepared from Intermediate 94 (860 mg, 1.87 mmol) in a similar manner to the compound of Example 7. $^1$H NMR (d$^6$ DMSO) δ 8.50 (1H, d, J 5.0 Hz), 8.06 (2H, d, J 8.7 Hz), 7.80 (2H, s), 7.49 (2H, d, J 8.7 Hz), 7.35 (2H, dd, J 8.6, 5.6 Hz), 7.29 (1H, d, J 5.0 Hz), 7.12 (2H, t, J 8.9 Hz), 4.54 (1H, dd, J 8.8 and 6.7 Hz), 3.18 (1H, dd, J 16.6, 8.8 Hz) and 2.83 (1H, dd, J 16.6, 6.7 Hz). MS (ES) m/e 405 [M+H]$^+$.

EXAMPLE 39

3-[2-(4-{6-Amino-2-pyridinyl}henoxy)-4-pyrimidinyl]-3-(4-carboxyphenyl)propanoic acid trifluoroacetic acid salt The title compound (188 mg, 20%) was prepared from Intermediate 95 (700 mg, 1.08 mmol) sequentially by the methods used to prepare the compounds of Examples 5 and 7. $^1$H NMR (d$^6$ DMSO) δ 8.49 (1H, d, J 5.0 Hz), 7.94 (2H, d, J 8.5 Hz), 7.86 (2H, d, J 8.2 Hz), 7.78–7.67 (1H, m), 7.44 (2H, d, J 8.2 Hz), 7.34 (2H, d, J 8.5 Hz), 7.28 (1H, d, J 5.0 Hz), 7.15 (1H, d, J 7.4 Hz), 6.77–6.62 (1H, m), 4.60 (1H, dd, J 8.6, 6.7 Hz), 3.23 (1H, dd, J 16.7, 8.6 Hz) and 2.88 (1H, dd, J 16.7, 6.7 Hz). MS (ES) m/e 457 [M+H]$^+$.

EXAMPLE 40

3-[2-(3-{5-Amino-2-pyridinyl}phenoxy)-4-pyrmidinyl]-3-(fluorophenyl)propanoic acid The title compound (149 mg, 60%) isolated as a bistrifluoroacetic acid salt was prepared from Intermediate 100 (150 mg, 0.24 mmol) in a similar manner to the compound of Example 7. $^1$H NMR (d$^6$ DMSO) δ 8.45 (1H, d, J 5.0 Hz), 7.85 (1H, d, J 7.9 Hz), 7.78 (1H, br s), 7.51–7.42 (2H, m), 7.34 (2H, dd, J 8.7, 5.5 Hz), 7.22 (1H, d, J 5.0 Hz), 7.17–7.10 (1H, m), 7.09–7.00 (3H, m), 6.42 (1H, d, J 8.1 Hz), 6.02–5.98 (1H, m), 4.51 (1H, dd, J 8.8, 6.5 Hz), 3.17 (1H, dd, J 16.4, 8.8 Hz) and 2.77 (1H, dd, J 16.4, 6.5 Hz) MS (ES) m/e 431 [M+H]$^+$.

EXAMPLE 41

3-(2-{4-[(1H.-1,3-Benzimidazol-2-ylamino)methyl]phenoxy}-4-pyrimidinyl)propanoic acid The title compound (30 mg, 5%) was prepared from Intermediate 101 (700 mg, 1.84 mmol) in a similar manner to the compound of Example 5.1 H NMR (d$^6$ DMSO) δ 8.43 (1H, d, J 5.0 Hz), 7.48 (2H, d, J 8.5 Hz), 7.39 (2H, dd, J 5.9, 3.2 Hz), 7.24–7.19 (4H, m), 7.16 (1H, d, J 5.1 Hz), 4.67–4.66 (2H, m), 2.91 (2H, t, J 7.2 Hz) and 2.64 (2H, t, J 7.2HZ). MS (ES) m/e 390 [M+H]$^+$.

EXAMPLE 42

3-(2-{N-Propyl-4-[(2-pyridinylamino)methyl]anilmno}-4-pyrimidinyl)propanoic acid The title compound (68 mg, 12%) was prepared from Intermediate 104 (600 mg, 1.43 mmol) in a similar manner to the compound of Example 5. $^1$H NMR (d$^6$ DMSO) δ 8.10 (1H, d, J 4.9 Hz), 7.94 (1H, s), 7.35–7.29 (2H, m), 7.18–7.15 (2H, m), 7.00 (1H, m), 6.56–4.44 (3H, m), 4.45 (2H, s), 3.85 (2H, t, J 7.2 Hz), 2.73 (2H, t, J 7.1 Hz), 2.49 (2H, s), 1.55 (2H, q, J 7.2 Hz) and 0.82 (3H, t, J 7.3 Hz). MS (ES) m/e 392 [M+H]$^+$.

EXAMPLE 43

3-{2-[4-(1H-Imidazol-2-ylmethyl)phenoxy]-4-pyrimidinyl}propanoic acid

The title compound (65 mg, 28%) was prepared from Intermediate 109 (250 mg, 0.71 mmol) in a similar manner to the compound of Example 5. $^1$H NMR (DMSO) δ 8.44 (1H, d, J 5.0 Hz), 7.54 (2H, s), 7.38 (2H, dd, J 6.6, 2.0 Hz), 7.19 (3H, dd, J 6.4, 2.1 Hz), 4.32 (2H, s), 2.92 (2H, t, J 7.2 Hz), 2.65 (2H, t, J 7.3 Hz). m/z 325 MH$^+$.

EXAMPLE 44

3-(4-Fluorophenyl)-3-(2-{4-hydroxy-[1H-imidazol-2-yl]methylphenoxy}-4-pyrimidinyl)propanoic acid The title compound (60 mg, 39.5%) was prepared from Intermediate 112 (160 mg, 0.35 mmol) in a similar manner to the compound of Example 5. $^1$H NMR (d$^6$ DMSO) δ 8.46 (1H, d, J 5.1 HZ), 7.55 (1H, s), 7.40 (2H, m), 7.25 (3H, d, J 5.0 Hz), 7.17 (6H, t, J 7.9 Hz), 4.55 (2H, dd, J 8.6, 6.8 Hz), 3.24 (1H, dd, J 8.8, 6.6 Hz), 2.93–2.84 (1H, m). MS (ES) m/e 435 [M+H]$^+$.

EXAMPLE 45

3-(3-Bromophenyl)-3-(2{-4-[2-pyridinylamino)methyl]phenoxy}-4-pyrimidinyl)propanoic acid trifluoroacetic acid salt The title compound (5.0 g, 93%) was prepared from Intermediate 115 (6.0 g, 11.9 mmol) in a similar manner to the compound of Example 7. $^1$H NMR (CDCl$_3$) δ 9.70 (1H, br s), 8.40 (1H, d, J 5.1 Hz), 7.80 (2H, m), 7.50–7.00 (10H, m), 6.80 (1H, m), 4.60 (2H, s), 4.45 (1H, m), 3.15 (1H, dd, J 10.0, 17.0 Hz), 2.65 (1H, dd, J 4.8, 17.0 Hz). MS (ES) m/e 507 [M+H]$^+$.

EXAMPLE 46

3-(2-{4-[(4,5-Dihydro-1H-imidazol-2-ylamino) methyl]phenoxy}-4-pyrimidinyl)propanoic acid The title compound (0.16 g, 13%) isolated as the octa trifluoroacetate salt was prepared from Intermediate 126 (0.38 g, 1.03 mmol) in a similar manner to the compoud of Example 3. $^1$H NMR (d$^6$ DMSO) δ 12.26 (1H, br s), 8.95 (1H, br s), 8.46 (1H, d, J 4.0 Hz), 7.36 (2H, d, J 8.0 Hz), 7.19 (2H, d, J 8.0 Hz), 7.18 (1H, d, J 4.0 Hz), 4.41 (2H, t, J 3.0 Hz), 3.62 (4H, s), 2.92 (2H, t, J 7.0 Hz) and 2.66 (2H, t, J 7.0 Hz). MS (ES) m/e 342 [M+H]$^+$.

EXAMPLE 47

3-[2-(4-{2-(N-methylamino)-6-pyridinyl}phenoxy)-4-pyrimidinyl]-3-(4-carboxyphenyl)propanoic acid trifluoroacetic acid salt The title compound (74 mg, 17%) was prepared from Intermediate 129 (600 mg, 0.91 mmol) sequentially by the methods used to prepare the compounds of Examples 5 and 7. $^1$H NMR (d$^6$ DMSO) δ 8.48 (1H, d, J 5.0 Hz), 8.02 (2H, d, J 8.6 Hz), 7.86 (2H, d, J 8.3 Hz), 7.66–7.55 (1H, m), 7.45 (2H, d, J 8.3 Hz), 7.28 (2H, d, J 8.6 Hz), 7.27 (1H, d J 5.0 Hz), 7.10 (1H, d, J 7.3 Hz), 6.58 (1H, br s),4.60 (1H, dd, J 8.7, 6.7 Hz), 3.24 (1H, dd, J 16.7, 8.7 Hz), 2.90 (3H, s), 2.87 (1H, dd, J 16.7, 6.7 Hz). MS (ES) m/e 471 [M+H]$^+$.

EXAMPLE 48

3-(2-[4-{(2-Pyridinylamino)methyl}-N-benzylanilinog]-4-pyromidinyl) propanoic acid The title compound (141 mg, 59%) was prepared from Intermediate 132 (250 mg, 0.54 mmol) in a similar manner to the compound of Example 5. $^1$H NMR (d6 DMSO) δ 8.17 (1H, d, J 5.0 Hz), 7.93 (1H, d, J 5.2 Hz), 7.52 (1H, br t, J 7.8 Hz), 7.32–7.15 (9H, m), 6.70–6.62 (2H, m), 6.59 (1H, t, J 6.1 Hz), 5.23 (2H, s), 4.46 (2H, s), 2.77 (2H, t, J 7.1 Hz) and 2.56 (2H, t, J 7.1 Hz). MS (ES) m/e 440 [M+H]$^+$.

EXAMPLE 49

3-(4-Fluorophenyl-3-(2-{4-[(2-imino-2-methylamino) ethyl]phenoxy}-4-(pyrimidinyl)propanoic acid trifluoroacetic acid salt The title compound (80 mg, 26%) was prepared from Intermediate 135 (350 mg, 0.75 mmol) in a similar manner to the compound of Example 7. $^1$H NMR (d$^6$ DMSO) δ 8.41 (1H, d, J 5.6 Hz), 7.487.29 (4H, m), 7.21–7.00 (5H, m), 4.48 (1H, t, J 8.6 Hz), 3.71 (2H, s), 3.15 (1H, dd, J 16.4, 8.6 Hz) and 2.90–2.71 (4H,m). MS (ES) m/e 409 [M+H]$^+$.

EXAMPLE 50

3-{2-[4-({[Amino(imino)methyl]amino}methyl) phenoxy]-4-pyrimidinyl}-3-(4-benzoic acidipropanoic acid trifluoroacetic acid salt The title compound (50 mg, 8%) was prepared from Intermediate 136 (1.1 g, 1.5 mmol) sequentially by the methods used to prepare the compounds of Examples 5 and 7. $^1$H NMR (d$^6$ DMSO) δ 8.42 (1H, d, J 6.2 Hz), 798–7.92 (2H, d, J 5.8 Hz), 7.63 (2H, d, J 8.4 Hz), 7.35 (2H, d, J 8.6 Hz), 7.25–7.14 (3H, m), 4.61 (6H, t, J 8.6 Hz), 4.35 (2H, d, J 7.2 Hz), 3.21 (1H, dd, J 16.4, 8.6 Hz) and 2.84 (1H, J 16.4, 8.2 Hz). MS (ES) 436 [M+H]$^+$.

EXAMPLE 51

3-(4-Fluorophenyl)-3-{2-(4-[{imino(2-pyrdinyl) methyl}amino)methyl]phenoxy)-4-pyrimidinyl}propanoic acid trifluoroacetic acid salt The title compound (70 mg, 40%) was prepared from Intermediate 139 (200 mg, 0.37 mmol) in a similar manner to the compound of Example 7. $^1$H NMR (d$^6$ DMSO) δ 8.58 (1H, d, J 7.8 Hz), 8.41 (1H, d, J 7.8 Hz), 8.22 (1H, d, J 8.6 Hz), 7.92 (1H, t, J 8.6 Hz), 7.42–7.10 (10H, m), 4.72 (2H, br s), 4.42 (1H, t, J 8.6 Hz), 3.13 (1H, dd, J 16.2, 8.6 Hz) and 2.78 (1H, dd, J 16.4, 8.6 Hz). MS (ES) m/e 472 [M+H]$^+$.

EXAMPLE 52

3-(4-Fluorophenyl)-3-[2-(4-{quanidinocarbonyl}phenoxy)-4-pyrimidinyl] propanoic acid A slurry of derivatised resin (Intermediate 141) (120 mg) in DMF (2 ml) was treated with N4tertbutyloxycarbonylguanidine (123 mg, 0.84 mmol), [O-(7-azabenzotriazol-1-yl)-1,1,3,3-tetramethyluronium] hexafluorophosphate (319 mg, 0.84 mmol) and diisopropylethylamine(108 mg, 0.84 mmol). The resulting mixture was agitated for 18 h at room temperature, then filtered and the resin washed with DMF, dichloromethane and methanol. The resin was treated with a solution of trifluoroacetic acid/dichloromethane (1:1, 3 ml) for 1 h, then filtered. The filtrate was evaporated in vacuo to afford the title compound (20 mg) as its trifluoroacetic acid salt. HPLC-MS (see below) Retention time 2.1 min, MH$^+$ 424.

EXAMPLE 53

3-(4-(3-Chloro-4-fluoroohenyl)phenyl)-3-[2-(4-({2-pyridinylamino}methyl)phenoxy)-4-pyrimidinyl] propanoic acid A slurry of derivatised resin (Intermediate 142) (120 mg, 0.08 mmol) in anhydrous/degassed DMF (1 mL) was treated with 3-chloro-4-fluorophenylboronic acid (18 mg, 0.10 mmol), potassium carbonate (28 mg, 0.20 mmol) and tetrakis(triphenylphosphine)palladium (0) (6 mg, 0.005 mmol). The resulting mixture was heated to 800 and agitated for 18 h. The reaction mixture was cooled to room temperature and then filtered. The resin was washed with DMF, water, dichloromethane and methanol. The resin was treated with a solution of trifluoroacetic acid/dichloromethane (95:5, 1 mL) for 1 h, then filtered. The filtrate was evaporated to afford the title compound (1 mg). HPLC-MS Retention time 2.35 min MH+ 555

The compounds of Examples 54 to 60 were prepared in a similar manner to the compound of Example 53, using the arylboronic acid shown.

EXAMPLE 54

3-(4-(3-Acetamidophenyl)phenyl)-3-[2-(4-({2-pyridinylamino}methyl) phenoxy)-4-pyrimidinyl] propanoic acid Using derivatised resin (Intermediate 142) and 3-acetamidobenzene boronic acid yielded the title compound. HPLC-MS Retention time 2.13 min MH+ 560

EXAMPLE 55

3-(4-(2-Formylthienyl)phenyl)-3-[2-(4-({2-pridinylamino}methyl) phenoxy)-4primidinyl] propanoic acid Using derivatised resin (Intermediate 142) and 2-formylthiophene-3-boronic acid yielded the title compound. HPLC-MS Retention time 2.19 min MH+ 537

EXAMPLE 56

3-(4-(3,4-Dichlorophenyl)phenyl)-3-[2-(4-({2-pyridinylamino}methyl) phenoxy)-4-pyrimidinyl] propanoic acid Using derivatised resin (Intermediate 142) and 3,4-dichlorophenylboronic acid yielded the title compound. HPLC-MS Retention time 2.38 min MH+ 571

EXAMPLE 57

3-(4-(4-Isopropylohenyl)phenyl)-3-[2-(4-({2-pyridinylamino}methyl) phenoxy)-4-pyrimidinyl] propanoic acid Using derivatised resin (Intermediate 142) and 4-isopropylphenylboronic acid yielded the title compound. HPLC-MS Retention time 2.39 min MH+ 545

EXAMPLE 58

3-(4-(2-Formnylphenyl)phenyl)-3-[2-(4-({2-pyridinylamino}methyl) phenoxy)-4-pyrimidinyl] propanoic acid Using derivatised resin (intermediate 142) and 2-formylbenzeneboronic acid yielded the title compound. HPLC-MS Retention time 2.21 min MH+ 531

EXAMPLE 59

3-(4-(1-Naphthyl)phenyl)-3-[2-(4-({2-pyridinylamino}methylphenoxy)-4-pyrimidinyl] propanoic acid Using derivatised resin (Intermediate 142) and 1-naphthaleneboronic acid yielded the title compound. HPLC-MS Retention time 2.36 min MH+ 553

EXAMPLE 60

3-(4-(4-t-Butylphenyl)phenyl)-3-[2-(4-({2-pyridinylamino}methyl)phenoxy)-4-pyrimidinyl] propanoic acid Using derivatised resin (Intermediate 142) and 4-t-butylbenzeneboronic acid yielded the title compound. HPLC-MS Retention time 2.49 min MH+ 559

EXAMPLE 61

3-(3-Benzenecarboxylic acid)-3-(2-{4-[(2-pyridinylamino)methyl]phenoxy}-4-pyromidinyl) propanoic salt The title comlund (770 mg, 84%) was prepared from intermediate 145 (0.97 g, 1.95 mmol) in a similar manner to the compound of Example 5. $^1$H NMR (d$^6$ DMSO) δ 8.46 (1H, d, J 5.0 Hz), 7.99–7.97 (1H,m), 7.89 (1H, t, J 1.7 Hz), 7.81 (1H, d, J 7.6 Hz), 7.58–7.53 (2H, m), 7.42 –7.38 (3H, m), 7.18 (1H, d, J 5.1 Hz), 7.13 (2H, d, J 8.7 Hz), 6.75 (1H, d, J 8.6 Hz), 6.65–6.62 (1H, m), 4.61–4.57 (3H,m), 3.20 (1H, dd, J 16.3, 8.0 Hz), 2.89 (1H, dd, J 16.3, 7.1 Hz), MS (ES) m/e 471 [M+H]$^+$.

HPLC-MS

A Luna C18(2) 50×2.0 mm (3 μm) column, running a gradient of 95% [0.1% aqueous formic acid], 5% [0.1% formic acid in acetonitrile] to 10% [0.1% aqueous formic acid], 90% [0.1% formic acid in acetonitrile] over 2 min, then maintaining the mobile phase at that ratio for a further imin. Flow rate 0.8 ml/min.

MS was acquired by API electrospray in positive ion mode, at 70V, scanning from 150 to 750 amu.

The following assays may be used to determine the ability of compounds according to the invention to inhibit $α_vβ_3$ and $α_vγ_5$ function.

$α_vβ_3$-Dependent Direct Binding Assay

96 Well NUNC immunoplates were coated overnight with a non-blocking anti-β3 monoclonal antibody at 2 μg/ml in Dulbecco's phosphate buffered saline (PBS) and subsequently blocked with 5% 9$^w$/$_v$)BSA in PBS (Sigma, fraction V) for 60 min. at room temperature. After washing in Tris-buffered saline (TBS: 20 mM Tris/150 mM NaCl, pH 7.5), plates then received 100 μl of a lysate prepared from JY cells and were incubated for 3 h at room temperature. The lysate was made by lysing JY B-lymphoblastoid cells at 5×10$^7$ cells were ml in TBS containing 1 mM MnCl$_2$, 1% ($^v$/$_v$) BSA/0.1% ($^vb$/$_v$) Tween 20 and were incubated for a further 2 hours at room temperature. Inhibitors were titrated into the fibronectin prior to addition to plates. After washing, streptavidin-peroxidase (Amersham) at 1:500 in TBS/1% ($^w$/$_v$) BSA/0.1% ($^v$/$_v$)Tween 20 was added and plates incubated for 1 h at room temperature. Finally 100 μl TMB substrate was added and Absorbance (630nm) measured after 10–15 miunbutes. IC$_{50}$ values for inhibition of adhesion were calculated on the Activity Base curve fitting programme.

$α_vβ_3$-Dependent Cell Adhesion Assay

This was a modification of a published method [Stupack et al, Exp. Cell. Tes. 203, 443–448 (1992)] and employed the JY cell line. These cells are maintained in RPMI 1640+10% FCS+2 mM L-glutamine and, when used for assay, were washed in assat medium (RPMI 1640+10% FCS), suspended at 4×10$^6$/ml in the same medium and pretreated with a blocking monoclonal antibody to CD18 (6.5E, F(ab')$_2$ fragment) for 10 min at room temperature. 96 Well NUNC immunoplates were coated with 100 μl 2.5 μk/μl human vitronectin in PBS per well for 2 h at 37° C.; they were then washed 2× in PBS and blocked with 1% ($^w$/$_v$) BSA in PBS for 60 min at room temperature and washed 2× more in PBS. 2×1–$^5$ JY per well were added to wells containing compounds serially titrated across the plate and, finally, phorbol-12-myristate-13-acetate at 10 ng/ml was added in a final volume of 200 μl. After incubation at 37° C. for 30 min, non-adherent cells were removed by washing 3× in assay medium, adherent cells were fixed in methanol and stained with 0.25% ($^w$/$_v$) Rose Bengal in PBS for 5 min, unbound dye was removed by 3 further washes in PBS and cell-bound dye was released with 1:1 PBS:ethanol. Absorbance at 570 nm was then measured. IC$_{50}$ values for inhibition of adhesion were calculated as described above for the direct binding assay.

$α_vβ_5$-Dependent Cell Adhesion Assay

This assay was based on a published method [Koivunen et al, J. Bio. Chem. 26, 20205–20210 (1993)] and employed the human colon adenocarcinoma cell line HT-29. HT-29 Cells were routinely maintained in DMEM+10% FCS+2 mM L-glutamine and were removed from flasks using trypsin/EDTA, washed 2× in assay medium and suspended at 4×10$^6$/ml in the same medium. The cells were allowed to 'rest' for 15 min. at room temperature before being added (2×10$^5$/well) to wells containing compounds serially titrated across the plate in a final volume of 200 μl. The 96 well NUNC immunoplates had been coated with human vitronectin as described above for the $\alpha_v\beta_3$ assay. After incubation at 37° C. for 60 min, adhesion was assessed as described above for the $\alpha_v\beta_3$ assay.

In the above assays the preferred compounds of the invention generally have IC$_{50}$ values of 1 μM and below.

What is claimed is:

1. A compound of formula (1):

wherein:

(1) Ar is a group R$^{1a}$N(R$^2$)L$^1$Ar$^2$— in which:
R$^{1a}$ is an optionally substituted imidazolyl, triazolyl, pyridyl, benzimidazolyl or imidazolinyl group;
R$^2$ is a hydrogen atom or an optionally substituted aliphatic, heteroaliphatic, cycloaliphatic, polycycloaliphatic, heterocycloaliphatic, heteropolycycloaliphatic, aromatic or heteroaromatic group;
L$^1$ is a —C(R$^3$)(R$^4$)— (where R$^3$ and R$^4$, which may be the same or different, is each a hydrogen atom or a straight or branched C$_{1-6}$alkyl group), —C(O)—, —C(S)—, —S(O)—, —S(O)$_2$—, —P(O)—, —P(O)(OR$^a$)— (where R$^a$ is a hydrogen atom or a straight or branched C$_{1-6}$alkyl group) or —P(O)(OR$^a$)O— group; and
Ar$^2$ is an optionally substituted six-membered 1,4-arylene or 1,4-heteroarylene ring; or (2) Ar is a group R$^{1b}$Ar$^2$ in which R$^{1b}$ is an optionally substituted imidazolyl, triazolyl, pyridyl, benzimidazolyl or imidazolinyl group; or (3) Ar is a group R$^{1d}$L$^1$Ar$^2$— in which R$^{1d}$ is an optionally substituted imidazolyl, triazolyl, pyridyl, benzimidazolyl or imidazolinyl group;

X$^1$ is an —O— or —S— atom or a group selected from —C(O)—, —C(S)—, —S(O)—, —S(O)$_2$—, —N(R$^5$)— (where R$^5$ is a hydrogen atom or an optionally substituted straight or branched alkyl group), —C(R$^5$)(R$^6$)— (where R$^6$ is a hydrogen or halogen atom or a straight or branched alkyl, haloalkyl, alkoxy, haloalkoxy, alkylthio, aromatic, heteroaromatic, or —(Alk$^1$)$_m$R$^7$ group (in which Alk$^1$ is a C$_{1-3}$alkylene chain, m is zero or the integer 1 and R$^7$ is a —OH, —SH, —NO$_2$ —CN, —CO$_2$H, —CO$_2$R$^8$ (where R$^8$ is an optionally substituted straight or branched C$_{1-6}$alkyl group), —SO$_3$H, —SOR$^8$, —SO$_2$R$^8$, —OCO$_2$R$^8$, C(O)H, —C(O)R$^8$, —OC(O)R$^8$, —C(S)R$^8$, —NR$^9$R$^{10}$ (where R$^9$ and R$^{10}$, which may be the same or different is each a hydrogen atom or a straight or branched alkyl group), —C(O)N(R$^9$)(R$^{10}$), —OC(O)N(R$^9$)(R$^{10}$), —N(R$^9$)C(O)R$^{10}$, —CSN(R$^9$)(R$^{10}$), —N(R$^9$)C(S)R$^{10}$, —SO$_2$N(R$^9$)(R$^{10}$), —N(R$^9$)SO$_2$R$^{10}$, —N(R$^9$)C(O)N(R$^{10}$)(R$^{11}$) (where R$^{11}$ is a hydrogen atom or a straight or branched alkyl group), —N(R$^9$)C(S)N(R$^{10}$)(R$^{11}$), —N(R$^9$)SO$_2$N(R$^{10}$)(R$^{11}$), aromatic group or heteroaromatic group));
Z is a group —CH(R$^{13}$)CH$_2$— (in which R$^{13}$ is an optionally substituted aliphatic, cycloaliphatic, heteroaliphatic, heterocycloaliphatic, aromatic or heteroaromatic group), —C(R$^{12a}$)(R$^{13}$)—CH(R$^{12b}$)—

(in which R$^{12a}$ and R$^{12b}$ together with the carbon atoms to which they are attached form a C$_{3-7}$cycloalkyl group) or —C(R$^{13}$)=CH—;
R is a carboxylic acid (—CO$_2$H) or a carboxylic acid ester or amide derivative or a tetrazole, squaric acid, phosphoric acid, sulphonic acid, sulphinic acid or boronic acid biostere thereof;
Ar$^1$ is a 6-membered nitrogen-containing aromatic monocycle of formula:

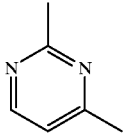

and the salts, solvates, hydrates and N-oxides thereof.

2. A compound according to claim 1 in which R is a —CO$_2$H group.

3. A compound according to claim 1 in which X$^1$ is a —O—, —S—, —NH— or —N(CH$_3$)— group.

4. A compound according to claim 1 in which L$^1$ is a group —C(R$^3$)(R$^4$)— or —CO—.

5. A compound according to claim 4 in which L$^1$ is a group —CH$_2$—.

6. A compound according to claim 1 in which Ar is a group R$^{1a}$N(R$^2$)L$^1$Ar$^2$ in which R$^2$ is a hydrogen atom.

7. A compound according to claim 6 in which R$^{1a}$ is an optionally substituted imidazolinyl, benzimidazolyl or pyridyl group.

8. A compound according to claim 1 in which Ar is a group R$^{1b}$Ar$^2$ in which R$^{1b}$ is an optionally substituted pyridyl or imidazolyl group.

9. A compound according to claim 1 in which Ar is a group R$^{1d}$L$^1$Ar$^2$ in which R$^{1d}$ is an optionally substituted imidazolyl, imidazolinyl, triazolyl or pyridyl group.

10. A compound according to claim 1 in which Z is a group —CH(R$^{13}$)CH$_2$— or —C(R$^{13}$)=CH—.

11. A compound according to claim 10 in which R$^{13}$ is an optionally substituted aromatic or heteroaromatic group.

12. A compound according to claim 11 in which R$^{13}$ is an optionally substituted phenyl or five- or six-membered heteroaromatic group.

13. A compound according to claim 12 in which R$^{13}$ is an optionally substituted phenyl group.

14. A compound which is:

3-(4-[2-Aminoethyl]benzamide)-3-(2-[4-{(2-pyridinylamino)methyl}phenoxy]4-pyrimidinyl) propanoic acid;

3-(2-{4-[(4,5-Dihydro-1H-imidazol-2-ylamino)methyl]phenoxy}-4-pyrimidinyl)-3-(4-fluorophenyl)propanoic acid;

3-{2-[4-({[Amino(imino)methyl]amino}methyl)phenoxy]-4-pyrimidinyl}-3-(4-benzoic acid)propanoic acid;

3-[2-(4-[({Amino(imino)methyl}amino)methyl]-N-methylaniliino)-4-pyrimidinyl]-3-(4-fluorophenol) propanoic acid;

3-(3-Methoxyphenyl)-3-(2-{4-{(2-pyridinylamino)methyl]phenoxy}-4-pyrimidinyl)propanoic acid;

3-[2-(4-{6-Amino-2-pyridinyl}phenoxy)-4-pyrimidinyl]-3-(4-carboxy phenyl)propanoic acid;

3-[2-(4-{2-(N-methylamino)-6-pyridinyl}phenoxy)-4-pyrimidinyl]-3-(4-carboxyphenyl)propanoic acid;

3-(2-[4-{(1H-1,3-Benzimidazol-2-yl-amino)
methyl}phenoxy]-4-pyrimidinyl)-3-(4-fluorophenyl)
propanoic acid;

3-(3-Benzenecarboxylic acid)-3-(2-{4-[(2-pyridinylamino)methyl]phenoxy}4-pyrimidinyl)
propanoic acid;

and the salts, solvates, hydrates and N-oxides thereof.

15. A pharmaceutical composition comprising a compound according to claim 1 together with one or more pharmaceutically acceptable carriers, excipients or diluents.

* * * * *